United States Patent
Liu et al.

(10) Patent No.: US 9,352,039 B2
(45) Date of Patent: May 31, 2016

(54) METHOD OF REDUCING THE NUMBER OF EMT AND MET TYPE BREAST CANCER STEM CELLS

(71) Applicant: The Regents of the University of Michigan, Ann Arbor, MI (US)

(72) Inventors: Suling Liu, Heifei (CN); Max S. Wicha, Ann Arbor, MI (US)

( * ) Notice: Subject to any disclaimer, the term of this patent is extended or adjusted under 35 U.S.C. 154(b) by 0 days.

(21) Appl. No.: 14/376,923

(22) PCT Filed: Feb. 8, 2013

(86) PCT No.: PCT/US2013/025306
§ 371 (c)(1),
(2) Date: Aug. 6, 2014

(87) PCT Pub. No.: WO2013/119923
PCT Pub. Date: Aug. 15, 2013

(65) Prior Publication Data
US 2015/0125469 A1        May 7, 2015

Related U.S. Application Data

(60) Provisional application No. 61/596,796, filed on Feb. 9, 2012.

(51) Int. Cl.
| | | |
|---|---|---|
| *A61K 39/395* | (2006.01) |
| *A61K 31/7088* | (2006.01) |
| *C12N 15/113* | (2010.01) |
| *A61K 45/06* | (2006.01) |
| *A61K 39/00* | (2006.01) |
| *G01N 33/574* | (2006.01) |

(52) U.S. Cl.
CPC ......... *A61K 39/3955* (2013.01); *A61K 31/7088* (2013.01); *A61K 39/0011* (2013.01); *A61K 45/06* (2013.01); *C12N 15/1135* (2013.01); *C12N 15/1136* (2013.01); *C12N 15/1138* (2013.01); *G01N 33/57484* (2013.01); *A61K 2039/507* (2013.01); *A61K 2039/5154* (2013.01); *C12N 2310/113* (2013.01); *C12N 2310/141* (2013.01); *C12N 2320/31* (2013.01); *C12N 2330/50* (2013.01)

(58) Field of Classification Search
None
See application file for complete search history.

(56) References Cited

U.S. PATENT DOCUMENTS

| | | | |
|---|---|---|---|
| 5,051,448 A | 9/1991 | Shashoua |
| 5,169,862 A | 12/1992 | Burke et al. |
| 5,192,746 A | 3/1993 | Lobl et al. |
| 5,223,409 A | 6/1993 | Ladner et al. |
| 5,539,085 A | 7/1996 | Bischoff et al. |
| 5,545,531 A | 8/1996 | Rava et al. |
| 5,559,103 A | 9/1996 | Gaeta et al. |
| 5,576,423 A | 11/1996 | Aversa et al. |
| 5,599,677 A | 2/1997 | Dowell et al. |
| 5,672,480 A | 9/1997 | Dowell et al. |
| 8,088,617 B2 | 1/2012 | Gurney et al. |
| 8,455,623 B2 | 6/2013 | Van Der Horst et al. |
| 2002/0051785 A1* | 5/2002 | Slamon ............ A61K 39/39558 424/145.1 |
| 2010/0162416 A1* | 6/2010 | Krtolica ............... C12N 5/0606 800/3 |
| 2011/0021607 A1* | 1/2011 | Clarke ................. C12Q 1/6886 514/44 A |
| 2011/0143960 A1* | 6/2011 | LaBarbera ......... G01N 33/5011 506/10 |
| 2011/0165162 A1 | 7/2011 | Hoey et al. |
| 2011/0305695 A1 | 12/2011 | Satyal et al. |
| 2013/0309246 A1* | 11/2013 | Kang ................... C12Q 1/6886 424/158.1 |

FOREIGN PATENT DOCUMENTS

| | | |
|---|---|---|
| WO | WO9617957 | 6/1996 |
| WO | WO2007142711 | 12/2007 |
| WO | WO2008070090 | 6/2008 |
| WO | WO2008091641 | 7/2008 |
| WO | WO2008100563 | 8/2008 |
| WO | WO2008140826 | 11/2008 |
| WO | WO2009005809 | 1/2009 |
| WO | WO2009009114 | 1/2009 |
| WO | WO2011063237 | 5/2011 |
| WO | WO2011088123 | 7/2011 |
| WO | WO2011088215 | 7/2011 |
| WO | WO2011123785 | 10/2011 |

OTHER PUBLICATIONS

Schmalhofer et al., E-cadherin, β-catenin, and ZEB1 in malignant progression of cancer. Cancer Metastasis Rev. 28:151-166, 2009.*

(Continued)

*Primary Examiner* — Elly-Gerald Stoica
(74) *Attorney, Agent, or Firm* — Casimir Jones, S.C.; Jason R. Bond

(57) ABSTRACT

Compositions, kits, and methods for therapeutic screening, diagnostics, and cancer treatment based on the identification or use of the different states of cancer stem cells, including cancer stem cells in the EMT (epithelial to mesenchymal transition) MET (mesenchymal to epithelial transition), and EMT-MET states are disclosed. In some methods, a subject is treated with one therapeutic that targets EMT cancer stem cells and a second therapeutic that targets MET cancers stem cells. In certain methods, the different states of cancer stem cells are distinguished based on markers CD44+CD24–, EpCam–CD49P+ (for EMT cancers stem cells), ALDH+ and EPCam+CD49r– (for MET cancers stem cells), and CD44+CD24–ALDH+ (for EMT-MET cancer stem cells). In particular methods, micro RNAs are used to transition to one particular cancer stem cell type (e.g., mir-100 for EMT and mir-93 for MET).

4 Claims, 33 Drawing Sheets

(56) References Cited

OTHER PUBLICATIONS

Shih et al., The EMT regulator slug and lung carcinogenesis, Carcinogenesis, 32, 1299-1304, 2011.*
Bret et al., The microRNA cluster mir-106b~25 regulates adult neural stem/progenitor cell proliferation and neuronal differentiation. Aging, 3, 108-124, 2011.*
Katoh, Masaru, Network of WNT and other regulatory signaling cascades in pluripotent stem cells and cancer stem cells, Curr. Pharm. Biotech., 12, 160-170, 2011.*
Petrocca et al., Emerging role of miR-106b-25/miR-17-92 clusters in the control of transforming growth factor β signaling, 68, 8191-8194, 2008.*
Aktas et al., Stem cell and epithelial-mesenchymal transition markers are frequently overexpressed in circulating tumor cells of metastatic breast cancer patients. Breast Cancer Res 2009, 11(4):R46.
Al-Hajj et al., Prospective identification of tumorigenic breast cancer cells. Proc Natl Acad Sci U S A 2003, 100(7):3983-3988.
Bandyopadhyay et al., Doxorubicin in combination with a small TGFbeta inhibitor: a potential novel therapy for metastatic breast cancer in mouse models. PLoS One 2010, 5(4):e10365.
Berry et al., Effect of screening and adjuvant therapy on mortality from breast cancer. The New England journal of medicine 2005, 353(17):1784-1792.
Biddle et al, Cancer stem cells in squamous cell carcinoma switch between two distinct phenotypes that are preferentially migratory or proliferative. Cancer Res 2011, 71(15):5317-5326.
Brenner et al., Encoded combinatorial chemistry, Proc. Natl. Acad. Sci. USA 1992, 89:5381-5383.
Britschgi et al., JAK2/STAT5 Inhibition Circumvents Resistance to PI3K/mTOR Blockade: A Rationale for Cotargeting These Pathways in Metastatic Breast Cancer. Cancer Cell 22, 796-811 (2012).
Carell et al., New promise in combinatorial chemistry: synthesis, characterization, and screening of small-molecule libraries in solution, Chem. Biol. 1995, 3:171-183.
Carrell et al., Angew. Chem. Int. Ed. Engl. 33.2059 1994.
Chaffer et al., Mesenchymal-to-epithelial transition facilitates bladder cancer metastasis: role of fibroblast growth factor receptor-2. Cancer Res 2006, 66(23):11271-11278.
Chao et al., Breast carcinoma cells re-express E-cadherin during mesenchymal to epithelial reverting transition. Mol Cancer 2010, 9:179.
Charafe-Jauffret et al., Breast cancer cell lines contain functional cancer stem cells with metastatic capacity and a distinct molecular signature. Cancer Res 2009, 69(4):1302-1313.
Chen et al., Overexpression of miR-429 induces mesenchymal-to-epithelial transition (MET) in metastatic ovarian cancer cells. Gynecol Oncol 2011, 121(1):200-205.
Cho et al., An unnatural biopolymer, Science 1993, 261:1303-1305.
Cancer Genome Atlas Network, Comprehensive molecular portraits of human breast tumours. Nature 2012, 490:61-70.
Conley et al., Antiangiogenic agents increase breast cancer stem cells via the generation of tumor hypoxia. Proc Natl Acad Sci U S A 2012, 109:2784-2789.
Creighton et al., Residual breast cancers after conventional therapy display mesenchymal as well as tumor-initiating features. Proc Natl Acad Sci U S A 2009, 106:13820-13825.
Croce et al., miRNAs, cancer, and stem cell division. Cell 2005, 122(1):6-7.
Cull et al., Screening for receptor ligands using large libraries of peptides linked to the C terminus of the lac repressor. Proc. Nad. Acad. Sci. USA 1992, 89:1865-1869.
Cwirla et al., Peptides on phage: a vast library of peptides for identifying ligands. Proc. Natl. Acad. Sci. 1990, 87:6378-6382.
Davies, Mesenchyme to epithelium transition during development of the mammalian kidney tubule. Acta Anat (Basel) 1996, 156(3):187-201.
Devlin, Random peptide libraries: a source of specific protein binding molecules. Science 1990, 249:404-406.

DeWitt et al., "Diversomers": an approach to nonpeptide, nonoligomeric chemical diversity. Proc. Natl. Acad. Sci. U.S.A. 1993, 90:6909-6913.
Dontu et al., In vitro propagation and transcriptional profiling of human mammary stem/progenitor cells. Genes & Development 2003, 17(10):1253-1270.
Dontu et al., Stem cells in normal breast development and breast cancer. Cell Prolif 2003, 36 Suppl 1:59-72.
Felder, The Challenge of Preparing and Testing Combinatorial Compound Libraries in the Fast Lane, at the Front end of Drug Development, Chimia 1994, 48:512-541.
Eldred et al., Orally active non-peptide fibrinogen receptor (GpIIb/IIIa) antagonists: identification of 4-[4-[4-(aminoiminomethyl)phenyl]-1-piperazinyl]-1-piperidineacetic acid as a long-acting, broad-spectrum antithrombotic agent. J. Med. Chem. 1994, 37:3882-3885.
Erb et al., Recursive deconvolution of combinatorial chemical libraries. Proc. Nad. Acad. Sci. USA 1994, 91:11422-11426.
Felici et al., Selection of antibody ligands from a large library of oligopeptides expressed on a multivalent exposition vector. J. Mol. Biol. 1991, 222:301-310.
Fodor, Multiplexed biochemical assays with biological chips. Nature 1993, 364:555-556.
Gallop et al., Applications of combinatorial technologies to drug discovery. 1. Background and peptide combinatorial libraries. J. Med. Chem. 1994, 37:1233-1251.
Ginestier et al., ALDH1 is a marker of normal and malignant breast stem cells and a predictor of poor clinical outcome. Cell Stem Cell 2007, 1:555-567.
Givan, Flow cytometry: an introduction. Methods Mol Biol 2004, 263, 1-32.
Gjerdrum et al., Axl is an essential epithelial-to-mesenchymal transition-induced regulator of breast cancer metastasis and patient survival. Proc Natl Acad Sci U S A 2010, 107(3):1124-1129.
Gordon et al., Applications of combinatorial technologies to drug discovery. 2. Combinatorial organic synthesis, library screening strategies, and future directions. J. Med. Chem. 1994, 37:1385-1401.
Greene et al., A putative role for microRNA-205 in mammary epithelial cell progenitors. J Cell Sci 2010, 123(Pt 4):606-618.
Griffin et al., Initial clinical study of indium-111-labeled clone 110 anticarcinoembryonic antigen antibody in patients with colorectal cancer. J Clin Onc 1991, 9:631-640.
Gupta et al., Identification of selective inhibitors of cancer stem cells by high-throughput screening. Cell 2009, 138(4):645-659.
Hatfield et al., microRNA and stem cell function. Cell Tissue Res 2008, 331(1):57-66.
Houghten et al., Generation and use of synthetic peptide combinatorial libraries for basic research and drug discovery. Nature 1991, 354:84-86.
Houghten al., The use of synthetic peptide combinatorial libraries for the identification of bioactive peptides. Biotechniques 1992, 13:412-421.
Houghten, Peptide libraries: criteria and trends. Trends Genet. 1993, 9:235-239.
Hudson, Epithelial stem cells in human prostate growth and disease. Prostate Cancer Prostatic Dis 2004, 7:188-194.
Ibarra et al., A role for microRNAs in maintenance of mouse mammary epithelial progenitor cells. Genes Dev 2007, 21(24):3238-3243.
Irizarry et al, Exploration, normalization, and summaries of high density oligonucleotide array probe level data. Biostatistics (Oxford, England) 2003, 4:249-264.
Ji et al, Identification of microRNA-181 by genome-wide screening as a critical player in EpCAM-positive hepatic cancer stem cells. Hepatology 2009, 50(2):472-480.
Kalluri, EMT: when epithelial cells decide to become mesenchymal-like cells. J Clin Invest 2009, 119(6):1417-1419.
Kato et al., microRNAs: small molecules with big roles—C. elegans to human cancer. Biol Cell 2008, 100(2):71-81.
Keller et al., Defining the cellular precursors to human breast cancer. Proc Natl Acad Sci U S A 2012, 109:2772-2777.
Keller et al., Mapping the cellular and molecular heterogeneity of normal and malignant breast tissues and cultured cell lines. Breast Cancer Res 2010, 12:R87.

(56) References Cited

OTHER PUBLICATIONS

Korkaya et al., Regulation of mammary stem/progenitor cells by PTEN/Akt/beta-catenin signaling. PLoS Biol 2009, 7(6):e1000121.
Ku et al., Potent non-peptide fibrinogen receptor antagonists which present an alternative pharmacophore. J. Med. Chem. 1995, 38:9-12.
Kudo-Saito et al., Cancer metastasis is accelerated through immunosuppression during Snail-induced EMT of cancer cells. Cancer Cell 2009, 15(3):195-206.
Lam, Application of combinatorial library methods in cancer research and drug discovery, Anticancer Drug Des. 1997, 12:145-167.
Lam et al., A new type of synthetic peptide library for identifying ligand-binding activity, Nature 1991, 354:82-84.
Lauffer, Targeted relaxation enhancement agents for MRI. Magnetic Resonance in Medicine 1991, 22:339-342.
Lawson et al., Basal epithelial stem cells are efficient targets for prostate cancer initiation. Proc Natl Acad Sci U S A 2010, 107:2610-2615.
Lebl et al., One-bead-one-structure combinatorial libraries. Biopolymers 1995, 37:177-198.
Lewis et al., Conserved seed pairing, often flanked by adenosines, indicates that thousands of human genes are microRNA targets. Cell 2005, 120(1):15-20.
Li et al., Identification of pancreatic cancer stem cells. Cancer Res 2007, 67(3):1030-1037.
Li et al., Small RNA-mediated regulation of iPS cell generation. EMBO J 2011, 30(5):823-834.
Li et al., Intrinsic resistance of tumorigenic breast cancer cells to chemotherapy. J Natl Cancer Inst 2008, 100:672-679.
Lim et al., Aberrant luminal progenitors as the candidate target population for basal tumor development in BRCA1 mutation carriers. Nat Med 2009, 15(8):907-913.
Liu et al., The microRNA miR-34a inhibits prostate cancer stem cells and metastasis by directly repressing CD44. Nat Med 2011, 17(2):211-215.
Liu et al., BRCA1 regulates human mammary stem/progenitor cell fate. Proc Natl Acad Sci U S A 2008, 105:1680-1685.
Liu et al., Breast cancer stem cells are regulated by mesenchymal stem cells through cytokine networks. Cancer Res 2011, 71:614-624.
Liu et al., Hedgehog signaling and Bmi-1 regulate self-renewal of normal and malignant human mammary stem cells. Cancer Res 2006, 66:6063-6071.
Liu et al., MicroRNA93 regulates proliferation and differentiation of normal and malignant breast stem cells. PLoS Genet 2012, 8:e1002751.
Lowery et al., MicroRNAs as prognostic indicators and therapeutic targets: potential effect on breast cancer management. Clin Cancer Res 2008, 14(2):360-365.
Lund et al., Nuclear export of microRNA precursors. Science 2004, 303(5654):95-98.
Madden et al., Perspectives in Drug Discovery and Design 2, 269-282.
Mani et al., The epithelial-mesenchymal transition generates cells with properties of stem cells. Cell 2008, 133(4):704-715.
Neve et al., A collection of breast cancer cell lines for the study of functionally distinct cancer subtypes. Cancer Cell 2006, 10:515-527.
Ocana et al., Metastatic colonization requires the repression of the epithelial-mesenchymal transition inducer prrx1. Cancer Cell 2012, 22:709-724.
Phillips et al., The response of CD24(-/low)/CD44+ breast cancer-initiating cells to radiation. J Natl Cancer Inst 2006, 98(24):1777-1785.
Reya et al., Stem cells, cancer, and cancer stem cells. Nature 2001, 414(6859):105-111.
Scott et al., Searching for peptide ligands with an epitope library, Science 1990, 249:386-390.
Shafee et al., Cancer stem cells contribute to cisplatin resistance in Brca1/p53-mediated mouse mammary tumors. Cancer Res 2008, 68(9):3243-3250.
Shehata et al., Phenotypic and functional characterization of the luminal cell hierarchy of the mammary gland. Breast Cancer Res 2012, 14:R134.
Sheridan et al., CD44+/CD24— breast cancer cells exhibit enhanced invasive properties: an early step necessary for metastasis. Breast Cancer Res 2006, 8(5):R59.
Shimono et al., Downregulation of miRNA-200c links breast cancer stem cells with normal stem cells. Cell 2009, 138(3):592-603.
Shin et al., Functional roles of multiple feedback loops in extracellular signal-regulated kinase and Wnt signaling pathways that regulate epithelial-mesenchymal transition. Cancer Res 2010, 70(17):6715-6724.
Shipitsin et al., Molecular definition of breast tumor heterogeneity. Cancer Cell 2007, 11(3):259-273.
Silber et al., miR-124 and miR-137 inhibit proliferation of glioblastoma multiforme cells and induce differentiation of brain tumor stem cells. BMC Med 2008, 6:14.
Skvorstsova et al., Epithelial-to-mesenchymal transition and c-myc expression are the determinants of cetuximab-induced enhancement of squamous cell carcinoma radioresponse. Radiother Oncol 2010, 96(1):108-115.
Sumerdon et al., An optimized antibody-chelator conjugate for imaging of carcinoembryonic antigen with indium-111. Int J Rad Appl Instrum B. 1990, 17:247-254.
Tanei et al., Association of breast cancer stem cells identified by aldehyde dehydrogenase 1 expression with resistance to sequential Paclitaxel and epirubicin-based chemotherapy for breast cancers. Clin Cancer Res 2009, 15(12):4234-4241.
Thiery et al., Epithelial-mesenchymal transitions in development and disease. Cell 2009, 139(5):871-890.
Thiery, Epithelial-mesenchymal transitions in development and pathologies. Curr Opin Cell Biol 2003, 15(6):740-746.
Thompson et al., Carcinoma invasion and metastasis: a role for epithelial-mesenchymal transition? Cancer research 2005, 65(14):5991-5995.
Tsai et al., Spatiotemporal regulation of epithelial-mesenchymal transition is essential for squamous cell carcinoma metastasis. Cancer Cell 2012, 22:725-736.
Tsuji et al., Epithelial-mesenchymal transition induced by growth suppressor p12CDK2-AP1 promotes tumor cell local invasion but suppresses distant colony growth. Cancer Res 2008, 68:10377-10386.
Vaillant et al., Jekyll or Hyde: does Matrigel provide a more or less physiological environment in mammary repopulating assays? Breast Cancer Res 2011, 13:108.
Wang et al., A luminal epithelial stem cell that is a cell of origin for prostate cancer. Nature 2009, 461:495-500.
Weaver et al., Functional culture models to study mechanisms governing apoptosis in normal and malignant mammary epithelial cells. Journal of Mammary Gland Biology and Neoplasia 1999, 4:193-201.
Wiemer, The role of microRNAs in cancer: no small matter. Eur J Cancer 2007, 43(10):1529-1544.
Wu et al., Stabilization of snail by NF-kappaB is required for inflammation-induced cell migration and invasion. Cancer Cell 2009, 15(5):416-428.
Xu et al., TGF-beta-induced epithelial to mesenchymal transition. Cell Res 2009, 19(2):156-172.
Yang et al., Twist, a master regulator of morphogenesis, plays an essential role in tumor metastasis. Cell 2004, 117(7):927-939.
Yang et al., Direct regulation of TWIST by HIF-1alpha promotes metastasis. Nat Cell Biol 2008, 10(3):295-305.
Yates et al., Co-culturing human prostate carcinoma cells with hepatocytes leads to increased expression of E-cadherin. Br J Cancer 2007, 96(8):1246-1252.
Yu et al., Mir-30 reduction maintains self-renewal and inhibits apoptosis in breast tumor-initiating cells. Oncogene 2010, 29(29):4194-4204.
Yu et al., Let-7 regulates self renewal and tumorigenicity of breast cancer cells. Cell 2007, 131(6):1109-1123.
Zuckermann et al., Discovery of nanomolar ligands for 7-transmembrane G-protein-coupled receptors from a diverse N-(substituted)glycine peptoid library. J. Med. Chem. 1994, 37:2678-85.

* cited by examiner

FIG. 9

A. Mir-93 sequence (SEQ ID NO:1)

```
 1 ctgggggctc caaagtgctg ttcgtgcagg tagtgtgatt acccaaccta ctgctgagct
61 agcacttccc gagcccccgg
```

B. Mir-100 sequence (SEQ ID NO:2)

```
 1 cctgttgcca caaacccgta gatccgaact tgtggtatta gtccgcacaa gcttgtatct
61 ataggtatgt gtctgttagg
```

C. Mir-221 sequence (SEQ ID NO:3)

```
 1 tgaacatcca ggtctggggc atgaacctgg catacaatgt agatttctgt gttcgttagg
61 caacagctac attgtctgct gggtttcagg ctacctggaa acatgttctc
```

FIG. 10
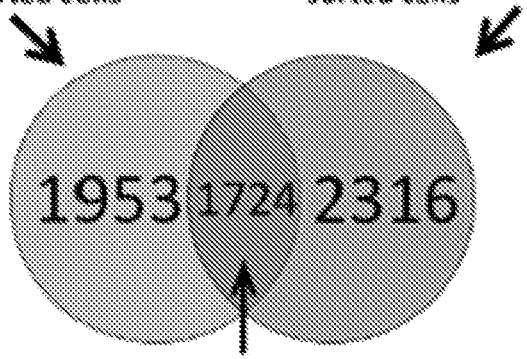
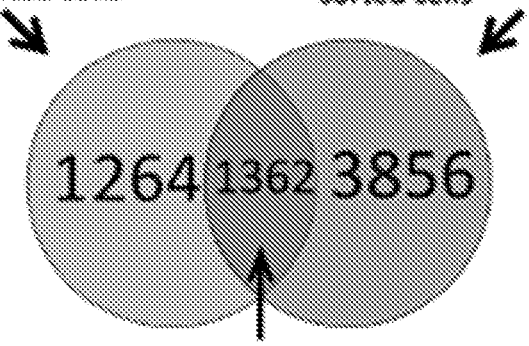

FIG. 10

| Probe ID | EMT/MET Markers | Symbol | CD24-CD44+/others fold change | ALDH+/ALDH- fold change |
|---|---|---|---|---|
| 1555938_x_at | vimentin | VIM | 1.40321 | -5.19337 |
| 201426_s_at | vimentin | VIM | 3.71553 | -1.9588 |
| 212758_s_at | ZEB1 | ZEB1 | 1.66559 | -2.56929 |
| 212764_at | ZEB1 | ZEB1 | 4.27922 | -3.05541 |
| 203603_s_at | ZEB2 | ZEB2 | 3.24387 | -2.80941 |
| 228333_at | ZEB2 | ZEB2 | 2.29699 | -1.55774 |
| 235593_at | ZEB2 | ZEB2 | 1.87898 | -2.72304 |
| 223679_at | beta-catenin | CTNNB1 | 1.56815 | -1.58219 |
| 203936_s_at | MMP9 | MMP9 | 1.50077 | -2.43914 |
| 201130_s_at | cadherin 1 | CDH1 | -1.1601 | 1.15386 |
| 201131_s_at | cadherin 1 | CDH1 | -6.15476 | 1.98536 |
| 209925_at | occludin | OCLN | -2.33365 | 1.49887 |
| 227492_at | occludin | OCLN | -3.82629 | 2.43622 |
| 231022_at | occludin | OCLN | -2.10499 | 1.46409 |
| 203953_s_at | claudin 3 | CLDN3 | -1.99331 | 3.77095 |
| 203954_x_at | claudin 3 | CLDN3 | -2.87954 | 2.68415 |
| 201428_at | claudin 4 | CLDN4 | -6.33721 | 2.51305 |
| 202790_at | claudin 7 | CLDN7 | -2.04657 | 2.13221 |
| 214598_at | claudin 8 | CLDN8 | -1.42979 | 1.85793 |
| 223249_at | claudin 12 | CLDN12 | -2.03103 | 2.40326 |
| 200606_at | desmoplakin | DSP | -7.93057 | 1.6892 |
| 224713_at | Ki-67 | MKI67IP | -1.17713 | 1.30328 |
| 224714_at | Ki-67 | MKI67IP | -1.53753 | 1.20219 |

FIG. 12

| ProbeID | EMT/MET Markers | Symbol | CD24-CD44+/others fold change | ALDH+/ALDH- fold change |
|---|---|---|---|---|
| 201426_s_at | vimentin | VIM | 2.12021 | -1.65066 |
| 210495_x_at | fibronectin 1 | FN1 | 2.51971 | -2.17374 |
| 211719_x_at | fibronectin 1 | FN1 | 4.02285 | -1.95158 |
| 212464_s_at | fibronectin 1 | FN1 | 3.06786 | -1.88834 |
| 214701_s_at | fibronectin 1 | FN1 | 3.96598 | -1.64108 |
| 216442_x_at | fibronectin 1 | FN1 | 2.84533 | -1.53689 |
| 213139_at | SNAI2 | SNAI2 | 1.39379 | -1.77536 |
| 212758_s_at | ZEB1 | ZEB1 | 1.63261 | -2.20459 |
| 212764_at | ZEB1 | ZEB1 | 2.22737 | -2.53499 |
| 239058_at | forkhead box C2 | FOXC2 | 1.29191 | -1.23305 |
| 201130_s_at | cadherin 1 | CDH1 | -2.36374 | 1.87365 |
| 201131_s_at | cadherin 1 | CDH1 | -1.51598 | 1.36827 |
| 209925_at | occludin | OCLN | -3.80494 | 3.92357 |
| 227492_at | occludin | OCLN | -2.38845 | 2.65517 |
| 231022_at | occludin | OCLN | -1.70214 | 1.58248 |
| 235937_at | occludin | OCLN | -1.63822 | 1.57234 |
| 218182_s_at | claudin 1 | CLDN1 | -1.51035 | 1.64136 |
| 222549_at | claudin 1 | CLDN1 | -1.49922 | 1.77932 |
| 1569421_at | claudin 4 | CLDN4 | -1.28954 | 1.56535 |
| 201428_at | claudin 4 | CLDN4 | -3.66665 | 3.70095 |
| 202790_at | claudin 7 | CLDN7 | -2.00752 | 1.73426 |
| 214598_at | claudin 8 | CLDN8 | -6.38394 | 7.00664 |
| 212020_s_at | Ki-67 | MKI67 | -1.28951 | 1.20873 |

| ProbeID | EMT/MET Markers | Symbol | CD24-CD44+/others fold change | ALDH+/ALDH- fold change |
|---|---|---|---|---|
| 203441_s_at | N-cadherin | CDH2 | 1.149 | -1.14961 |
| 200974_at | alpha smooth muscle actin | ACTA2 | 1.15441 | -1.83589 |
| 213260_at | forkhead box C1 | FOXC1 | 1.37732 | -1.58226 |
| 239058_at | forkhead box C2 | FOXC2 | 1.39094 | -1.21827 |
| 218182_s_at | claudin 1 | CLDN1 | -1.17484 | 2.02498 |
| 222549_at | claudin 1 | CLDN1 | -1.17812 | 1.70337 |
| 1569421_at | claudin 4 | CLDN4 | -1.25673 | 1.15956 |
| 201428_at | claudin 4 | CLDN4 | -1.68569 | 2.15574 |
| 214598_at | claudin 8 | CLDN8 | -1.5489 | 1.91828 |

B

| ProbeID | EMT/MET Markers | Symbol | CD24-CD44+/others fold change | ALDH+/ALDH- fold change |
|---|---|---|---|---|
| 1558199_at | fibronectin 1 | FN1 | 1.20023 | -1.75565 |
| 214702_at | fibronectin 1 | FN1 | 1.4235 | -1.39816 |
| 200974_at | alpha smooth muscle actin | ACTA2 | 1.29513 | -1.24175 |
| 213139_at | SNAI2 | SNAI2 | 2.07085 | -4.43426 |
| 202790_at | claudin 7 | CLDN7 | -1.24243 | 1.26207 |
| 214135_at | claudin 18 | CLDN18 | -1.44084 | 1.26204 |
| 1554812_at | claudin 20 | CLDN20 | -1.52742 | 1.3863 |

| ProbeID | EMT/MET Markers | Symbol | CD24-CD44+/others fold change | ALDH+/ALDH- fold change |
|---|---|---|---|---|
| 1555938_x_at | vimentin | VIM | 4.33383 | -1.4119 |
| 210495_x_at | fibronectin 1 | FN1 | 2.59095 | -2.07845 |
| 211719_x_at | fibronectin 1 | FN1 | 5.13476 | -3.33161 |
| 212464_s_at | fibronectin 1 | FN1 | 3.61182 | -1.4907 |
| 216442_x_at | fibronectin 1 | FN1 | 2.93974 | -2.13918 |
| 212758_s_at | ZEB1 | ZEB1 | 1.40123 | -2.76496 |
| 213943_at | TWIST1 | TWIST1 | 1.63652 | -5.08634 |
| 1566677_at | MMP2 | MMP2 | 1.35723 | -1.37622 |
| 201069_at | MMP2 | MMP2 | 1.25833 | -2.98593 |
| 203936_s_at | MMP9 | MMP9 | 1.23153 | -1.19986 |
| 201150_s_at | cadherin 1 | CDH1 | -1.52736 | 1.87357 |
| 209925_at | occludin | OCLN | -1.19424 | 1.69627 |
| 223509_at | claudin 2 | CLDN2 | -1.24984 | 1.16256 |
| 203953_s_at | claudin 3 | CLDN3 | -3.16807 | 1.56731 |
| 203954_x_at | claudin 3 | CLDN3 | -1.64922 | 1.79438 |
| 1569421_at | claudin 4 | CLDN4 | -1.64335 | 1.46229 |
| 202790_at | claudin 7 | CLDN7 | -1.51248 | 1.23789 |
| 206908_s_at | claudin 11 | CLDN11 | -1.39583 | 1.5345 |
| 232578_at | claudin 18 | CLDN18 | -1.54166 | 1.26895 |
| 212020_s_at | Ki-67 | MKI67 | -1.32108 | 1.18773 |
| 224714_at | Ki-67 | MKI67IP | -1.22021 | 1.22043 |

C

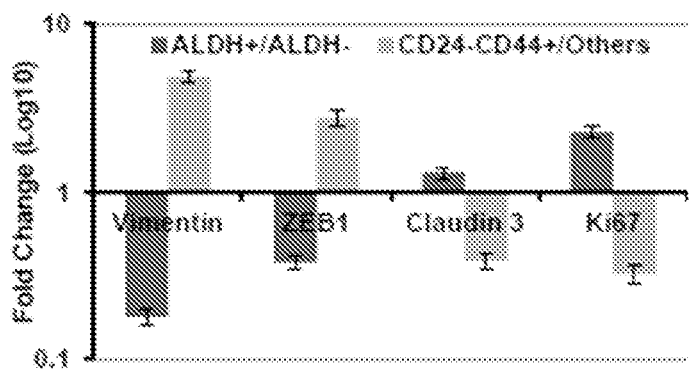

FIG. 21
EpCAM+CD49f+ALDH+
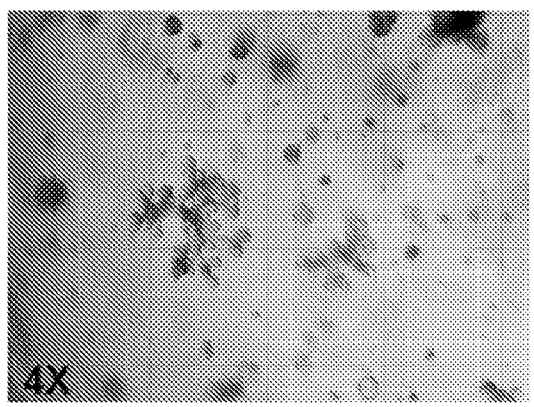
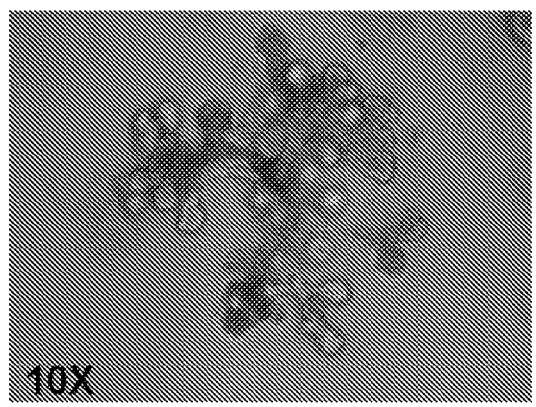
EpCAM+CD49f+ALDH−
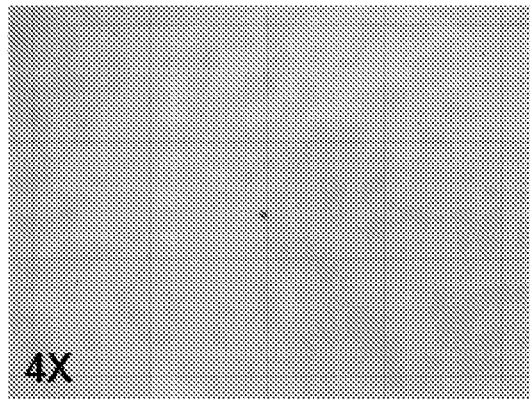
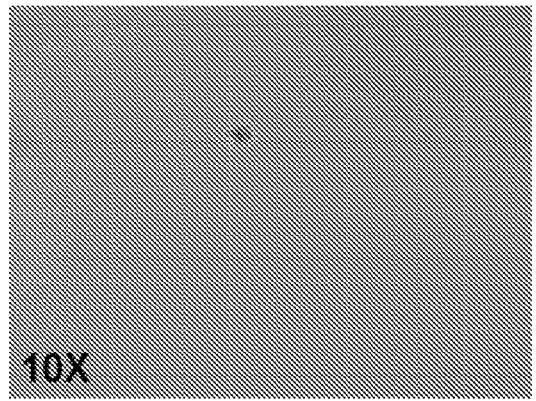

METHOD OF REDUCING THE NUMBER OF EMT AND MET TYPE BREAST CANCER STEM CELLS

The present application claims priority to U.S. Provisional application Ser. No. 61/596,796, filed Feb. 9, 2012, which is herein incorporated by reference in its entirety.

This invention was made with government support under CA66233 and CA101860 awarded by the National Institutes of Health. The government has certain rights in the invention.

FIELD OF THE INVENTION

The present invention relates to compositions, kits, and methods for therapeutic screening, diagnostics, and cancer treatment, based on the identification or use of the different states of cancer stem cells, including cancer stem cells in the EMT (epithelial to mesenchymal transition) MET (mesenchymal to epithelial transition), and EMT-MET states.

BACKGROUND OF THE INVENTION

With over 200,000 new cases yearly, breast cancer is the most common malignancy of women in the United States (US). The past 20 years have seen significant reductions in mortality from breast cancer in the United States and elsewhere. This reduction has been largely due to improvement in early detection and the development of more effective adjuvant therapies. Despite the fact that there have been significant advances in the treatment of breast cancer, the fact remains that once metastatic, the disease remains incurable. Recent studies have provided strong support for the cancer stem cell hypothesis which suggests that breast cancers are driven by a subpopulation of cells which display stem cell properties. These properties include self-renewal which generates other cancer stem cells and differentiation which generates populations of cells forming the bulk of the tumor. There is increasing evidence that cancer stem cells are resistant to chemotherapy and radiation therapy and, thus, contribute to treatment resistance and relapse.

The development of biomarkers to identify CSCs, as well as validation of in vitro and mouse models, has facilitated the isolation and characterization of these cells from both murine and human tumors. Breast cancer stems cells have been characterized by expression of the cell surface markers ESA and CD44 in the absence of expression of the marker CD24. These cells have been termed "breast cancer stem cells" (BCSCs). As few as 200 ESA-positive CD44+/CD24–lin– cells were able to generate tumors in immunocompromised NOD-SCID mice, whereas 100-fold more cells without these markers isolated from the same tumors were non-tumorigenic. Furthermore, the tumor-initiating populations regenerated tumors that recapitulated the heterogeneity of the initial tumor. The art has also developed an in vitro "mammosphere" assay as a means of quantitating normal and malignant stem cells. More recently, the art described the expression of aldehyde dehydrogenase (ALDH) as assessed by the Aldefluor assay (StemCell Technologies, Canada) or the isoform ALDH1 by immunohistochemistry (IHC) as a means of further identifying and enriching for tumor initiating CSC populations in human BCs. Interestingly, it was reported that these markers identify overlapping, but not identical cell populations. Furthermore, it has been found that these markers can be utilized to isolate CSC populations from established breast cancer cell lines, as well as primary tumor xenografts. The development and validation of breast cancer stem cell (BCSC) biomarkers, in vitro mammosphere formation assays, and xenograft models by the art has permitted assessment of chemotherapy and radiation resistance of BCSCs. These studies have demonstrated the relative resistance of BCSC to chemotherapy and radiation therapy. Furthermore, it has recently been demonstrated that the percent of BCSC as assessed either by CD44+/CD24 low mammosphere assays or by ALDH expression increases following neoadjuvant chemotherapy providing direct clinical evidence for the therapeutic resistance of BCSC. Together, these studies suggest that significant improvement in patient outcome will require the successful targeting of BCSCs.

SUMMARY OF THE INVENTION

The present invention relates to compositions, kits, and methods for therapeutic screening, diagnostics, and cancer treatment, based on the identification or use of the different states of cancer stem cells, including cancer stem cells in the EMT (epithelial to mesenchymal transition) MET (mesenchymal to epithelial transition), and EMT-MET states. In some embodiments, a subject is treated with one therapeutic that targets EMT cancer stem cells and a second therapeutic that targets MET cancers stem cells. In certain embodiments, the different states of cancer stem cells are distinguished based on markers $CD44^+CD24^-$, $EpCam^-CD49F^+$ (for EMT cancers stem cells), $ALDH^+$ (or ADLH1 isoform) and $EPCam^+CD49f^+$ (for MET cancers stem cells), and $CD44^+CD24^-ALDH^+$ (for EMT-MET cancer stem cells). In particular embodiments, micro RNAs are used to transition to one particular cancer stem cell type (e.g., mir-100 for EMT and mir-93 for MET).

In some embodiments, the present invention provides methods of reducing the frequency of EMT and MET type cancer stem cells in a subject with the EMT and MET type cancer stem (or a subject suspected of having EMT and MET type cancer stem cells) cells comprising co-administering to the subject an effective amount of: a) a first therapeutic agent directed against EMT type cancer stem cells, and b) a second therapeutic agent directed against MET type cancer stem cells, wherein the frequency of both the EMT and the MET type cancer stem cells in the subject are reduced (e.g., tumor size is reduced).

In other embodiments, the first therapeutic agent, targeting EMT cancer stem cells, comprises an inhibitor of a protein or nucleic acid encoding a protein selected from the group consisting of: IL-6 and an IL-6 pathway member (e.g., IL-6 antibody, IL-6R antibody, STAT3 inhibitor), Notch and a Notch pathway member (e.g., GSI), Wnt and Wnt pathway members, Hedgehog and Hedgehog pathway members, and Tgf-β and Tgf-β pathway members. In certain embodiments, the first therapeutic is an agent targeting Notch (e.g., U.S. Pat. No. 8,088,617; WO2008100563, WO2011088215, and WO20088091641, all of which are herein incorporated by reference); WNT (e.g., U.S. Pat. Pub. 20110305695 and WO2011088123, both of which are herein incorporated by reference), frizzled (e.g., WO2011123785 and WO2007142711, both of which are herein incorporated by reference in their entireties), jagged (e.g., WO2011063237 and WO2008140826, both of which are herein incorporated by reference in their entireties) and DLL4 (U.S. Pat. Pub. 20110165162, herein incorporated by reference in its entirety). In particular embodiments, the first therapeutic agent, targeting EMT cancer stem cells, is an antibody (or small molecule) being developed by Oncomed Pharmaceuticals selected from: Anti-DLL4 (OMP-21M18, demcizumab); Anti-DLL4/VEGF bispecific; Anti-Notch2/3 (OMP-59R5);

Anti-Notch1; Anti-Fzd7 (OMP-18R5); and Fzd8Fc. Information about these therapeutic agents can be found on Oncomed Pharmaceuticals web page.

In certain embodiments, the second therapeutic agent, targeting MET cancer stem cells, comprises a Pan-erb blocker (e.g., Canertinib dihydrochloride, Neratinib, JNJ-28871063, PF00299804, PD168393, HKI-272, NT-112, etc.) or a Her-2 pathway inhibitor (e.g., HERCEPTIN). In certain embodiments, the second therapeutic targets BMPR (e.g., WO2011116212, herein incorporated by reference in its entirety). In particular embodiments, the first or second therapeutic agent is a cancer stem cell targeting agent against: i) human mesenchymal-epithelial transition receptor binder (e.g., U.S. Pat. Pub. 20110142840, herein incorporated by reference in its entirety), ii) G-protein coupled receptor (LGR) (e.g., WO2009005809, herein incorporated by reference in its entirety), iii) integrin beta 1 (e.g., WO2009009114, herein incorporated by reference in its entirety), and iv) discoidin domain receptor 2 (e.g., WO2008070090, herein incorporated by reference in its entirety).

Any and all combinations of a specific EMT cancer stem cell targeting agent (such as those described above) and a specific MET cancer cell targeting agent (such as those described above) may be made and administered to a subject or packaged in a composition or kit. In certain embodiments, the first therapeutic agent is an IL6R antibody (e.g., tocilizumab) and the second therapeutic agent is anti-Her2 antibody (e.g., HERCEPTIN). Further, any and all combinations of first and second therapeutic agents may be co-administered with any additional bulk cancer killing agent, such as those described in Table 1 below. For example, a patient may be administered and IL6R antibody, an anti-HER2 antibody, and one or more compositions from Table 1.

In particular embodiments, the subject comprises bulk cancer cells that are not cancer stem cells, and wherein the method further comprises co-administering a third therapeutic agent to the subject, wherein the third therapeutic agent is capable of killing or inhibiting the bulk cancer cells, and wherein the frequency of the bulk cancer cells is reduced.

In certain embodiments, the EMT cancer stem cells are $CD44^+CD24^-$ and $EpCam^-CD49F^+$. In further embodiments, the EMT cancer stem cells express at least one of the following: vimentin, N-cadherin, slug, snail, and twist. In additional embodiments, the EMT cancer stem cells express miR-221 and/or miR-100. In particular embodiments, the MET cancer stem cells are $ALDH^+$ (or $ALDH1^+$) and $EpCam^+CD49F^+$. In further embodiments, the MET cancer stem cells express miR-93. In some embodiments, the subject further comprises EMT-MET cancer stem cells, and the co-administering reduces the frequency of the EMT-MET cancer stem cells in the subject. In other embodiments, the EMT-MET cancer stem cells are characterized as $CD44^+CD24^-$ and $ALDH^+$. In certain embodiments, the subject has a solid tumor and the solid tumor comprises the EMT and MET type cancer stem cells.

In some embodiments, the present invention provides compositions, systems, and kits for reducing the frequency of EMT and MET type cancer stem cells in a subject comprising: a) a first therapeutic agent directed against EMT type cancer stem cells (e.g., anti-IL6 receptor antibody), and b) a second therapeutic agent directed against MET type cancer stem cells (e.g., anti-HER2 antibody). In particular embodiments, the first therapeutic agent comprises a Pan-erb blocker or a Her-2 pathway inhibitor. In other embodiments, the second therapeutic agent comprises an inhibitor of a protein or nucleic acid encoding a protein selected from the group consisting of: IL-6, Notch, Wnt, Hedgehog, or Tgf-3. In additional embodiments, the kits, system, and compositions further comprise a third therapeutic agent capable of killing or inhibiting bulk cancer cells that are not cancer stem cells.

In certain embodiments, the present invention provides methods of identifying a test compound useful for treating EMT and/or MET type cancer stem cells: a) providing a population of cancer cells, wherein the majority (e.g., greater than 50% ... 65% ... 75% ... 90% ... 95% ... 99% ... 99.8%) of cancer cells in the population are a type of cancer cell or mixture of cancer cells selected from the group consisting of: i) EMT type cancer stem cells, ii) MET type cancer stem cells, iii) a mixture of EMT and MET cancer stem cells, and iv) EMT-MET cancer stem cells; and b) administering the test compound to the cancer cells; c)

monitoring the response of the cancer cells to the test compound; and d) identifying a test compound that inhibits the cancer cells.

In some embodiments, the methods further comprise screening the test compound identified in step d) against a population of normal cells and/or population of normal stem cells to determine if the test compound harms the normal cells and/or normal stem cells. In certain embodiments, the EMT cancer stem cells over-express miR-100 and/or miR-221 (e.g., forced over-expression via an expression vector). In certain embodiments, the MET cancer stem cells over-express miR-93. In additional embodiments, altering the cancer cells comprises inhibiting proliferation of the cancer cells. In further embodiments, altering the cancer cells comprises inhibiting survival of the cancer cells. In additional embodiment, the monitoring the response of the cells is selected from the group consisting of monitoring the proliferation of the cells; monitoring the survival of the cells; monitoring the cell cycle status of the cells; monitoring gene expression in the cells; monitoring protein expression and/or activity in the cells; and monitoring cellular pathways. In further embodiments, the monitoring gene expression identifies a cancer stem cell biomarker. In additional embodiments, the monitoring gene expression comprises use of a microarray. In some embodiments, the monitoring gene expression comprises measuring mRNA. In further embodiments, the monitoring cellular pathways comprises measuring the activity of the pathways.

In certain embodiments, the test compound is selected from a test compound library comprising a plurality of test compounds. In additional embodiments, the test compound library is selected from a test compound library comprising carbohydrates, monosaccharides, oligosaccharides, polysaccharides, amino acids, peptides, oligopeptides, polypeptides, proteins, nucleosides, nucleotides, oligonucleotides, polynucleotides, lipids, retinoids, drugs, antibodies, prodrugs, steroids, glycopeptides, glycoproteins, proteoglycans, and synthetic small molecule organic compounds.

In some embodiments, the present invention provides methods comprising: assaying a sample from a subject with cancer and identifying the presence or absence of EMT, MET, and/or EMT-MET cancer stem cells in the sample. In certain embodiments, the presence of EMT cancer stem cells are identified in the sample, and wherein the method further comprises administering a therapeutic to the subject directed to EMT cancer stem cells. In additional embodiments, the presence of MET cancer stem cells are identified in the sample, and wherein the method further comprises administering a therapeutic to the subject directed to MET cancer stem cells. In further embodiments, the presence of both EMT and MET cancer stem cells, and/or the presence of EMT-MET cancer stem cells, are identified in the sample, and wherein the method further comprises administering a first therapeutic to the subject directed to EMT cancer stem cells and a second therapeutic to the subject directed to MET cancer stem cells.

In particular embodiments, the EMT cancer stem cells are identified based on being CD44$^+$CD24$^-$ and EpCam$^-$CD49F$^+$. In further embodiments, the MET cancer stem cells are identified based on being ALDH$^+$ and EpCam$^+$CD49F$^+$. In certain embodiments, the EMT cancer stem cells are identified based on expression of miR-100 and/or miR-221. In particular embodiments, the MET cancer stem cells are identified based on expression of miR-93. In some embodiments, the identifying comprises viewing results of an assay performed on a sample from the subject which shows which type or types of cancer stem cells are present.

In some embodiments, the present invention provides compositions comprising: an isolated cancer stem cell over-expressing miR-93, miR-100, and/or miR-221. In certain embodiments, the cancer stem cell comprises an expression vector configured for expressing miR-93, miR-100, and/or miR-221.

In additional embodiments, the present invention provides methods comprising:

administering a composition to a subject, wherein the subject has cancer, and wherein the composition comprises an expression vector configured to express miR-93, miR-100, and/or miR-221.

In some embodiments, the present invention provides methods of converting a cancer stem cell from one type to another comprising: i) contacting a MET cancer stem cell with an miR-100, miR-9, and/or miR-221 expression vector such that miR-100, miR-9 and/or miR-221 is over expressed by said MET cancer stem cell thereby converting said MET cancer stem cell to a EMT cancer stem cell; and/or ii) contacting an EMT cancer stem cell with a miR-93, miR-200, and/or miR-205 expression vector such that miR-93, miR-200, and/or miR-205 is over expressed by said EMT cancer stem cell thereby converting said EMT cancer stem cell to a MET cancer stem cell.

In certain embodiments, the EMT cancer cells are identified by detecting elevated expression, and/or MET cancer stem cells are identified by detecting decreased expression, of at least one of the following markers: vimentin, N-cadherin, slug, snail, ZEB1, ZEB2, CTNNB1, MMP2, MMP9, FOXC1, FOXC2, Fibronectin 1, and twist. In other embodiments, the MET cancer cells are identified by detecting elevated expression, and/or EMT cancer cells are identified by detecting decreased expression of, of at least one of the following markers: EpCam, E-cadherin, occludin, desmoplakin, Ki67, cadherin 1, or a claudin.

In particular embodiments, the present invention provides methods of treating cancer in a subject comprising: treating a subject with antigen presenting cells such that at least some cancer cells in the subject are killed, wherein the antigen presenting cells have been exposed to: i) EMT and MET cancer stem cells or at least an antigenic portion of the EMT and MET cancer stem cells; and/or ii) EMT-MET cancer stem cells or at least an antigenic portion of the EMT-MET cancer stem cells.

In particular embodiments, the antigen presenting cells have been exposed to a lysate from the EMT and MET cancer stem cells, and/or the EMT-MET cancer stem cells. In particular embodiments, the antigen presenting cells comprise dendritic cells. In further embodiments, the antigen presenting cells comprise macrophages. In additional embodiments, the antigen presenting cells comprise B-cells. In some embodiments, the subject is a human. In certain embodiments, the subject has a cancer selected from the group consisting of: melanoma, breast cancer, prostate cancer, pancreatic cancer, lung cancer, liver cancer, brain cancer, skin cancer, and colon cancer. In particular embodiments, the methods further comprise treating the subject with a chemotherapeutic agent. In some embodiments, the methods further comprise treating the subject with one therapeutic that targets EMT cancer stem cells and a second therapeutic that targets MET cancers stem cells. In additional embodiments, the methods further comprise treating the subject with radiation therapy.

In some embodiments, the present invention provides compositions, systems, and kits comprising: antigen presenting cells that have been exposed to: i) EMT and MET cancer stem cells or at least an antigenic portion of said EMT and MET cancer stem cells; and/or ii) EMT-MET cancer stem cells or at least an antigenic portion of said EMT-MET cancer stem cells. In further embodiments, the compositions, systems, and kits further comprise at least one component selected from: i) a device configured to emit radiation used during external radiation cancer therapy; ii) a chemotherapeutic agent; iii) a first therapeutic that targets EMT cancer stem cells (e.g., as described herein); and iv) a second therapeutic that targets MET cancer stem cells (e.g., as described herein).

DESCRIPTION OF THE DRAWINGS

FIG. 9A shows the nucleic acid sequence of miR-93 (SEQ ID NO:1), FIG. 9B shows the nucleic acid sequence of miR-100 (SEQ ID NO:2), and FIG. 9C shows the nucleic acid sequence of miR-221 (SEQ ID NO:3).

FIG. 16 shows EMT/MET marker expression obtained with Affymatrix array Hu133 plus2.0. (A) Expression of EMT/MET markers in CD24–CD44+ vs. others and ALDH+ vs. ALDH– of SUM149 cell line. (B) Expression of EMT/MET markers in CD24–CD44+ vs. others and ALDH+ vs. ALDH– of primary xenograft MC1.

FIG. 21 shows results regarding evaluation of the branching morphogenesis of Lin−EpCAM+CD49f+ALDH+ cells and Lin−EpCAM+CD49f+ALDH− cells isolated from normal breast tissue. Primary cells isolated from reduction mammoplasties were immunostained with Lineage markers (Lin−), EpCAM and CD49f antibodies, and were subsequently stained with ALDEFLUOR. The cells were first gated based on viability (DAPI−) and lineage markers. The sorted cells (Lin−EpCAM+CD49f+ALDH+ cells and Lin−EpCAM+CD49f+ALDH-cells) were grown in 3D Matrigelfor 3 weeks.

DEFINITIONS

Figure 1:
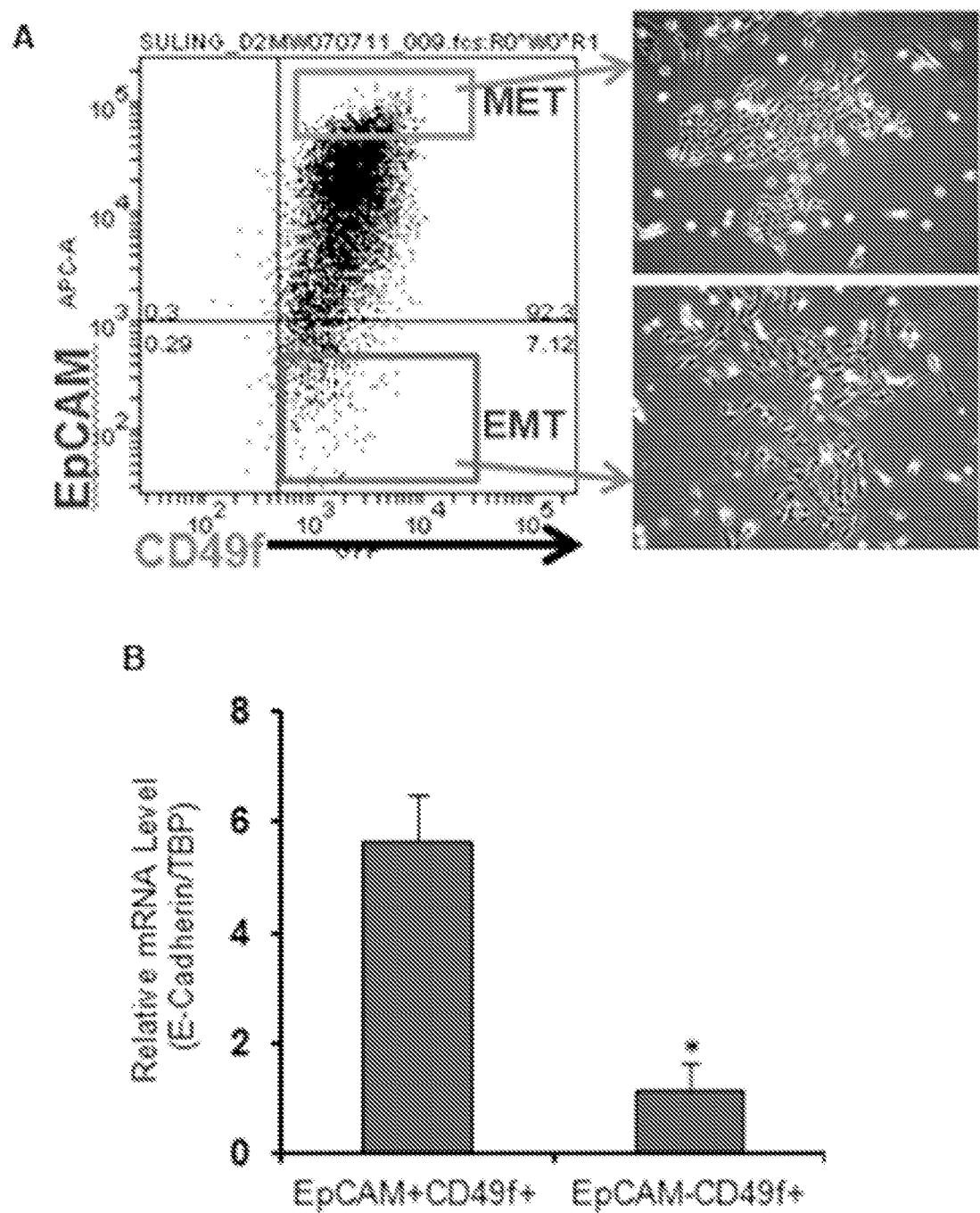
FIG. 1 shows a characterization of EMT and MET cells as described in Example 1. EpCAM$^+$CD49f$^+$ cells and EpCAM$^-$CD49f$^+$ cells were sorted by flow cytometry (A). 200k cells were plated in T25 flasks and phase micrographs were shown in (A). Total RNA was isolated from the sorted cells right after sorting and the expression MET marker (B) and EMT markers (C) were measured by qRT-PCR in both cell populations.
Figure 1:
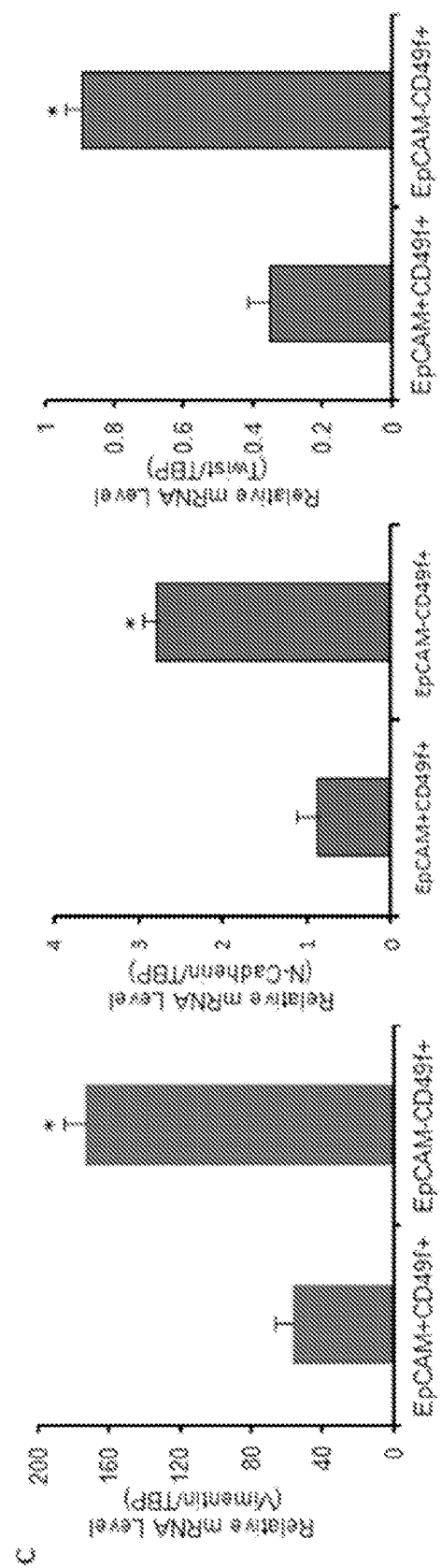

As used herein, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

As used herein, the term "subject is suspected of having cancer" refers to a subject that presents one or more signs or symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "cancer cells" refers to individual cells of a cancer. Such cells may include, for example, tumorigenic cells (e.g., capable of generating a tumor), leukemogenic cells (e.g., capable of generating leukemia), cancer stem cells (e.g., capable of forming new tumors or transferring disease upon transplantation into an immunocompromised host), as well as cells that are not tumorigenic, leukemogenic or that are capable of forming new tumors or transferring disease upon transplantation (e.g., mesenchymal and endothelial cells).

As used herein, the term "characterizing tissue in a subject" refers to the identification of one or more properties of a tissue sample (e.g., including but not limited to, the presence of EMT or MET cancer stem cells in the tissue).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Co-administration" refers to administration of more than one chemical agent or therapeutic treatment (e.g., radiation therapy) to a physiological system (e.g., a subject or in vivo, in vitro, or ex vivo cells, tissues, and organs). "Co-administration" of the respective chemical agents and therapeutic treatments (e.g., radiation therapy) may be concurrent, or in any temporal order or physical combination.

"Enriched," as in an enriched population of cells, can be defined based upon the increased number of cells having a particular marker in a fractionated set of cells as compared with the number of cells having the marker in the unfractionated set of cells. However, the term "enriched" can also be defined by tumorigenic function as the minimum number of cells that generate a cancer (e.g., a tumor) at a limited dilution frequency (e.g., in a mouse model). For example, if 500 cancer stem cells form tumors in 63% of test animals, but 5000 unfractionated tumor cells are required to form tumors in 63% of test animals, then the cancer stem cell population is 10-fold enriched for tumorigenic activity.

The terms "test compound" and "candidate compound" refer to any chemical entity, pharmaceutical, drug, and the like that is a candidate for use to treat or prevent a disease, illness, sickness, or disorder of bodily function (e.g., cancer (e.g., tumorigenic cells, leukemogenic cells or cancer stem cells)). Test compounds comprise both known and potential therapeutic compounds. A test compound can be determined to be therapeutic by screening using the screening methods of the present invention. Examples of test compounds include, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, drug, antibody, prodrug, glycopeptides, glycoproteins, proteoglycans and the like, and synthetic analogues or derivatives thereof, including peptidomimetics, small molecule organic compounds and the like, and mixtures thereof (e.g., that is a candidate for use to treat or prevent a disease, illness, sickness, or disorder of bodily function (e.g., cancer (e.g., tumorigenic cells, leukemogenic cells or cancer stem cell growth)). Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are anticancer agents. In particularly preferred embodiments, "test compounds" are anticancer agents that induce apoptosis in cells.

As used herein, the term "test compound library" refers to a mixture or collection of one or more compounds generated or obtained in any manner. Preferably, the library contains more than one compound or member. The test compound libraries employed in this invention may be prepared or obtained by any means including, but not limited to, combinatorial chemistry techniques, fermentation methods, plant and cellular extraction procedures and the like. Methods for making combinatorial libraries are well-known in the art (See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Each of these references is incorporated herein by reference in its entirety).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like.

DETAILED DESCRIPTION OF THE INVENTION

The present invention relates to compositions, kits, and methods for therapeutic screening, diagnostics, and cancer treatment, based on the identification or use of the different states of cancer stem cells, including cancer stem cells in the EMT (epithelial to mesenchymal transition) MET (mesenchymal to epithelial transition), and EMT-MET states. In some embodiments, a subject is treated with one therapeutic that targets EMT cancer stem cells and a second therapeutic that targets MET cancers stem cells. In certain embodiments, the different states of cancer stem cells are distinguished based on markers $CD44^+CD24^-$, $EpCam^-CD49F^+$ (for EMT cancers stem cells), $ALDH^+$ and $EPCam^+CD49f^+$ (for MET cancers stem cells), and $CD44^+CD24^-ALDH^+$ (for EMT-MET cancer stem cells). In particular embodiments, micro RNAs are used to transition to one particular cancer stem cell type (e.g., mir-100 for EMT and mir-93 for MET).

There is increasing evidence that many human cancers, including breast cancer, are driven and maintained by cancer stem cells (CSCs) which mediate tumor metastasis and contribute to treatment resistance and relapse. The art described "breast cancer stem cells" (BCSCs) characterized by expression of the cell surface markers ESA and CD44 and the absence of expression of the marker CD24. More recently, it was demonstrated that breast cancer cells contain subpopulations with stem cell properties that can be isolated by virtue of their expression of Aldehyde dehydrogenase (ALDH) as assessed by the Aldefluor assay. Interestingly, these markers identify overlapping, but not identical cell populations.

Work conducted during development of embodiments of the present invention suggest that both normal and malignant breast stem cells exist in distinct, inter-convertible states (EMT and MET), the inter-conversion of which is regulated by microRNAs. EMT CSCs have a mesenchymal morphology, are largely quiescent, invasive and characterized by expression of the CSC markers $CD24^-CD44^+$ and are $EpCAM-CD49f^+$. In contrast, the MET (mesenchymal epithelial transition) state of CSCs is characterized by active self-renewal and expression of the CSC markers ALDH and $EpCAM^+CD49F^+$. A subpopulation of cells expressing both $CD24^-CD44^+$ and ALDH may represent cells in transition between these states. While not important to understand and practice the present invention and not limiting the present invention, it is believed that this transition is regulated by signals originating in the microenvironment which in turn modulate microRNA networks in the CSC populations. The existence of multiple stem cell states suggests the necessity of developing therapeutic strategies capable of effectively targeting CSCs in all of these states. In addition, since CSC states are regulated by miRNAs, these small non-coding RNAs may be useful therapeutic agents to target CSCs.

Until recently, the function of non-coding regions of the genome was unknown. However, it is now clear that many of these regions code for microRNAs. Each microRNA is capable of regulating the expression of multiple proteins and as a result, can have very potent effects on cellular functions.

The miRNA gene is first transcribed by RNA polymerase II into a primary transcript (pri-miRNA) in the nucleus, where the hairpin stem-loop structure is processed into precursor miRNA (pre-miRNA) by a microprocessing complex, which includes Drosha and DGCR8. The 60-70 nt-long pre-miR-NAs is exported from the nucleus. Within the cytoplasm, the RNAse III enzyme Dicer processes the pre-miRNA to yield the 18-25 nt mature miRNAs which mediate gene silencing through imperfect hybridization to 3' untranslated regions (3' UTR) in target mRNAs by modulating and modulate a variety of cellular processes including regulating m-RNA stability and proliferation, differentiation translation, microRNAs and apoptosis.

Work conducted during development of embodiments of the present invention determined that microRNAs regulate cancer stem cells (CSCs). Recent studies have demonstrated a link between dysregulated expression of miRNAs and carcinogenesis. A number of miRNAs have been shown to function as oncogenes or tumor suppressors during carcinogenesis. In addition, emerging evidence suggests that miRNAs also play essential roles in stem cell self-renewal and differentiation by negatively regulating the expression of key stem cell regulating genes. Furthermore, abnormal miRNA expression may result in dysregulation of self-renewal in cancer stem cells during cancer progression. Silber et al reported that mir124 and mir137 induce differentiation of neural and glioblastoma stem cells and induce cell cycle arrest. These results suggest that targeted delivery of mir124 and mir137 to glioblastoma cells may be therapeutically efficacious for the glioblastoma treatment. miRNA181 and miRNA17-92 clusters were shown to be up-regulated in hepatocellular carcinoma (HCC) CSCs. More recently, Tang's group showed that prostate cancer stem and/or progenitor cell populations have lower levels of miR-34a and let-7b compared to bulk tumor cells. In addition, they reported that miR34a targets CD44, resulting in impaired tumor growth and decreased metastases in mouse models of prostate cancer. The increased survival of mice treated with systemically delivered miR34a suggests a novel strategy to target prostate CSCs, thereby inhibiting tumor growth and metastasis.

There have been a number of studies describing a role of microRNA in the regulation of normal and malignant breast stem cells. Hannon's group showed that both mir-205 and mir-22 are highly expressed in mouse mammary stem/progenitor cells whereas mir-93 and Let7 are depleted in this population. Rosen's group reported that miR-205 overexpression in mouse mammary cells led to an expansion of the progenitor cell population, decreased cell size and increased cellular proliferation. More recent studies have shown that overexpression of mir-200c reduced the clonogenic and tumor-initiation activities of BCSCs and suppressed mammary duct formation by normal mammary stem cells. This occurred through the down-regulation of the polycomb gene Bmi-1, a target of mir-200c. This work demonstrated a molecular link between normal breast stem cells and BCSCs. Yu et al showed that Let7 is decreased in BCSCs and that overexpression of Let7 inhibits the cell proliferation, mammosphere formation, BCSC self-renewal and differentiation, and tumor formation and metastasis in NOD/SCID mice. These effects were shown to be mediated through down-regulation of the Let7 targets H-Ras and HMGA2. This group also demonstrated that expression of miR-30 markedly reduced BCSCs by targeting ubiquitin-conjugating enzyme 9 (UBC9) and integrin b3 (ITGB3). More complete inhibition of self-renewal and mammosphere formation of BCSCs was observed when both Let7 and miR-30 were simultaneously introduced compared to each microRNA individually. The ability of these microRNAs to target BCSCs suggests that they may have significant therapeutic potential.

Epithelial to mesenchymal transition (EMT) is involved in many biological processes including embryonic development, wound healing and cancer progression. During EMT, epithelial cells lose cell-cell contacts and undergo cytoskeletal remodeling and polarity changes, resulting in acquisition of a mesenchymal morphology as well as enhanced migratory ability. Importantly, EMT is reversible and these cells can undergo a mesenchymal to epithelial transition (MET), so that polarized epithelium can be generated at a new site. Both EMT and MET play central roles in embryogenesis. During development, the process of epithelial-mesenchymal transition (EMT) is required for tissue and organ formation. The EMT state has been associated with loss of epithelial characteristics including apical basal polarity and expression of E-Cadherin and acquisition of mesenchymal characteristics including loss of polarity and increased expression of the transcription factors slug, snail and twist and mesenchymal proteins including vimentin and fibronectin. During early embryonic development, the mesoderm generated by EMTs develops into multiple tissue types, and later in development, mesodermal cells generate epithelial organs (e.g., kidney and ovary) by METs. In adult tissues, TGF-β can induce EMT characterized by downregulation of epithelial markers such as E-cadherin and upregulation of EMT-inducing factors, such as Twist and Snail. It has been proposed that EMT plays an important role in tumorigenesis and progression. Furthermore, a number of developmental pathways such as the Wnt and HGF-cMet pathways which are frequently deregulated in cancers are also regulators of EMT. Both the inflammatory immune response and the hypoxic tumor environment induce EMT in cancers. It is increasingly recognized that EMT plays an important role in the metastasis of breast cancer and other types of carcinoma. EMT has also been implicated in therapeutic resistance and tumor recurrence. Since EMT is a key developmental program that is often activated during cancer invasion and metastasis, and CSCs that maintain and initiate tumors have also been implicated in invasion and metastasis, the relationship between EMT and CSCs is an important question.

A defining characteristic of CSCs is their ability to self-renew, a property that endows these cells with the ability to initiate and sustain tumor growth. However, although the EMT state has been linked to tumor invasion and metastasis, EMT cells are largely quiescent. The differences in invasive and proliferative characteristics of CSCs and EMT cells has led to the proposition that CSCs and EMTs are mutually exclusive.

Recently it has been suggested that expression of the cell surface markers EpCAM and CD49f can be used to define functional populations of normal mouse and human mammary cells. Based on in vitro and mouse fat pad re-implantation studies it has been suggested that EpCAM−CD49f$^+$ cells represent mammary stem cells, EpCAM$^+$CD49$^+$ (double-positive cells): luminal progenitors; EpCAM$^+$CD49f$^−$: epithelial cells; and EpCAM$^−$CD49f: stromal cells. However, double-positive (EpCAM$^+$CD49f$^+$) so-called luminal progenitor cells, have been found to give rise to basal as well as luminal cells when cultured in vitro. Furthermore, it has recently been reported that both the EpCAM$^−$CD49f$^+$ and EpCAM$^+$CD49f$^+$ fractions of normal human mammary cells have the ability to form complete mammary trees consisting of basal as well as luminal cells when transplanted into the fat pads of immunosuppressed mice, which have been "humanized" with normal mammary fibroblasts. These results suggest that in addition to luminal progenitors, the EpCAM⁺CD49f⁺ population may also contain a sub-population with stem cell characteristics.

Figure 7:
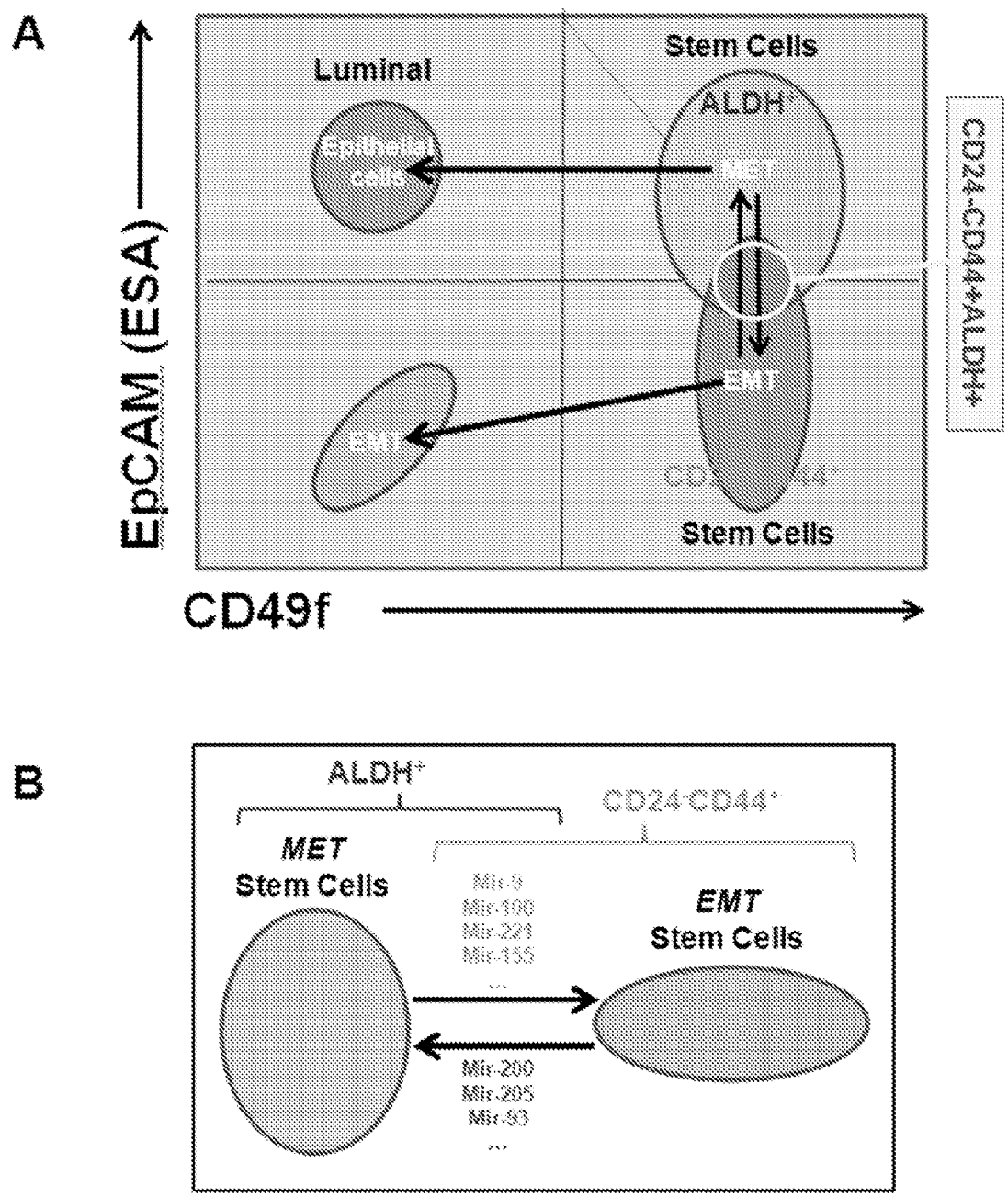
FIG. 7A shows a non-limiting model in which breast cancer stem cells (BCSCs) can exist in two alternative states: one, an EMT state which is EpCAM$^-$CD49f$^+$ expresses the stem cell markers CD24$^-$CD44$^+$, and an MET population which is EpCAM$^+$CD49f$^+$ (double-positive) and expresses the CSC marker ALDH.
FIG. 7B shows the two stem cell states are interconvertable, which is regulated by the microRNA networks. Such as: mir-9, mir-100, mir-221 and mir-155 can induce EMT stem cells; mir-200, mir-205 and mir-93 can induce MET stem cells.

As described previously, CD24⁻CD44⁺ and ALDH identify overlapping, but not identical cell populations. Work conducted during the development of embodiments of the present invention generated data indicating that EpCAM⁺CD49f⁺ cells (MET) contain an ALDH enriched population, whereas CD24⁻CD44⁺ cells are mainly contained in EpCAM⁻CD49f⁺ population (EMT). These results suggest a model in which breast cancer stem cells can exist in two alternative states: one, an EMT state which is EpCAM⁻CD49f⁺ expresses the stem cell markers CD24⁻CD44⁺, and an MET population which is EpCAM⁺CD49f⁺ (double-positive) and expresses the CSC marker ALDH (FIG. 7A).

There is substantial evidence linking BCSCs and EMT. BCSCs isolated from primary breast tumors and metastatic pleural effusions express EMT markers. However, there is less evidence linking BCSCs and MET. Consistent with the expression of EMT markers by BCSCs, these cells also express EMT related microRNAs. miRNA expression profiling of BCSCs isolated from human breast tumors compared to the remaining breast cancer cells revealed high levels of expression of EMT-inducing miR-155. Furthermore, mir-200 which is downregulated in BCSCs is associated with MET.

Work conducted during the development of embodiments of the present invention demonstrated that the double-positive EpCAM⁺CD49f⁺ population is characterized by the highest expression of mir-93 and that forced overexpression of mir-93 increases the proportion of EpCAM⁺CD49f⁺ and ALDH⁺ cells in non-transformed MCF-10A cells as well as primary normal human mammary cells isolated from reduction mammoplasty specimens. Furthermore, it was demonstrated that expression levels of mir-221 and mir-100 are significantly higher in EpCAM⁻CD49f⁺ and EpCAM⁻CD49f⁻ populations than in EpCAM⁺CD49f⁺ and EpCAM⁺CD49f⁻ populations. Furthermore, forced over-expression of mir-100 or mir-221 increased the proportion of EpCAM⁻CD49f⁺ cells in non-transformed MCF-10A cells as well as primary normal human mammary cells isolated from reduction mammoplasty specimens. This resulted in an increase in the proportion of CD24⁻/CD44⁺ CSC cells with a concomitant decrease in the ALDH⁺ CSC population. These results indicate that mir-93, mir-100 and mir-221 are important regulators of the transition between the EMT and MET stem cell states. It was demonstrated that induction of mir-93 in EMT SUM159 cells induces an MET in the ALDH-positive CSC population characterized by increased expression of E-Cadherin and Claudin, and down-regulation of mesenchymal genes, such as vimentin, N-Cadherin and Twist. It was found that mir-93 also inhibits TGFβ signaling by targeting TGFβR2, an effect seen within twelve hours of mir-93 induction. This was followed by an EMT/MET transition in the Aldefluor-positive CSC population. Since TGFβ is a major regulator of EMT, abrogation of this signaling pathway may facilitate MET.

Of interest, it has been recently reported that the mir106b-25 cluster including mir-93 is induced in the early stages of nuclear reprogramming of fibroblasts into IPS cells. This is accompanied by an EMT to MET conversion in these cells which is obligatory for reprogramming to occur. This suggests that this miRNA cluster may regulate EMT to MET in multiple biological contexts. Furthermore, expression of mir-100 or mir-221 in MCF10A cells and several cancer cell lines resulted in a decrease of the ALDH-positive CSC population with a concomitant increase in the CD24⁻CD44⁺ population accompanied by induction of EMT. Work conducted during development of embodiments of the present invention demonstrated mir-100 effects are mediated by targeting BMPR2, SMARCA5 and SMARCD1, all of which may contribute to induction of EMT.

The existence of reversible alternative states of CSCs provides an explanation for the seemingly disparate hypothesis concerning the relationship between CSCs and EMT. While the present invention is not limited to any particular mechanism and an understanding of the mechanism is not necessary to practice the present invention, it is believed that CSCs may exist in either EMT or MET states, the inter-conversion of which is regulated by the microenvironment which in turn regulates CSC microRNA networks as illustrated in FIG. 7B. The existence of alternative CSC states provides an explanation for how these cells promote tumor invasion as well as growth at metastatic sites. For example, it has been shown that bladder cancer cells selected for bone metastatic competence are overtly epithelial as compared to their parental cell. Similarly, human breast cancer, liver, lung and brain metastasis often express more E-cadherin than their corresponding primary tumors.

Figure 8:
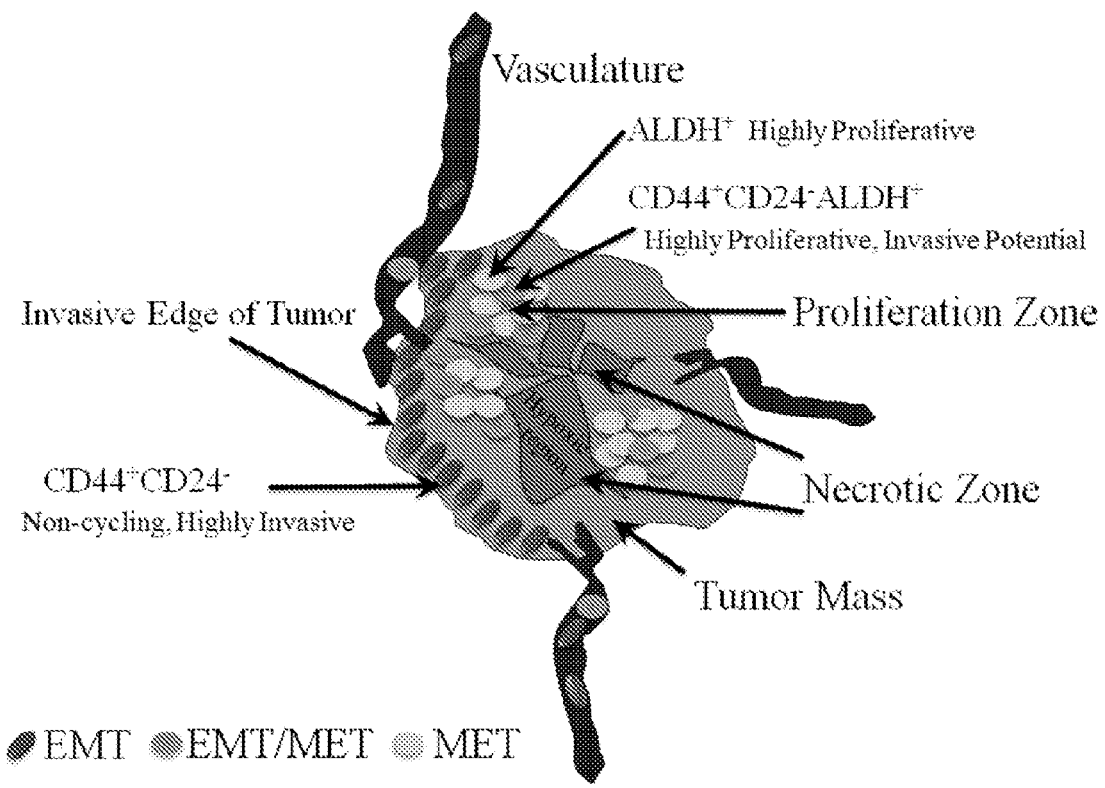
FIG. 8 shows a non-limiting hypothetical model in which CSCs located inside the tumor mass exist predominantly in the MET state in which they are highly proliferative and express ALDH (ALDH$^+$), in contrast at the tumor invasive front are located with EMT CSCs which are characterized as CD24$^-$CD44$^+$ and are highly invasive, and mediates tumor invasion and metastasis. The intermediate CSCs (CD24$^-$CD44$^+$ALDH$^+$) also reside inside the tumor mass, and they are highly proliferative with invasive potential.

Again, while the present invention is not limited to any particular mechanism and an understanding of the mechanism is not necessary to use the present invention, a hypothetical model is proposed (FIG. 8) in which CSCs located inside the tumor mass exist predominantly in the MET state in which they are highly proliferative and express ALDH, in contrast at the tumor invasive front, factors such as TGF-β in the microenvironment induce EMT in the CSC populations. The population which is characterized as CD24⁻CD44⁺ is highly invasive and mediates tumor invasion and metastasis. The association of EMT and invasion is supported by studies demonstrating that down-regulation of mir-93 using a mirZIP vector or upregulation of mir-100 increases the invasiveness of cancer cells. Highly invasive EMT/CSCs enter the circulation and travel to distant organs where they form micrometastasis. This scenario is supported by studies showing that in women with breast cancer, bone micrometastasis express CSC markers such as CD24⁻CD44⁺ as well as EMT markers such as vimentin. These micrometastasis are largely quiescent as indicated by their lack of expression of markers of cellular proliferation such as Ki67. In order to enter a proliferative state, EMT/CSC cells undergo an MET transition in which they lose their invasive characteristics and acquire self-renewal capacity. Self-renewing MET/CSCs in turn drive tumor growth at metastatic sites. In this hypothetical model, the balance of EMT/MET states of CSCs regulated by miRNAs plays an important role in mediating tumor invasion and metastasis, as well as maintaining tumor dormancy or promoting tumor growth at metastatic sites.

The ability of CSCs to exist in alternative EMT and MET states, the transition of which is believed to be regulated by the microenvironment and mediated by miRNAs has important implications for understanding the role of the cells carcinogenesis, invasion and metastasis. In addition, the existence of alternative CSC states, associated with expression of different protein markers has important implications for understanding the plasticity of CSCs. For example, it has been claimed that CSCs may be generated from non-CSC tumor populations through induction of EMT. However, the existence of alternative CSC state suggests that the acquisition of stem cell markers may reflect transition of CSC states rather than generation of CSCs from non-CSC populations. In addition, the existence of multiple stem cell states suggests the necessity of developing therapeutic strategies capable of effectively targeting CSCs in all of these states. Dysregulation of microRNAs has been implicated in tumor development and microRNAs plays important roles in regulating cancer stem cells. Since CSCs have been shown to be involved in tumor initiation, tumor maintenance, metastasis, and therapeutic resistance, the regulation of microRNA networks in CSCs provides novel therapeutic targets.

The existence of multiple CSC states also has important therapeutic implications, since CSCs in these states may respond differently to therapeutic agents. Nevertheless, the complexity of regulatory pathways in CSCs, as well as the heterogeneity of these cell populations, suggests that it may be beneficial to combine multiple CSC-targeting agents to eliminate all CSC populations and thus improve the outcome for cancer patients.

The principles of normal stem cell biology have been applied to isolate and characterize cancer stem cells. Examples of cancers from which cancer stem cells can be isolated or enriched, and targeted, according to the present invention include, but are not limited to, lymphomas (e.g., Hodgkin's disease and non-Hodgkin's disease), leukemias (e.g., acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, and chronic lymphocytic leukemia), and sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma). The invention is also applicable to sarcomas and epithelial cancers, such as ovarian cancers and breast cancers, as well as to all solid tumors.

A subject's (e.g., a particular cancer patient's) cancer stem cells (e.g., once isolated and allowed to proliferate in vitro), can be analyzed and screened. For example, in some embodiments, analyzing a subject's cancer stem cells is used as a diagnostic for the subject (e.g., the identification of biomarkers present within the cancer cells can be used to provide to the subject a prognosis (e.g., of morbidity or mortality associated with the cancer, or, the likelihood of the cancer to respond to a therapeutic treatment).

Thus, in some embodiments, the present invention provides methods for detection of expression of cancer stem cell biomarkers to identify if the patient has EMT, MET, EMT-MET cancer stem cells or combinations thereof. In some embodiments, expression is measured directly (e.g., at the nucleic acid or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of biomarkers. In certain embodiments, the presence of a cancer stem cell biomarker is used to provide a prognosis to a subject. For example, the detection of a cancer stem cell biomarker in cancerous tissues may be indicative of a cancer that is or is not likely to metastasize. In addition, the expression level of a cancer stem cell biomarker may be indicative of a transformed cell, cancerous tissue or a cancer likely to metastasize.

The information (e.g., state of the cancer cells from a subject) provided can also be used to direct the course of treatment. For example, if a subject is found to possess or lack a cancer stem cell biomarker that is likely to metastasize, therapies can be chosen to optimize the response to treatment (e.g., for subjects with a high probability of possessing a metastatic cancer more aggressive forms of treatment can be used).

Cancer stem cell biomarkers identified as being up or down-regulated in cancer stem cells using the methods of the present invention are further characterized using microarray (e.g., nucleic acid or tissue microarray), immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of biomarkers. The panel allows for the simultaneous analysis of multiple biomarkers correlating with carcinogenesis, metastasis and/or angiogenesis associated with cancer. For example, a panel may include biomarkers identified as correlating with cancerous tissue, metastatic cancer, localized cancer that is likely to metastasize, pre-cancerous tissue that is likely to become cancerous, pre-cancerous tissue that is not likely to become cancerous, and cancerous tissues or cells likely or not likely to respond to treatment. Depending on the subject, panels may be analyzed alone or in combination in order to provide the best possible diagnosis and prognosis. Markers for inclusion on a panel are selected by screening for their predictive value using any suitable method. In certain embodiments, the panels contain reagents for detecting CD44, CD24, EpCam, CD49f, ALDH, mir-221, mir-110, and/or mir-93.

In some preferred embodiments, cancer stem cell biomarkers (e.g., including but not limited to, those disclosed herein) are detected by measuring the levels of the cancer stem cell biomarker in cells and tissue (e.g., cancer cells and tissues). For example, in some embodiments, a cancer stem cell biomarker are monitored using antibodies or by detecting a cancer stem cell biomarker protein/nucleic acid (e.g., CD44, CD24, EpCam, CD49f, ALDH, mir-221, mir-110, and/or mir-93). In some embodiments, detection is performed on cells or tissue after the cells or tissues are removed from the subject. In other embodiments, detection is performed by visualizing the cancer stem cell biomarker in cells and tissues residing within the subject.

In some preferred embodiments, cancer stem cell biomarker are detected by measuring the expression of corresponding mRNA in a tissue sample (e.g., cancerous tissue). In some embodiments, RNA is detected by Northern blot analysis. Northern blot analysis involves the separation of RNA and hybridization of a complementary labeled probe.

In still further embodiments, RNA (or corresponding cDNA) is detected by hybridization to a oligonucleotide probe. A variety of hybridization assays using a variety of technologies for hybridization and detection are available. For example, in some embodiments, a TaqMan assay (PE Biosystems, Foster City, Calif.; See e.g., U.S. Pat. Nos. 5,962, 233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In other embodiments, gene expression of a cancer stem cell biomarker is detected by measuring the expression of the corresponding protein or polypeptide. Protein expression may be detected by any suitable method. In some embodiments, proteins are detected by immunohistochemistry. In other embodiments, proteins are detected by their binding to an antibody raised against the protein.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized. In other embodiments, the immunoassay described in U.S. Pat. Nos. 5,599,677 and 5,672,480; each of which is herein incorporated by reference.

In yet other embodiments, the present invention provides kits for the detection and characterization of cancer stem cell biomarkers (e.g., CD44, CD24, EpCam, CD49f, ALDH, mir-221, mir-110, and/or mir-93). In some preferred embodiments, the kit contains cancer stem cells. In some embodiments, the kits contain antibodies specific for a cancer stem cell biomarker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

In some embodiments, in vivo imaging techniques are used to visualize the expression of a cancer stem cell biomarker in an animal (e.g., a human or non-human mammal). For example, in some embodiments, a cancer stem cell biomarker mRNA or protein is labeled using an labeled antibody specific for the cancer stem cell biomarker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer stem cell biomarkers of the present invention are described herein.

The in vivo imaging methods of the present invention are useful in the diagnosis of cancers that express a cancer stem cell biomarker of the present invention (e.g., cancerous cells or tissue). In vivo imaging is used to visualize the presence of a biomarker indicative of a cancer stem cell. Such techniques allow for diagnosis without the use of a biopsy. The in vivo imaging methods of the present invention are also useful for providing prognoses to cancer patients. For example, the presence of a cancer stem cell biomarker indicative of an aggressive cancer likely to metastasize or likely to respond to a certain treatment can be detected. The in vivo imaging methods of the present invention can further be used to detect a cancer stem cell (e.g., one that has metastasized) in other parts of the body.

In some embodiments, reagents (e.g., antibodies) specific for a cancer stem cell biomarker of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference). In some embodiments, flow-cytometry is utilized to monitor (e.g., detect) a marker (e.g., a cancer stem cell biomarker of the present invention). The use of flow-cytometry to identify and/or isolate and/or purify cell populations is well known in the art (See, e.g., Givan, Methods Mol Biol 263, 1-32 (2004)).

In other embodiments, antibodies are radioactively labeled. The use of antibodies for in vivo diagnosis is well known in the art. Sumerdon et al., (Nucl. Med. Biol 17:247-254 (1990) have described an optimized antibody-chelator for the radioimmunoscintographic imaging of tumors using Indium-111 as the label. Griffin et al., (J Clin Onc 9:631-640 (1991)) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

An antibody against a biomarker of the present invention may be any monoclonal or polyclonal antibody, as long as it can recognize the cancer stem cell biomarker. Antibodies can be produced by using a cancer stem cell biomarker of the present invention as the antigen according to a conventional antibody or antiserum preparation process.

Cancer stem cells (e.g., populations representing both MET and EMT cancer stem cells) of the present invention can be used to determine the effect of test compounds (e.g., small molecule inhibitors, pharmaceuticals, biological agents, etc.). Examples of test compounds include, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, drug, antibody, prodrug, glycopeptides, glycoproteins, proteoglycans and the like, and synthetic analogues or derivatives thereof, including peptidomimetics, small molecule organic compounds and the like, and mixtures thereof (e.g., that is a candidate for use to treat or prevent a disease, illness, sickness, or disorder of bodily function (e.g., cancer (e.g., cancer stem cell growth)). Test compounds comprise both known and potential therapeutic compounds. A test compound can be determined to be therapeutic by screening using the screening methods of the present invention. To determine the effect of a test compound on cancer stem cells, cancer stem cells can be obtained from a subject with cancer. Once obtained, cancer stem cells can be cultured in vitro or in vivo and exposed to a test compound.

The ability of test compounds to alter (e.g., increase or decrease) cancer stem cell growth or maintenance, as well as the effect on normal HSCs, can be assayed. For example, in some embodiments, test compounds (e.g., from a library of compounds) are screened for their ability to alter (e.g., eliminate or inhibit growth of) cancer stem cells, while concurrently monitoring the effect on HSCs (e.g., driving HSCs into quiescence). Screening in this way permits the identification of compounds that can be utilized (e.g., independently, in a pharmaceutical composition, or co-administered) for treating cancer (e.g., inhibiting or eliminating cancer stem cells while having no harmful effect on normal HSCs).

In some embodiments, test compounds can be solubilized and added to cancer stem cells (e.g., in vitro (e.g., in the culture medium), or, in vivo (e.g., to a recipient subject that has received a cancer stem cell graft)). In some embodiments, various concentrations of the test compound are utilized to determine an efficacious dose. In some embodiments, administration of the test compound is consistent over a period of time (e.g., administered to a recipient one, two or more times a day, or, added to media in vitro) so as to keep the concentration of the test compound constant.

Alteration (e.g., inhibiting growth or promoting death or permitting maintenance) of cancer stem cells, and normal stem cells, can be monitored in vitro or in vivo. For example, an increase or decrease in the number of cancer cells (e.g., cancer stem cell progeny) that form or an increase or decrease in the size of the foci in vitro, or growth rate of cancer cells (e.g., cancer stem cell progeny can be monitored. The effect of a test compound on cancer stem cells and normal HSCs can be measured by determining the number of cancer stem cells that persist in culture or in vivo after treatment (e.g., administration of the test compound). In addition, cancer stem cell and HSC status (e.g., cell cycle status, cancer stem cell biomarker expression, etc.) can be determined (e.g., using compositions and methods described herein).

Test compounds can be administered in vitro or in vitro at a variety of concentrations. For example, in some embodiments, test compounds are added to culture medium or to a subject so as to achieve a concentration from about 10 pg/ml to 1 µg/ml, or from about 1 ng/ml (or 1 ng/cc of blood) to 100 ng/ml (or 100 ng/cc of blood).

The effects of a test compound can also be identified on the basis of a significant difference relative to a control regarding criteria such as the ratios of expressed phenotypes, cell viability, proliferation rate, number of cancer stem cells, cancer stem cell activity upon transplantation in vivo, cancer stem cell activity upon transplantation in culture, cell cycle distribution of cancer cells, and alterations in gene expression.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive (See, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994), each of which is incorporated by reference herein in its entirety.

Alternatively, the test compound libraries employed in this invention may be prepared or obtained by any means including, but not limited to, combinatorial chemistry techniques, fermentation methods, plant and cellular extraction procedures and the like. Methods for making combinatorial libraries are well-known in the art (See, e.g., E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Each of these references is incorporated herein by reference in its entirety).

Libraries of test compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223, 409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

In addition to active ingredients, test compounds may comprise suitable pharmaceutically acceptable carriers comprising excipients and auxiliaries, that facilitate processing of the active compounds into preparations which can be used pharmaceutically.

In certain embodiments, one can test whether inhibiting IL6, Notch, Wnt, Hedgehog or TGFβ can decrease EMT BCSCs induced with mir-100 overexpression by flow cytometry analysis for CD24−CD44+ and sensitize the tumor cells to chemotherapy both in vitro and in vivo. IL6, TGFβ, Hedgehog, WNT and/or Notch activity is necessary for maintaining EMT. Work conducted during embodiments of the present invention has shown that mir-100 over-expression can switch the breast cancer stem cells to EMT state which is characterized by EpCAM− and CD24−CD44+. The potential for inhibiting these pathways to alter CSC/EMT status and block resistance to chemotherapy provide insight to using combination treatment. One can establish cancer cell lines or cells from primary human breast cancer xenografts or fresh tumor tissues from different subtypes with inducible mir-100 over-expression, and treat them with the inhibitor for each of these pathways (IL-6, TGFβ, Hedgehog, WNT and/or Notch) docetaxel and combination to evaluate the percentage/absolute number change of EMT BCSCs and tumor growth. It may be that the EMT BCSCs by mir-100 overexpression will be sensitive to most or all of the inhibitors against to these pathways, which will sensitize the tumor's response to chemotherapy.

In some embodiments, one can test whether a Pan-erb blocker or Her2 pathway inhibitor can decrease MET BCSCs induced with mir-93 over-expression by flow cytometry analysis for ALDH+ and sensitize the tumor cells to chemotherapy both in vitro and in vivo. Work conducted during development of embodiments of the present invention showed that Her2-positive luminal cells have more BCSCs characterized by ALDH+. Data generated has shown that mir-93 overexpression can switch the breast cancer stem cells to MET state which is characterized by EpCAM+ and ALDH+. Therefore, one may inhibit the her2 pathway to alter CSC/MET status and block resistance to chemotherapy and provide insight to using combination treatment. One could establish cancer cell lines or cells from primary human breast cancer xenografts or fresh tumor tissues from different subtypes with inducible mir-93 over-expression, and treat them with the Pan-erb blocker, docetaxel and combination to evaluate the percentage/absolute number change of MET BCSCs and tumor growth. It may be that the MET BCSCs by mir-93 over-expression will be sensitive to Pan-erb blockers, which will sensitize the tumor's response to chemotherapy.

In particular embodiments, one could combine the approaches described in the two paragraphs above to test whether combination therapy can decrease or eradiate all BCSCs by flow cytometry analysis for both CD24−CD44+ and ALDH+, and sensitize the tumor cells to chemotherapy both in vitro and in vivo. Since it has been shown that BCSCs exist in two states within a tumor, it is believed that targeting only one state of BCSCs will not be efficient. It is expected that this combination therapy will dramatically shrink the tumor and completely wipe out BCSCs and prevent the relapse.

In some embodiments, microRNA100 (or mir-221) and microRNA93 can be utilized as biomarkers to help patients find the individualized combination therapy targeting both states of BCSCs and the bulk tumor cells. Such detecting can employ microRNA ISH staining with the slide section from paraffin-embedded clinical human breast tumor specimens, or can detect the microRNA expression level in patient blood serum by qRT-PCR. Based on different microRNA expression in the tumor specimens and blood, one can predict which patient will more likely develop distant metastasis and help determine the best combination therapy for the patients.

This invention further pertains to novel agents identified by the above-described screening assays. Accordingly, it is within the scope of this invention to further use an agent identified as described herein (e.g., a test compound that: eliminates or inhibits growth of a cancer stem cell while leaving unharmed (e.g., inducing quiescence of) normal stem cells; acts as a cancer stem cell biomarker modulating agent; an antisense cancer stem cell biomarker nucleic acid molecule; a siRNA molecule; a cancer stem cell biomarker specific antibody; or a cancer stem cell biomarker-binding partner) in an appropriate animal model to determine the efficacy, toxicity, side effects, or mechanism of action, of treatment with such an agent. Furthermore, novel agents identified by the above-described screening assays can be, e.g., used for treatments as described herein.

It is contemplated that pharmaceutical compositions comprising a successfully identified test compound (e.g., a test compound identified that is capable of altering (e.g., inhibiting growth or eliminating) cancer stem cells while concurrently not harming (e.g., inducing quiescence of) normal HSCs), analogue or mimetic can be administered systemically or locally to alter cancer stem cell growth and induce cancer (e.g., tumor) cell death in cancer patients by targeting both EMT and MET cancer stem cells.

It is not intended that the present invention be limited by the particular route of administration. Indeed, a variety of administrative routes are contemplated to be useful in the present invention including, but not limited to, intravenously, intrathecally, intramuscularly, intraperitoneally as well as orally. Moreover, they can be administered alone or in combination with anti-proliferative drugs.

Where combinations are contemplated, it is not intended that the present invention be limited by the particular nature of the combination. The present invention contemplates combinations as simple mixtures as well as chemical hybrids. An example of the latter is where a peptide or drug is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. The compositions are also prepared as injectables, either as liquid solutions or suspensions; solid forms suitable for solution in, or suspension in, liquid prior to injection may also be prepared. The compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents. Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

It may be desirable to administer an analogue of a successfully identified test compound (e.g., a test compound identified that is capable of altering both EMT and MET cancer stem cells). A variety of designs for such mimetics are possible. For example, cyclic peptides, in which the necessary conformation for binding is stabilized by nonpeptides, are specifically contemplated. (See, e.g., U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all hereby incorporated by reference, describe multiple methods for creating such compounds).

Synthesis of nonpeptide compounds that mimic peptide sequences is also known in the art. For example, Eldred et al., J. Med. Chem. 37:3882 (1994), describe nonpeptide antagonists that mimic the Arg-Gly-Asp sequence. Likewise, Ku et al., J. Med. Chem. 38:9 (1995) give further elucidation of the synthesis of a series of such compounds. Such nonpeptide compounds are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexyl-carbodiimide (DCC). The attack of a free amino group on the activated carboxyl leads to the formation of a peptide bond and the release of dicyclohexylurea. It may be important to protect potentially reactive groups other than the amino and carboxyl groups intended to react (e.g., the x-amino group of the component containing the activated carboxyl group can be blocked with a tertbutyloxycarbonyl group). This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

The methods of the present invention can be practiced in vitro, ex vivo, or in vivo. For example, the method of the present invention can be used in vitro to screen for compounds which are potentially useful for combinatorial use with a successfully identified test compound for treating cancer (e.g., lymphoma, leukemia, prostate, lung, stomach, breast, colon, and/or pancreatic cancer); to evaluate a test compound's efficacy in treating cancer; or to investigate the mechanism by which a test compound combats cancer (e.g., whether it does so by inducing apoptosis, by inducing differentiation, by decreasing proliferation, etc). For example, once a compound has been identified as a compound that works, one skilled in the art can apply the method of the present invention in vitro to evaluate the degree to which the compound induces apoptosis and/or decreases angiogenesis, proliferation of cancer cells; or one skilled in the art can apply the method of the present invention to determine whether the compound operates by inducing apoptosis, by decreasing proliferation and/or angiogenesis, or by a combination of these methods.

Alternatively, a method of the present invention can be used in vivo to treat cancers, (e.g., including, but not limited to, lymphoma, leukemia, prostate cancer, lung cancer, stomach cancer, pancreatic cancer, breast cancer, and colon cancer). In the case where a method of the present invention is carried out in vivo, for example, where the cancer cells are present in a human subject, contacting can be carried out by administering a therapeutically effective amount of the compound to the human subject (e.g., by directly injecting the compound into a tumor or through systemic administration).

In some embodiments, the present invention provides high throughput screening of test compounds. For example, in some embodiments, large numbers of different test compounds (e.g., from a test compound library, described above) are provided (e.g. attached to or synthesized) on a solid substrate. Test compounds can be reacted with cancer stem cells, or portions thereof, and washed. Bound cancer stem cells are then detected by methods well known in the art, using commercially available machinery and methods (e.g., the Automated Assay Optimization (AAO) software platforms (Beckman, USA) that interface with liquid handlers to enable direct statistical analysis that optimizes the assays; modular systems from CRS Robotics Corp. Burlington, Ontario), liquid handling systems, readers, and incubators, from various companies using POLARA (CRS), an open architecture laboratory automation software for a Ultra High Throughput Screening System; 3P (Plug&Play Peripherals) technology, which is designed to allow the user to reconfigure the automation platform by plugging in new instruments (ROBOCON, Vienna, Austria); the Allegro system or STACCATO workstation (Zymark), which enables a wide range of discovery applications, including HTS, ultra HTS, and high-speed plate preparation; MICROLAB Vector software (Hamilton Co., Reno, Nev., USA) for laboratory automation programming and integration; and others).

In some embodiments, assays measure a response the target cells (cancer stem cells or genetically modified cancer stem cells) provide (e.g., detectable evidence that a test compound may be efficacious). In some embodiments, the detectable signal is compared to control cells and the detectable signal identified by subtraction analysis. The relative abundance of the differences between the "targeted" and "untargeted" aliquots can be simultaneously compared (e.g., using a "subtraction" analysis (differential analysis) technique such as differential display, representational difference analysis (RDA), GEM-Gene Expression Microarrays (U.S. Pat. No. 5,545,531), suppressive subtraction hybridization (SSH) and direct sequencing (PCT patent application WO 96/17957). The subtraction analysis can include the methods of differential display, representational differential analysis (RDA), suppressive subtraction hybridization (SSH), serial analysis of gene expression (SAGE), gene expression microarray (GEM), nucleic acid chip technology, or direct sequencing).

In certain embodiments, the present invention provides method and compositions for co-administration of therapeutics, such as at least one therapeutic that targets cancer stem cells in the EMT stage and at least one therapeutic that targets cancer stem cells in the MET stage. In particular embodiments, a third anti-neoplastic agent is co-administered that kills cancer cells. In this regard, a patient is treated for both types of cancer stem cells and bulk cancer cells in order to remove all types of cells with a particular treatment.

A wide range of therapeutic agents find use with the present invention. Any therapeutic agent that can be co-administered with the agents of the present invention, or associated with the agents of the present invention is suitable for use in the methods of the present invention. Some embodiments of the present invention provide methods (therapeutic methods, research methods, drug screening methods) for administering a therapeutic compound of the present invention and at least one additional therapeutic agent (e.g., including, but not limited to, chemotherapeutic antineoplastics, antimicrobials, antivirals, antifungals, and anti-inflammatory agents) and/or therapeutic technique (e.g., surgical intervention, radiotherapies).

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |

TABLE 1-continued

| | | |
|---|---|---|
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chloroethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |

TABLE 1-continued

| | | |
|---|---|---|
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate], disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$, Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |

TABLE 1-continued

| | | |
|---|---|---|
| Levamisole HCl<br>((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine<br>(1-(2-chloro-ethyl)-3-cyclohexyl-1-nitrosourea) | CeeNU | Bristol-Myers Squibb |
| Mechlorethamine, nitrogen mustard<br>(2-chloro-N-(2-chloroethyl)-N-methylethanamine hydrochloride) | Mustargen | Merck |
| Megestrol acetate<br>17α(acetyloxy)-6-methylpregna-4,6-diene-3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6 H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-pteridinyl)methyl]methylamino]benzoyl]-L-glutamic acid) | Methotrexate | Lederle Laboratories |
| Methoxsalen<br>(9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane<br>(1,1-dichloro-2-(o-chlorophenyl)-2-(p-chlorophenyl) ethane) | Lysodren | Bristol-Myers Squibb |
| Mitoxantrone<br>(1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin<br>(IL-11) | Neumega | Genetics Institute, Inc., Alexandria, VA |
| Oxaliplatin<br>(cis-[(1R,2R)-1,2-cyclohexanediamine-N,N'] [oxalato(2-)-O,O'] platinum) | Eloxatin | Sanofi Synthelabo, Inc., NY, NY |
| Paclitaxel<br>(5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate<br>(phosphonic acid (3-amino-1-hydroxypropylidene) bis-, disodium salt, pentahydrate, (APD)) | Aredia | Novartis |
| Pegademase<br>((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase<br>(monomethoxypolyethylene glycol succinimidyl L-asparaginase) | Oncaspar | Enzon |
| Pegfilgrastim<br>(covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin<br>(antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine<br>(N-isopropyl-μ-(2-methylhydrazino)-p-toluamide monohydrochloride) | Matulane | Sigma Tau Pharmaceuticals, Inc., Gaithersburg, MD |
| Quinacrine<br>(6-chloro-9-(1-methyl-4-diethyl-amine) butylamino-2-methoxyacridine) | Atabrine | Abbott Labs |
| Rasburicase<br>(recombinant peptide) | Elitek | Sanofi-Synthelabo, Inc., |
| Rituximab<br>(recombinant anti-CD20 antibody) | Rituxan | Genentech, Inc., South San Francisco, CA |
| Sargramostim<br>(recombinant peptide) | Prokine | Immunex Corp |
| Streptozocin<br>(streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |

TABLE 1-continued

| | | |
|---|---|---|
| Talc (Mg$_3$Si$_4$O$_{10}$(OH)$_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine (C$_{46}$H$_{56}$N$_4$O$_{10}$•H$_2$SO$_4$) | Velban | Eli Lilly |
| Vincristine (C$_{46}$H$_{56}$N$_4$O$_{10}$•H$_2$SO$_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Any and all combinations of one of the specific anti-cancer agents listed above (as the third therapeutic agent) with a specific EMT cancer stem cell agent (first therapeutic agent) and a specific MET cancer stem cell agent (second therapeutic agent) may be administered to a subject or packaged in a composition or kit.

EXPERIMENTAL

The following example is provided in order to demonstrate and further illustrate certain preferred embodiments and aspects of the present invention and are not to be construed as limiting the scope thereof.

Example 1

Cancer Stem Cells have Different States

Figure 2:
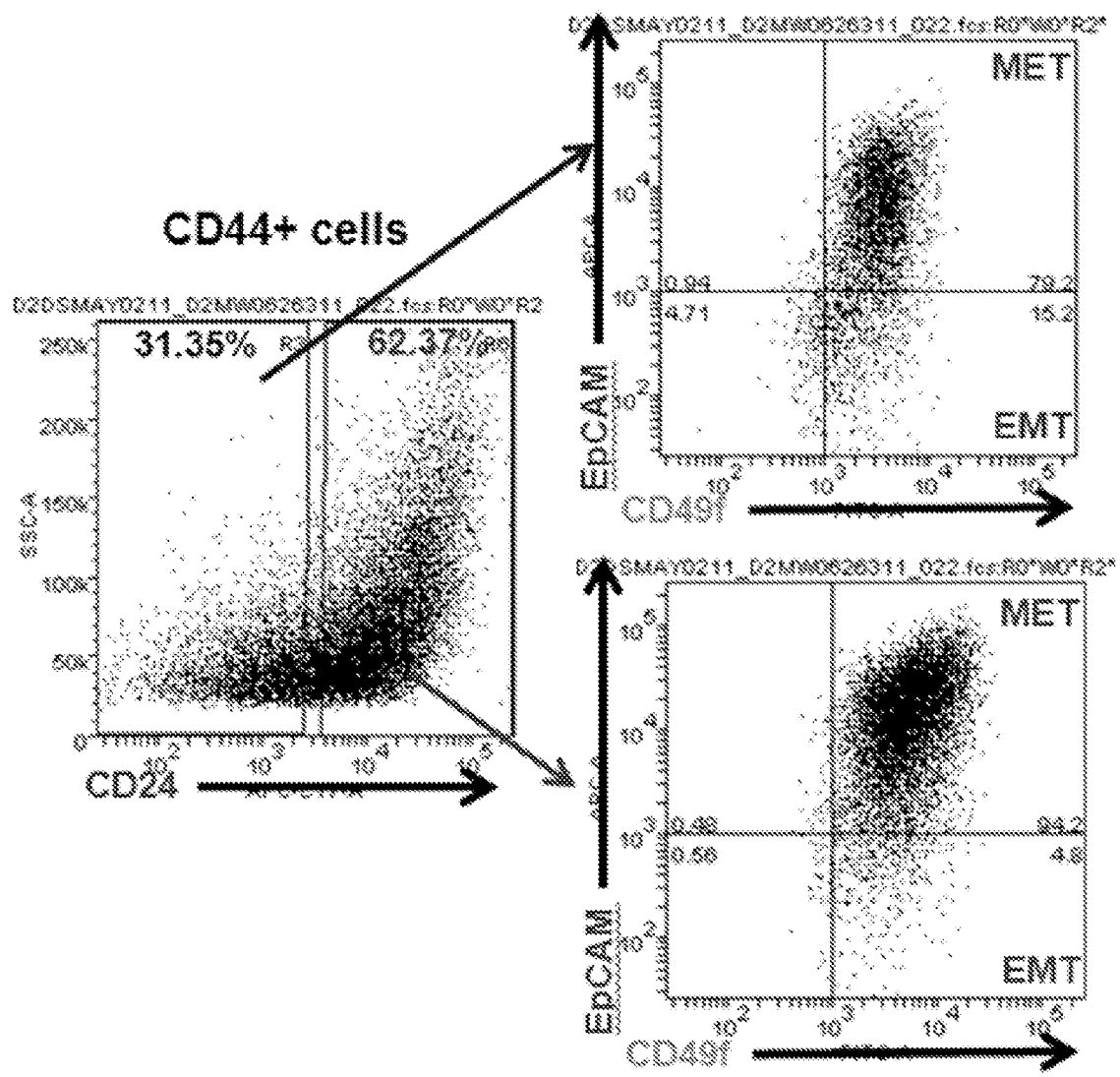
FIG. 2 shows CD24$^-$CD44$^+$ cells are enriched in EMT population. Cells grown in T75 flasks at about 85% confluency were analyzed with Aldefluor, CD24 and CD44 as described in Example 1.
Figure 3:
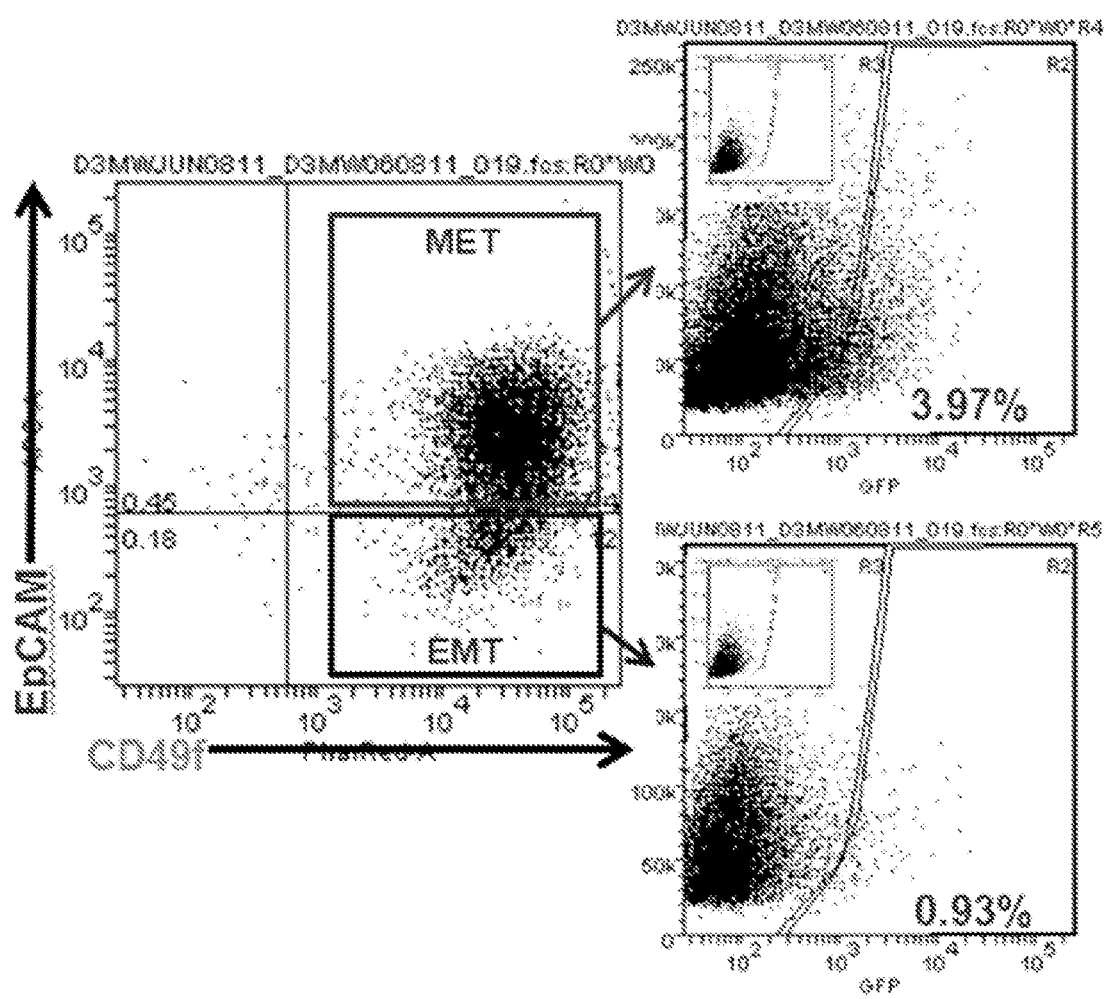
FIG. 3 shows ALDH$^+$ cells are enriched in MET population. Cells grown in T75 flasks at about 85% confluency were analyzed with Aldefluor, EpCAM and CD49f as described in Example 1.
Figure 4:
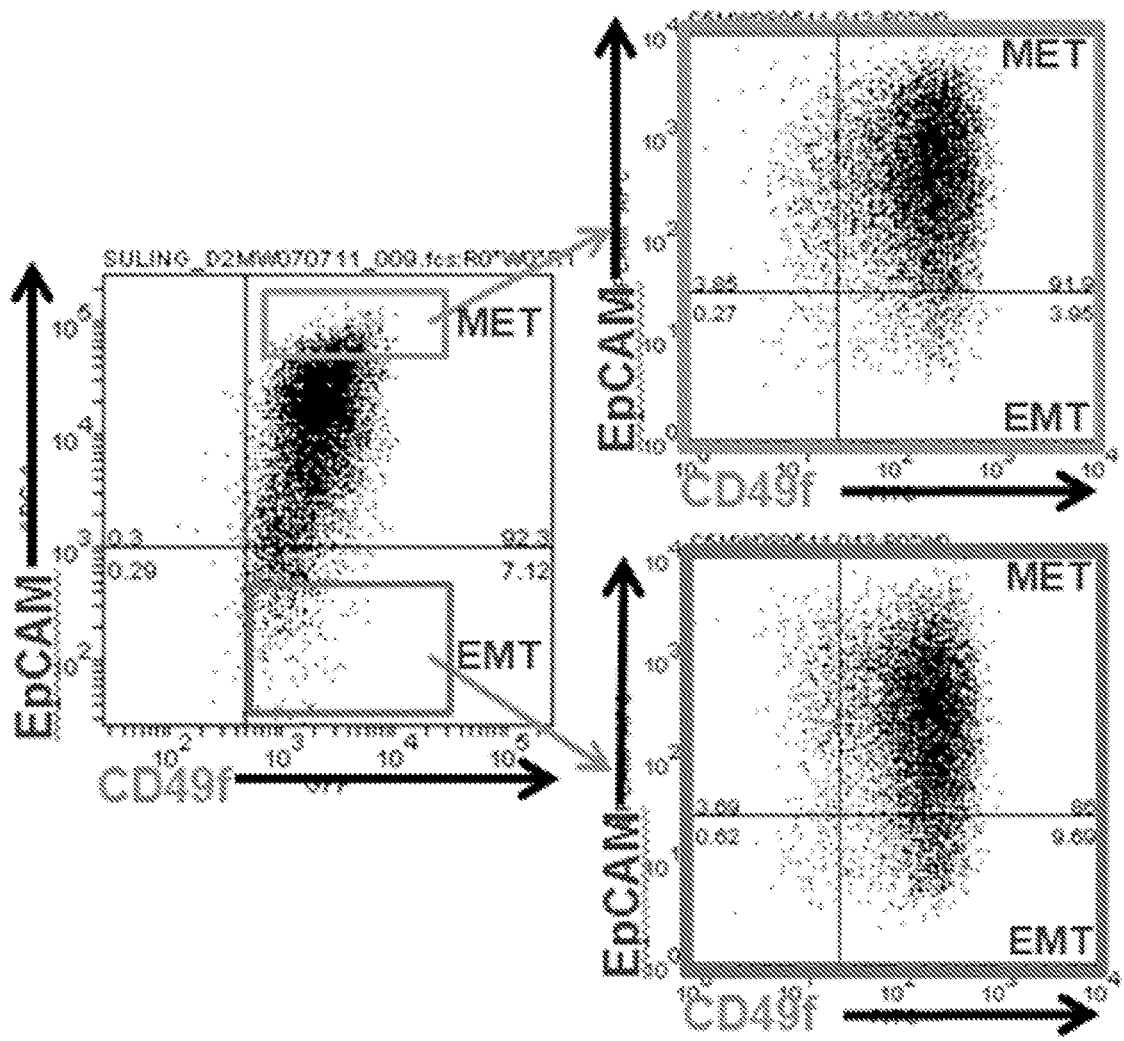
FIG. 4 shows the inter-conversion of EMT and MET cells. EpCAM$^+$CD49f$^+$ cells and EpCAM$^-$CD49f$^+$ cells were sorted by flow cytometry. 200k cells were plated in T75 flasks and cultured for 11 days, and then the cells were dissociated and analyzed for CD49f and EpCAM.

Utilizing primary breast tissue and established cell lines, it was demonstrated that both normal and malignant breast stem cells exist in distinct, inter-convertible states. The EMT state is characterized by expression of vimentin and N-cadherin, slug, snail and twist transcription factors. EMT CSCs have a mesenchymal morphology, are largely quiescent, invasive, EpCAM$^-$CD49f$^+$ (FIG. 1) and are characterized by expression of the CSC markers CD44$^+$CD24$^-$ (FIG. 2). In contrast, the MET (mesenchymal epithelial transition) state of CSCs is characterized by an epithelial morphology and expression of E-cadherin and EpCAM. MET CSCs are EpCAM$^+$CD49F$^+$ (FIG. 1) and express the CSC marker Aldehyde dehydrogenase (ALDH) (FIG. 3). Furthermore, it was demonstrated that these two states of CSCs are inter-convertible and they can regenerate each other in culture (FIG. 4). A subpopulation of cells expressing both CD44$^+$CD24$^-$ and ALDH may represent cells in transition between these states.

Figure 5:
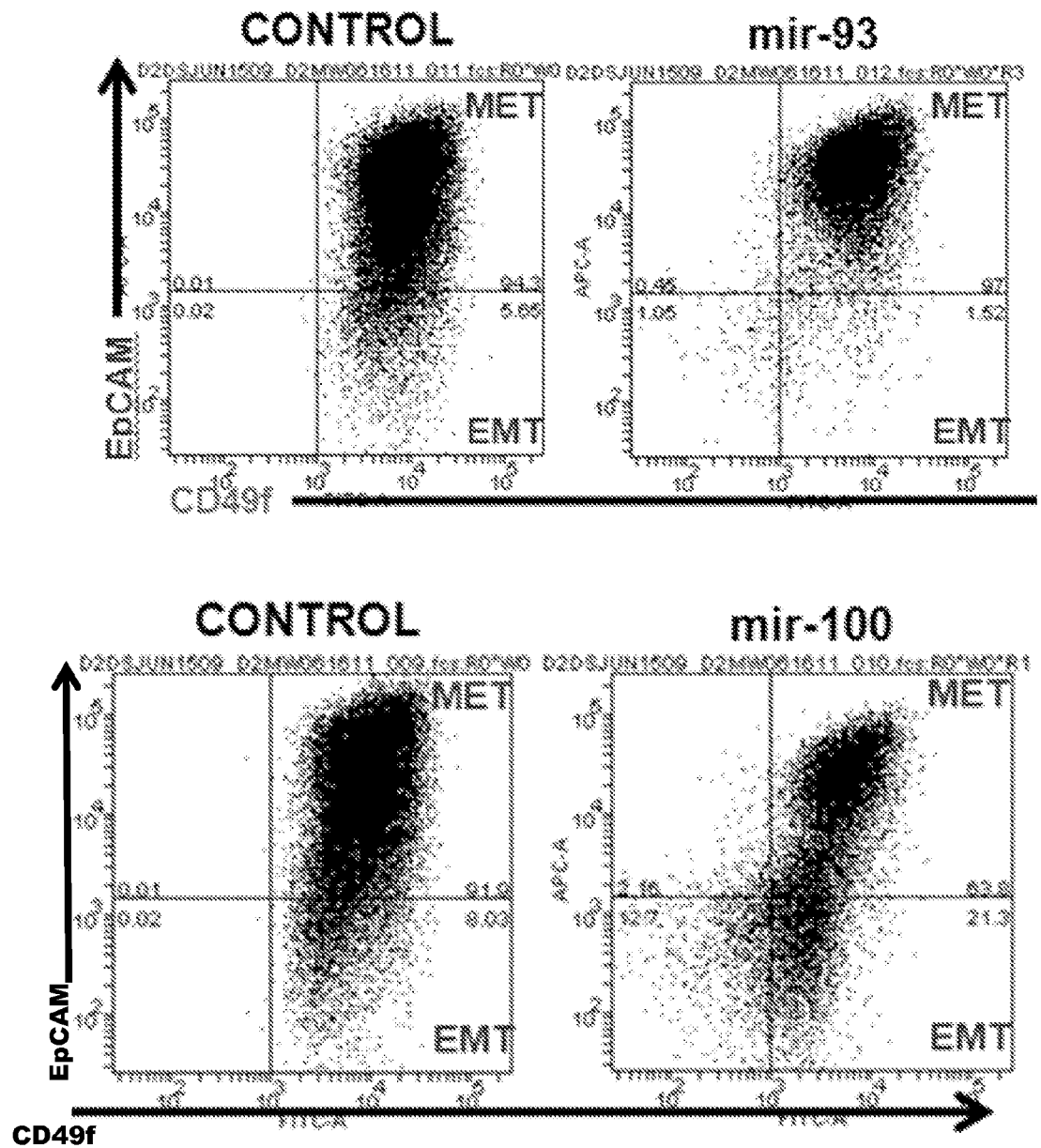
FIG. 5 shows that the inter-conversion between EMT and MET is regulated by microRNAs. Cells were transduced with pTRIPZ-microRNA-RFP lentiviruses with inducible systems and selected with puromycin, and microRNAs were induced with or without (CONTROL) Doxycycline and analyzed for RFP, EpCAM and CD49f.
Figure 6:
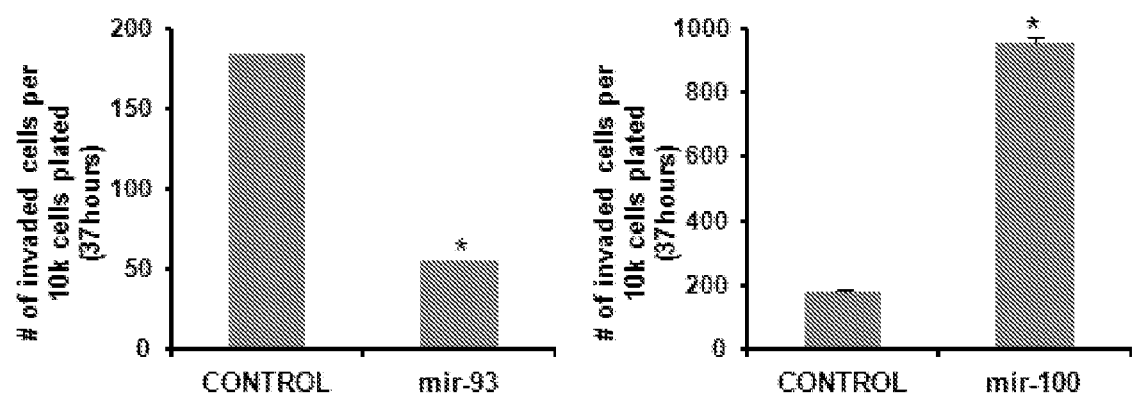
FIG. 6 shows microRNAs regulate cell invasion in vitro. The invasive capability of pTRIPZ-mir-93-RFP cells or pTRIPZ-mir-100-RFP cells with or without (CONTROL) Doxycycline was assessed by matrigel invasion assay. 10000k cells were plated in Matrigel and serum was utilized as the attractant.

It was further demonstrated that the EpCAM$^+$CD49f$^+$ population is characterized by the highest expression of mir-93 by qRT-PCR. A TET on/off inducible system was established to over-express microRNAs in a lentiviral vector tagged with RFP. Utilizing this system, it was shown that forced over-expression of mir-93 increases the proportion of EpCAM$^+$CD49f$^+$ and ALDH$^+$ cells (FIG. 5). Furthermore, it was demonstrated that expression levels of mir-100 are significant higher in EpCAM⁻CD49f⁺ and EpCAM⁻CD49f populations than in EpCAM⁺CD49f⁺ and EpCAM⁺CD49f⁺ populations. Furthermore, forced over-expression of mir-100 increased the proportion of EpCAM⁻CD49f⁺ cells (FIG. 5). This resulted in an increase in the proportion of CD24⁻CD44⁺ CSC cells with a concomitant decrease in the ALDH⁺ CSC population. These results indicate that mir-93 and mir-100 are important regulators of the transition between the EMT and MET stem cell states. It was demonstrated that the induction of mir-93 in EMT SUM159 cells induces an MET in the ALDH-positive CSC population and decreased cell invasion assessed by in vitro matrigel assay (FIG. 6). Furthermore, over-expression of mir-100 resulted in a decrease of the ALDH-positive CSC population with a concomitant increase in the CD24−CD44+ population accompanied by induction of EMT, and increased cell invasion in vitro (FIG. 6).

Example 2

Characterization of the States of Cancer Stem Cells

Figure 10:
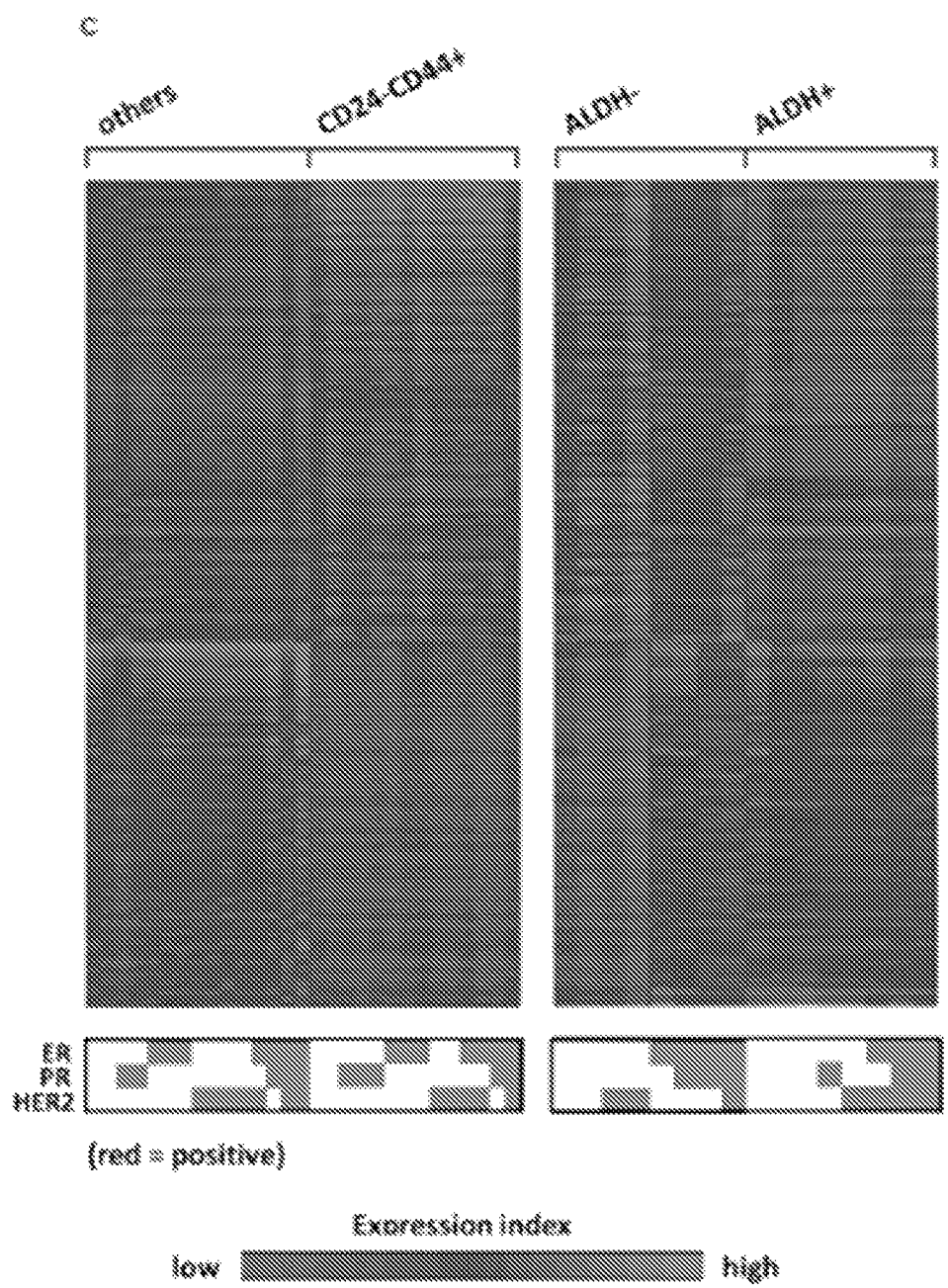
FIG. 10. CD24$^-$CD44$^+$ and ALDH$^+$ cells display reciprocal EMT-MET profiles in primary human breast cancer. (A) Venn diagram of the intersection between genes elevated in CD24$^-$CD44$^+$ compared with other flow-sorted cells (others) and genes diminished in ALDH$^+$ compared with ALDH$^-$ cells (|fold change|>1.5 for each comparison). (B) Venn diagram of the intersection between genes diminished in CD24$^-$CD44$^+$ vs. others and genes elevated in ALDH$^+$ vs. ALDH$^-$. (C) Heat map of genes with opposite expression patterns between CD24$^-$CD44$^+$ and ALDH$^+$ (from parts A and B). Each row represents a RNA transcript; each column represents a sample (red: high expression). (D) Expression of EMT/MET markers in CD24$^-$CD44$^+$ vs. others and ALDH$^+$ vs. ALDH$^-$. (E) Localization of CD24 (Magenta), CD44 (Green), ALDH1 (Red), and DAPI (Blue) in clinical samples of human invasive breast carcinoma as accessed by immunofluorescence staining. Bar, 100 um.
Figure 14:
FIG. 14A shows a venn diagram showing the intersection between genes elevated in cancer mammospheres vs. primary cancers, genes elevated in CD24–CD44+ vs. others, and genes elevated in ALDH+ vs. ALDH– cells (|fold change|>1.5 for each comparison).
FIG. 14B is the same as 14A but for genes diminished in cancer mammospheres vs. primary cancers, genes diminished in CD24–CD44+ vs. others, and genes diminished in ALDH+ vs. ALDH– cells. P-value of overlap between any two datasets is smaller than 2.2E-16.

In this Example gene expression profiling was performed for CD24⁻CD44⁺ and ALDH+ expressing cell populations isolated from a total of 45 primary human breast cancers. Of 3677 RNA transcripts elevated in the CD24⁻CD44⁺ cell population, 1724 were diminished in the ALDH⁺ population (FIG. 10A). Conversely, of the 5218 mRNA transcripts elevated in the ALDH⁺ population, 1362 were diminished in the CD24⁻CD44⁺ population (FIG. 10B). Furthermore, the reciprocal gene expression patterns between CD24⁻CD44⁺ and ALDH⁺ populations were independent of the molecular subtype of breast cancer (i.e. luminal ER/PR⁺, HER2⁺ or triple negative) (FIG. 10C). Since sphere formation under anchorage independent conditions has been shown to be a property of tumor initiating cells, the expression profile of each of these cell populations was compared to those in tumor spheres generated from primary human tumors. Even though many genes demonstrated opposite expression patterns in the CD24⁻CD44⁺ and ALDH⁺ populations, a set of genes expressed in CD24⁻CD44⁺ and ALDH⁺ populations displayed overlap with those from tumor sphere populations (FIG. 14). This suggests that despite significant differences between cells characterized by CD24⁻CD44⁺ or ALDH expression, they share characteristics associated with "stemness." Furthermore, even though the different subtypes of breast cancer can be classified by virtue of differential gene expression patterns of bulk cell populations, the CD24⁻CD44⁺ and ALDH⁺ CSC populations share common expression patterns across these subtypes.

Methods:
Patients and Clinical Samples.
The following comparisons were made on breast cancer patients or breast cancer cell line samples: i) flow-sorted samples: CD24⁻CD44⁺ vs. all other flow-sorted cells obtained from GSE7513 in public Gene Expression Omnibus (GEO); ii) flow-sorted samples: ALDH⁺ vs. ALDH⁻ obtained from 16 breast cancer patients; iii) flow-sorted samples: CD24⁻CD44⁺ vs. all other flow-sorted cells and ALDH⁺ vs. ALDH⁻ from breast cell lines MCF10A, SUM149, primary xenograft MC1 and normal breast epithelial cells from patients.

Data Analysis.
Gene expression arrays were analyzed using Partek Genomics Suite. For each of the profile datasets, the data was pretreated by Quantile normalization and made log 2-base conversion. Principal and Components Analysis (PCA) was conducted to determine and remove outliers. The fold changes between groups was computed for CD24⁻CD44⁺ vs. all others and ALDH⁺ vs. ALDH⁻ by ANOVA. Expression values were visualized as heat maps by intensity plot function in Partek.

Immunostaining.
For ALDH1, CD24, CD44, and DAPI quadruple fluorescent staining, paraffin-embedded sections of breast tumors or normal breast tissues were deparaffinized in xylene and rehydrated in graded alcohol. Antigen enhancement was done by incubating the sections in citrate buffer pH 6.0 (Dakocytomation) as recommended. CD24 antibody (Neomarkers), ALDH1 antibody (BD biosciences), and CD44 antibody (Thermo Scientific) were used at a 1:50 dilution and incubated for 1 hour. Alexafluor 647-, Alexafluor 546-, Alexafluor 488-labeled secondary antibodies (Invitrogen) were used at a 1:200 dilution and incubated for 20 minutes. Nuclei were counterstained with DAPI/antifade (Invitrogen; blue color in the staining) and cover-slipped. Sections were examined with a fluorescent microscope (EVOS FL, AMG).

Patients and Clinical Samples
We made the following comparisons on breast cancer patients or breast cancer cell line samples: i) flow-sorted samples: CD24⁻CD44⁺ vs. all other flow-sorted cells obtained from GSE7513 in public Gene Expression Omnibus (GEO); ii) flow-sorted samples: ALDH⁺ vs. ALDH⁻ obtained from 16 breast cancer patients; iii) flow-sorted samples: CD24⁻CD44⁺ vs. all other flow-sorted cells and ALDH⁺ vs. ALDH⁻ from breast cell lines MCF10A, SUM149, primary xenograft MC1 and normal breast epithelial cells from patient.

Cell Culture
Breast cancer cell line SUM149 was from Asterland[24] and MCF10A was purchased from ATCC, which were cultured as previously described[25].

Flow Cytometry—
Core biopsies and normal breast tissues were taken and placed immediately in cold RPMI-1640 supplemented with 10% heat-inactivated newborn calf serum (HINCS, Invitrogen). In summary, the samples were digested in collagenase and 1×10⁶ single cells were resuspended, incubated for 15 min with anti-CD44, anti-CD24, and anti-lineage mixture antibodies (PE-conjugated anti-CD2, CD3, CD10, CD16, CD18, CD31, and CD 140B) (PharMingen) using the manufacturer's suggested concentrations, and then followed by Aldefluor assay as described before[3], and analyzed using MoFlo Astrios flow cytometry. Side and forward scatter were used to eliminate debris and cell doublets, and the Lin cells were further analyzed for expression of the CD44/CD24 and ALDH markers. The detailed procedure for cell lines and cells from primary xenografts was described previously[25].

RNA Extraction—
Total RNA was isolated using RNeasy Micro Kit (Qiagen, Valencia, Calif.), and total RNA with enriched miRNA was isolated using miRNeasy mini Kit, according to the manufacturer's instructions.

Gene Expression Profiling—
Gene expression analyses used Affymetrix U133 Plus 2.0 human oligonucleotide microarrays. Preparation of cRNA, hybridizations, washes and detection were done as recommended by the supplier. Expression data were analyzed by the RobustMultichip Average method in R using Bioconductor and associated packages[26].

Data Analysis—
We analyzed gene expression arrays using Partek Genomics Suite. For each of the profile datasets, we pretreated the data by Quantile normalization and made log 2-base conversion. Principal and Components Analysis (PCA) was conducted to determine and remove outliers. Fold changes were computed between groups CD24$^-$CD44$^+$ vs. all others and ALDH$^+$ vs. ALDH$^-$ by ANOVA. Expression values were visualized as heat maps by intensity plot function in Partek.

Real-Time Quantitative PCR (qRT-PCR)—

For reverse-transcriptase reactions, 1 µg of total RNA from the sorted cells was reverse transcribed with 200 U M-MLV Reverse Transcriptase (GibcoBRL) at 42° C. for 1 hour in the presence of 5 mM each of dATP, dCTP, dGTP and dTTP, 4 µl, 5×1st strand buffer (GibcoBRL), 0.01M DDT, 1 U RNA Guard RNase inhibitor (GibcoBRL), and 2.5 µM random primers in a total volume of 20 µl. The reaction was terminated by heating to 95° C. for 3 minutes. Real-time quantitative PCR (TaqMan™) primers and probes were purchased from Applied Biosystems as Assays-on-Demand™ Gene Expression Products. Real-time PCRs were performed following the supplier's instructions (Applied Biosystems). 20 µl of PCR mixture contained 10 µl of 2× Taqman™ universal PCR Master Mix, 1 µl of 20× working stock of gene expression assay mix, and 50 ng of RNA converted cDNA. PCR was performed in a ABI PRISM® 7900HT sequence detection system with 384-Well block module and automation accessory (Applied Biosystems) by incubation at 50° C. for 2 min and then 95° C. for 10 min followed by 40 amplification cycles (15 s of denaturation at 95° C. and 1 min of hybridization and elongation at 60° C.). The reaction for each sample was performed in quadruplicates. Fluorescence of the PCR products was detected by the same apparatus. The number of cycles that it takes for amplification plot to reach the threshold limit, the Ct-value was used for quantification. TBP was used for normalization.

Immunostaining—

For ALDH1, CD24, CD44, and DAPI quadruple fluorescent staining, paraffin-embedded sections of breast tumors or normal breast tissues were deparaffinized in xylene and rehydrated in graded alcohol. Antigen enhancement was done by incubating the sections in citrate buffer pH 6.0 (Dakocytomation) as recommended. CD24 antibody (Neomarkers), ALDH1 antibody (BD biosciences), and CD44 antibody (Thermo Scientific) were used at a 1:50 dilution and incubated for 1 hour. Alexafluor 647-, Alexafluor 546-, Alexafluor 488-labeled secondary antibodies (Invitrogen) were used at a 1:200 dilution and incubated for 20 minutes. Nuclei were counterstained with DAPI/antifade (Invitrogen; blue color in the staining) and cover-slipped. Sections were examined with a fluorescent microscope (EVOS FL, AMG).

Invasion Assay—

Assays were done in triplicate in invasion chambers pre-coated with reduced growth factor matrix from BD Biosciences. Cells were added to the upper chamber in 200 mL of serum-free medium. For the invasion assay, 20,000 cancer cells were seeded on the coated chamber, and the lower chamber was filled with 600 mL of medium (Cambrex) with FBS. After 37 hours of incubation, the cells on the underside of the upper chambers were stained with the blue stain in the Cell Invasion Assay Kit (Chemicon; cat. #ECM550) and counted using light microscopy.

Normal Breast Derived Cell Implantation into the Cleared Fatpads of NOD-SCID Mice—

Three-week-old female NOD-SCID mice were anesthetized by an i.p. injection[16]. The no. 4 inguinal mammary glands were cleared and humanized with 2.5×10$^5$ non-irradiated telomerase immortalized human mammary fibroblasts (a generous gift from John Stingl and Connie Eaves, Terry Fox Laboratory, Vancouver, British Columbia, Canada) and 2.5×10$^5$ irradiated (4 Gy) fibroblasts as previously described[16]. A 60-day release estrogen pellet (0.18 mg/pellet, Innovative Research of America, Sarasota, Fla.) was placed s.c. on the back of the neck of the mouse by using a trocar, and the sorted cells were mixed with 2.5×10$^5$ normal human mammary fibroblasts and resuspended in 50 ul of 1:1 Matrigel: 5% serum Ham's F-12 and injected into each of the cleared fat-pads. All of the implantation experiments were repeated five times using cells from different patients with three mice implanted per patient sample.

Differentiating Culture Conditions—

Sorted single cell suspensions were plated on collagen-coated plates at a density of 2000 viable cells/10 cm diameter dish. Cells were grown in Ham's F-12 medium (GIBCO INVITROGEN) with 5% fetal bovine serum (FBS), 5 mg/ml insulin, 1 mg/ml hydrocortisone, 10 mg/ml cholera toxin (Sigma, St Louis, Mo., USA), 10 ng/ml epidermal growth factor (BD Biosciences), and 13 Pen/Strep/Fungizone Mix (GIBCO). Cells were fixed or collected for immunostaining after 12 days.

3-D Matrigel Culture—

3-D cultures in Matrigel were established as previously described[27]. Briefly, the sorted cells were suspended in 1 ml of BD Matrigel™ Matrix (Cat. 354234, BD Biosciences, Palo Alto, Calif.) and Ham's F-12 medium (BioWhittaker) with 5% serum at a ratio of 1:1, and plated 1 ml of the mixture into one well of 24-well cold plates and each group of cells was performed in quadruplicates. After the matrigel was solidified, 0.5 ml of Ham's F-12 medium (BioWhittaker) with 5% serum was added to the top of the matrigel. The experiments were repeated with cells derived from at least three different patients.

Statistical Analysis—

Results are presented as the mean±standard deviation (STDEV) for at least 3 repeated individual experiments for each group. Mean and STDEV was determined on the basis of an analysis of at least 3 replicates using Microsoft Excel. Statistical differences were determined by using ANOVA and Student's t test for independent samples. A value of P<0.05 was considered statistically significant.

Figure 15:
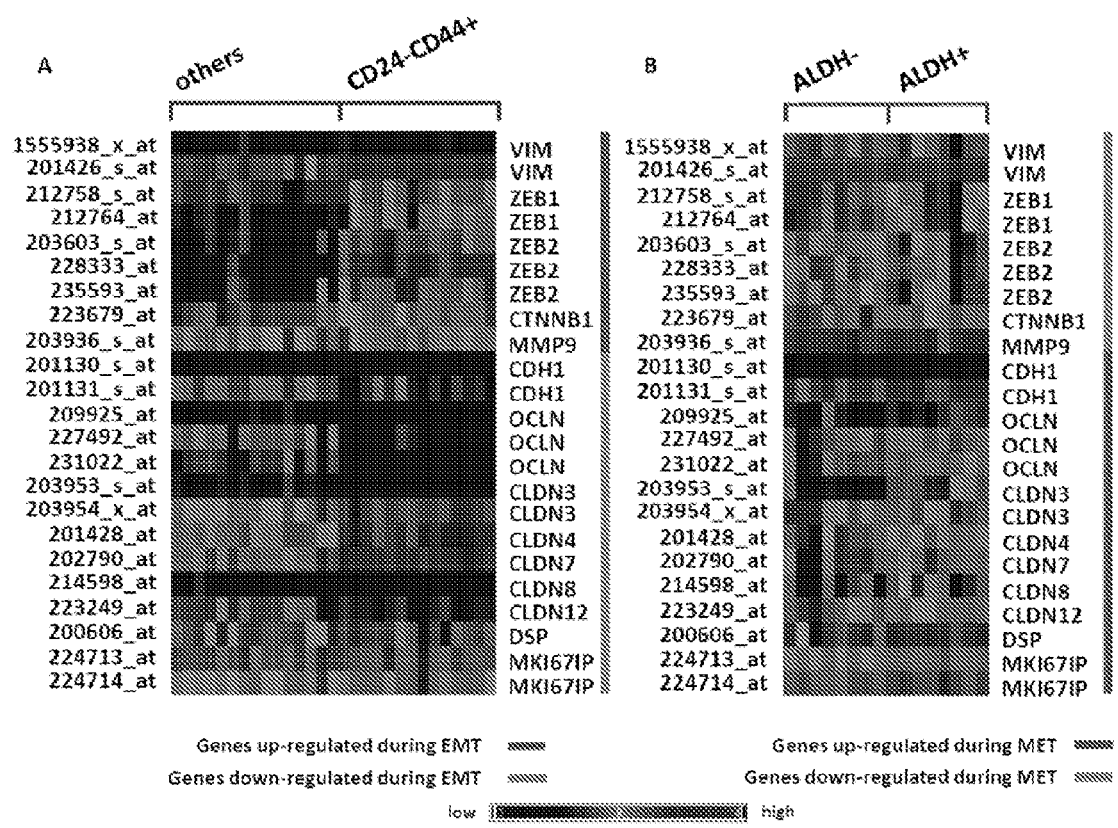
FIG. 15 shows that specific EMT markers have opposite expression patterns in CD24–CD44+ and ALDH+ cells. (A) For CD24–CD44+ vs. others flow-sorted profile datasets, heat map of EMT markers (|fold change|>1.5). (B) As with A but for ALDH+ vs. ALDH– profile datasets.

Results:

The expression of EMT and MET associated genes were compared in sorted CD24$^-$CD44$^+$ and ALDH$^+$ tumor cell populations. As shown in FIG. 10D and FIG. 15, EMT associated genes including vimentin, ZEB1, ZEB2, CTNNB1 and MMP9 were significantly enriched in the CD24$^-$CD44$^+$ populations while expression of these EMT genes were correspondingly decreased in the ALDH$^+$ populations. Conversely, genes associated with the alternative MET state such as cadherin, occludin, claudins and desmoplakin, were elevated in ALDH$^+$ populations and correspondingly diminished in the CD24$^-$CD44$^+$ cell populations. The proliferation marker Ki67 was preferentially expressed in ALDH$^+$ compared to CD24$^-$CD44$^+$ cells. These studies suggest that CD24$^-$CD44$^+$ primarily identifies EMT-like CSCs, whereas ALDH expression identifies MET-like proliferative CSCs. Importantly, these characteristics are independent of the molecular subtype of breast cancer. Previous studies have suggested that the relatively quiescent EMT-like CSCs may be particularly resistant to cytotoxic chemotherapy and radiation therapy[6]. This model is supported by a neo-adjuvant clinical trial which demonstrated that residual tumor cells in triple-negative breast cancer following chemotherapy or in luminal breast cancer following hormonal therapy express an EMT-like CSC profile[7], suggesting that these divergent molecular subtypes of breast cancer contain similar therapy resistant CSC populations.

Figure 10E:
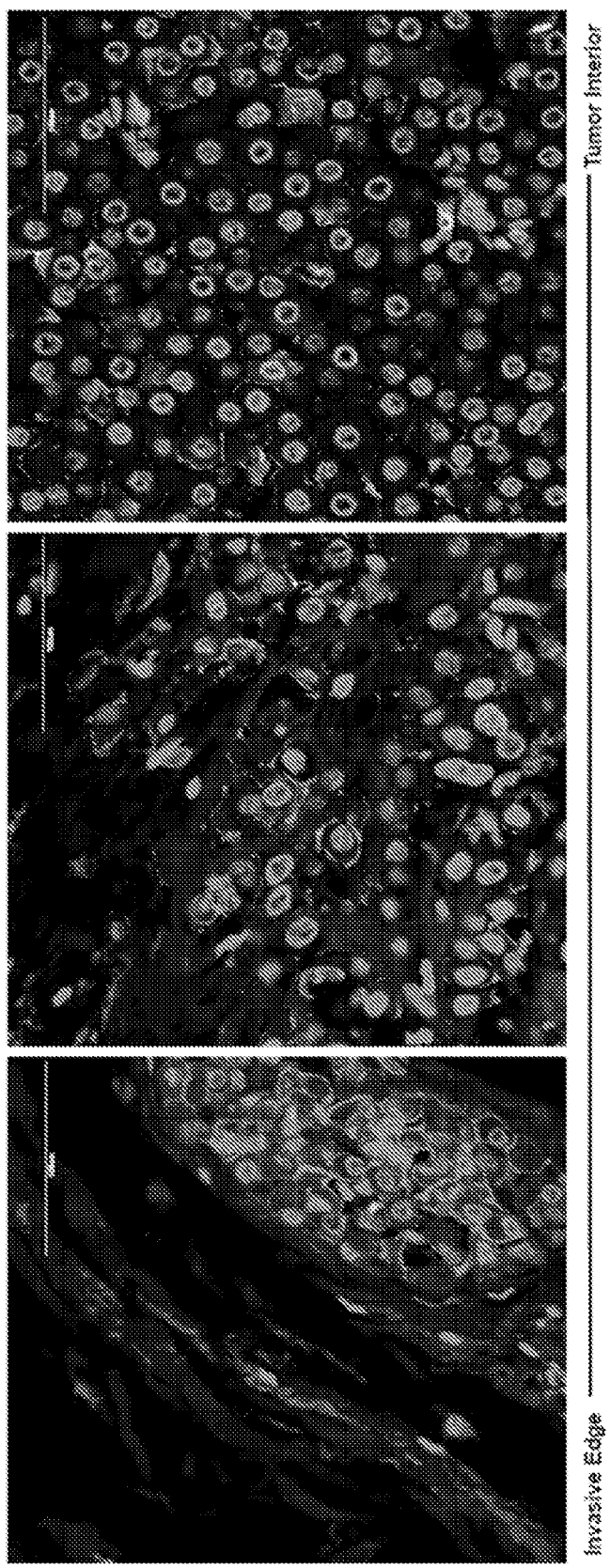

The above studies indicate that CD24⁻CD44⁺ and ALDH⁺ markers identify distinct CSC populations. To determine the location of these populations within tumors, immunofluorescence was performed utilizing antibodies against CD44, CD24 and ALDH1A1, the ALDH isoform most commonly expressed in human breast cancers[3]. As assessed by immunofluorescence, CD24⁻CD44⁺ and ALDH⁺ identify largely non-overlapping cell populations, an observation supported by flow cytometry analysis of isolated tumor cell populations. Furthermore, CD24⁻CD44⁺ cells were primarily located at the tumor invasive edge adjacent to stroma (FIG. 10E). In contrast, ALDH1A1⁺ cells were located more centrally consistent with previous studies demonstrating that ALDH⁺ CSC are generated by hypoxia in interior tumor zones[8] (FIG. 10E). A small subpopulation of cells were identified which simultaneously expressed CD24⁻CD44⁺ and ALDH⁺ (FIG. 10E) which may be indicative of CSC transitioning between epithelial and mesenchymal states.

Figure 11:
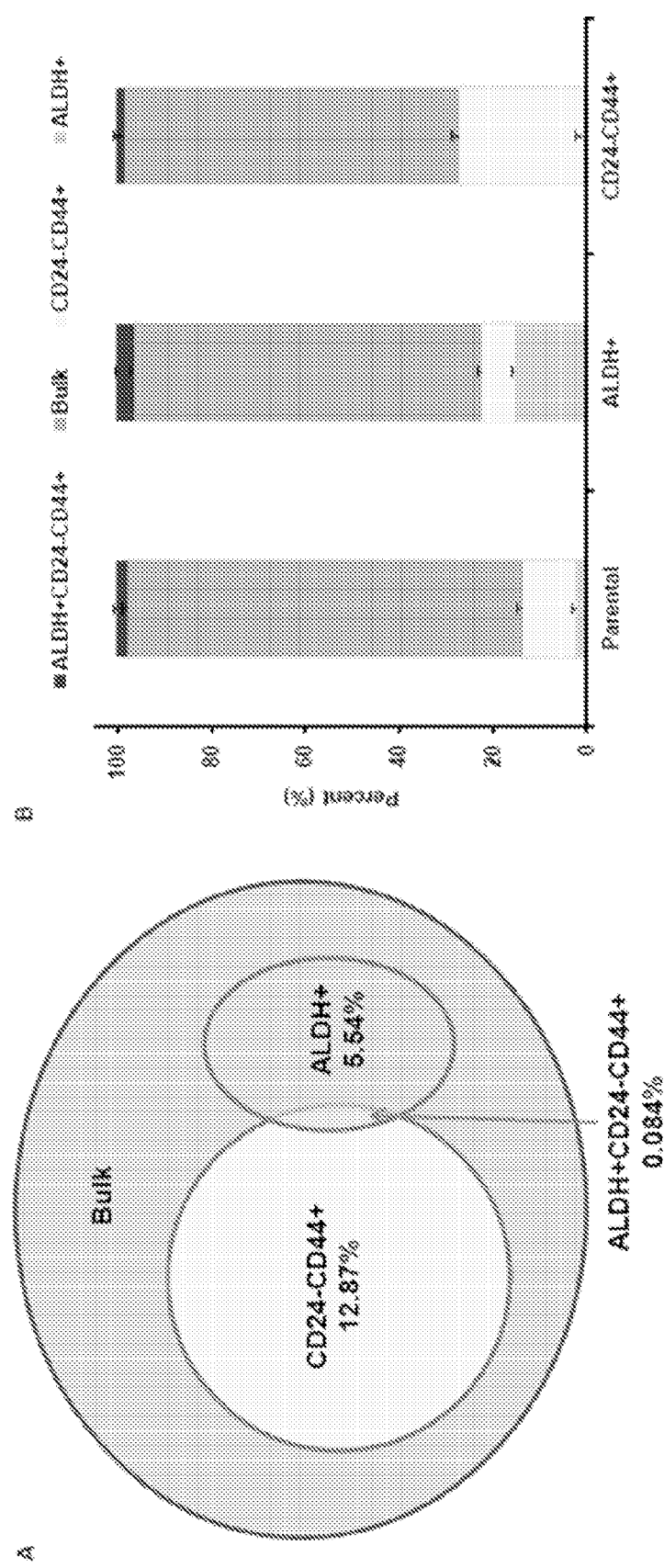
FIG. 11. Role of EMT-MET plasticity in tumor metastasis. Basal breast cancer cell line SUM149 was immunostained with CD24 and CD44 antibodies and subsequently with ALDEFLUOR. The four cell subpopulations defined by the ALDEFLUOR and CD24$^-$CD44$^+$ phenotypes were separated by FACS. (A) The percentages shown in the diagram show the representation of the cell subpopulations in the total tumor cell population and the overlap between the ALDEFLUOR phenotype and the CD24$^-$CD44$^+$ phenotype. (B) The unsorted SUM149 cells and the sorted CD24$^-$CD44$^+$ and ALDH$^+$ populations as described in (A) were placed in culture for 10 days and resulting cells were re-analyzed by FACS for ALDEFLUOR, CD24, CD44. (C) The sorted four populations from (A) were accessed for invasive capacity utilizing the matrigel invasion assay. (D-E) Hypothetical models show the characteristics of two different states of breast cancer stem cells and their metastatic potential. * P<0.05; Error bars represent mean±STDEV.
Figure 11:
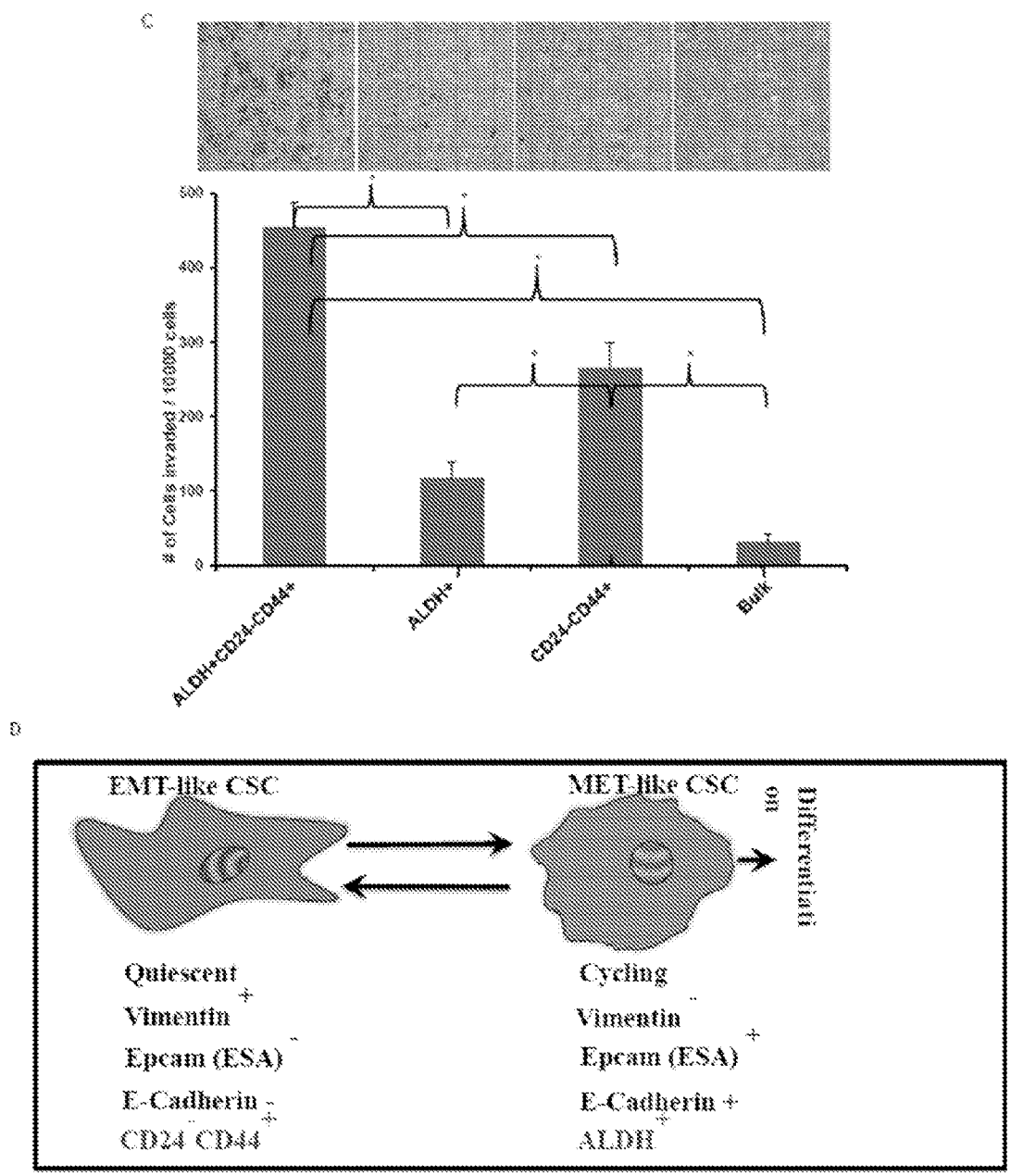
Figure 11:
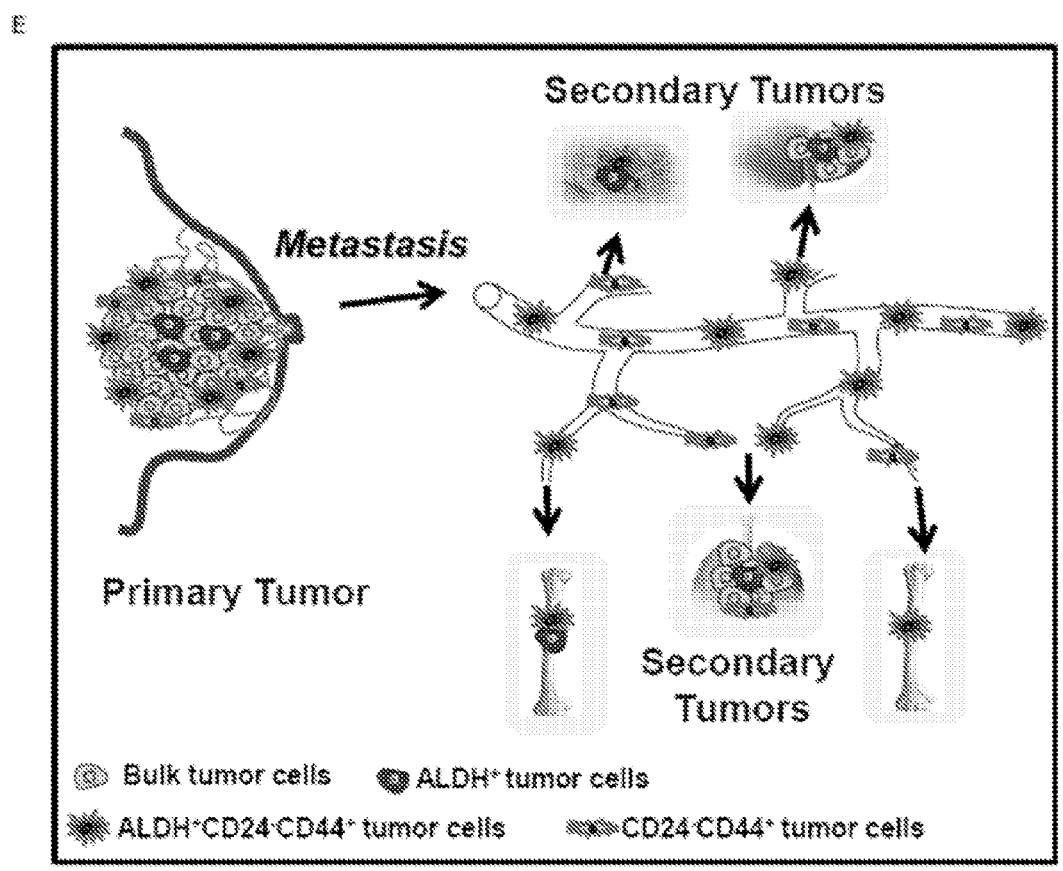
Figure 17:
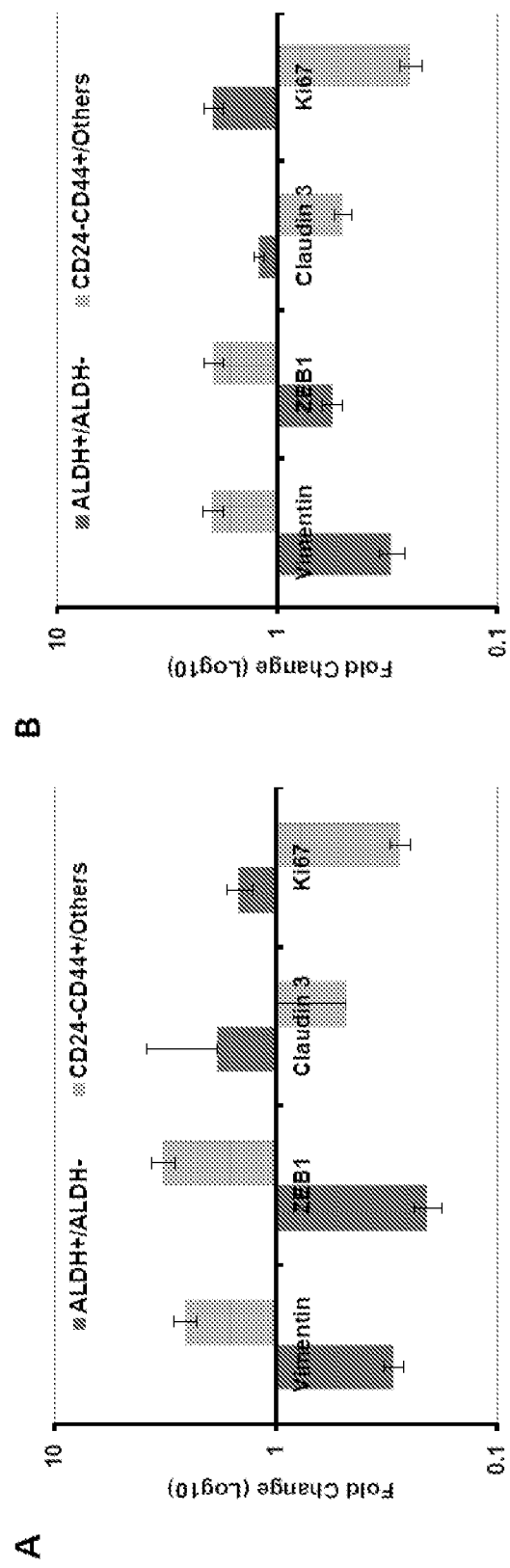
FIG. 17 shows validation of gene expression results by qRT-PCR. To confirm gene expression results for EMT/MET markers, the mRNA expression level for Vimentin, ZEB1, Claudin 3 and ki67 were measured in SUM149 cells. (A) and primary xenograft MC1 (B) sorted for ALDH+/ALDH–, CD24–CD44+/others by qRT-PCR. Gene expression levels measured by qRT-PCR confirm the results obtained with affymatrix array Hu133 plus2.0. Error bars represent mean±STDEV.

To further characterize the biological characteristics of these CSC populations, established breast cancer cell lines were utilized as well as primary tumor xenografts. As was the case with primary tumors, breast cancer cell lines and primary xenografts contained CD24⁻CD44⁺ and ALDH⁺ expressing cell populations with a minimal overlap (FIG. 11A). Furthermore, as was the case with primary breast cancers, CD24⁻CD44⁺ cells were enriched for expression of mesenchymal associated genes, while ALDH⁺ cells demonstrated a reciprocal epithelial gene expression pattern (FIG. 16). These results were confirmed by qRT-PCR (FIG. 17). To determine the degree of cellular plasticity between the epithelial and mesenchymal CSC states, CD24⁻CD44⁺ and ALDH⁺ populations were cultured, and the stability of the phenotypes was determined. As demonstrated in FIG. 11B, in basal SUM149 cells, stem cell states were plastic in vitro and each enriched CSC population readily generated the other, resulting in cell populations which recapitulated those present in the original cell line (FIG. 11B). This suggests that CSCs can transit between epithelial and mesenchymal states.

Matrigel invasion assay was utilized to determine the relationship between CSC states and tumor invasion. As shown in FIG. 11C, tumor cells displaying either stem cell marker were more invasive than the bulk tumor population. Within CSC marker positive cells, CD24⁻CD44⁺ cells were significantly more invasive than ALDH⁺ cells with while cells displaying all three stem cell markers demonstrated the greatest invasive capacity.

Together, these studies suggest that CSCs exist in alternative EMT and MET-like states. The EMT-like state characterized as CD24⁻CD44⁺ displays a mesenchymal phenotype with increased invasive capacity, and low proliferative potential. Conversely, the MET-like state characterized by ALDH expression displays an epithelial morphology and exhibits increased self-renewal capacity (FIG. 11D). Transition between these states may be regulated by extrinsic signals generated in the tumor microenvironment. Cellular plasticity allowing transition between EMT and MET states may be required for tumors to successfully navigate the metastatic cascade as illustrated in FIG. 11E.

Figure 12A:
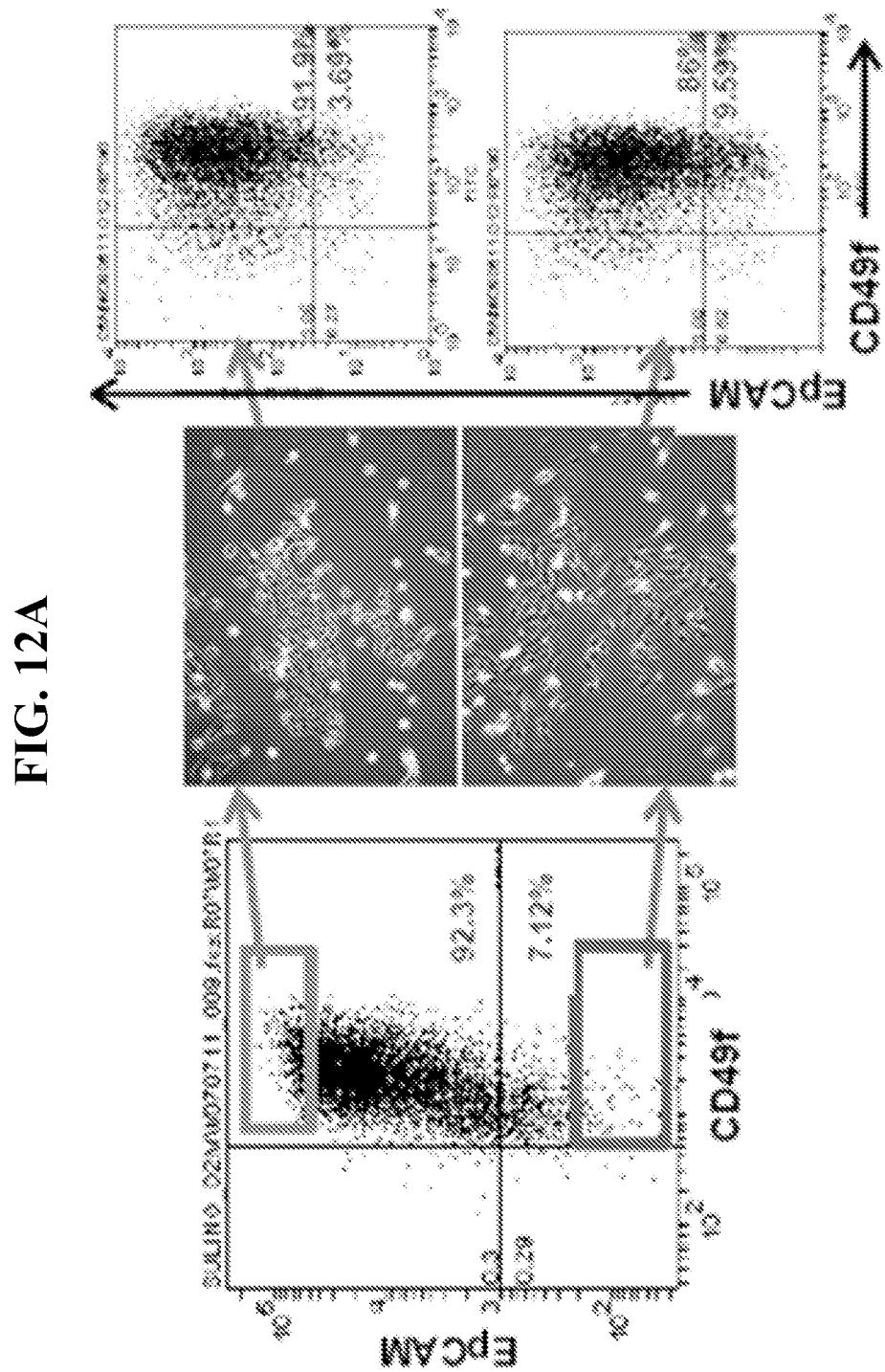
FIG. 12. Identification of EMT-MET states in non-transformed MCF10A cells. (A) Cells were immunostained utilizing EpCAM and CD49f antibodies, EpCAM$^+$CD49f$^+$ and EpCAM$^-$CD49f$^+$ cells separated by FACS and plated in culture for 10 days. FACS analysis for EpCAM and CD49f was then repeated. (B-C) Total RNA was extracted from the sorted EpCAM$^+$CD49f$^+$ cells and EpCAM$^-$CD49f$^+$ cells, and the expression level of E-Cadherin, Vimention and TBP was measured by qRT-PCR. (D) Cells were immunostained with EpCAM and CD49f antibodies, and subsequently stained with CD24/CD44 or ALDEFLUOR. (E) Cells were immunostained with CD24 and CD44 antibodies and subsequently with ALDEFLUOR. The four cell subpopulations defined by the ALDEFLUOR and CD24$^-$CD44$^+$ phenotypes were separated by FACS. The percentages shown in the diagram depict cell subpopulations and the overlap between the ALDEFLUOR-positive phenotype and the CD24$^-$CD44$^+$ phenotype. (F) Total RNA was extracted from the four populations as described in (E) and used for Affymatrix array (Hu133 plus 2.0) analysis. The fold change for EMT/MET markers was compared between ALDH$^+$ and ALDH$^-$, CD24$^-$CD44$^+$ and others. * P<0.05; Error bars represent mean±STDEV.
Figure 12:
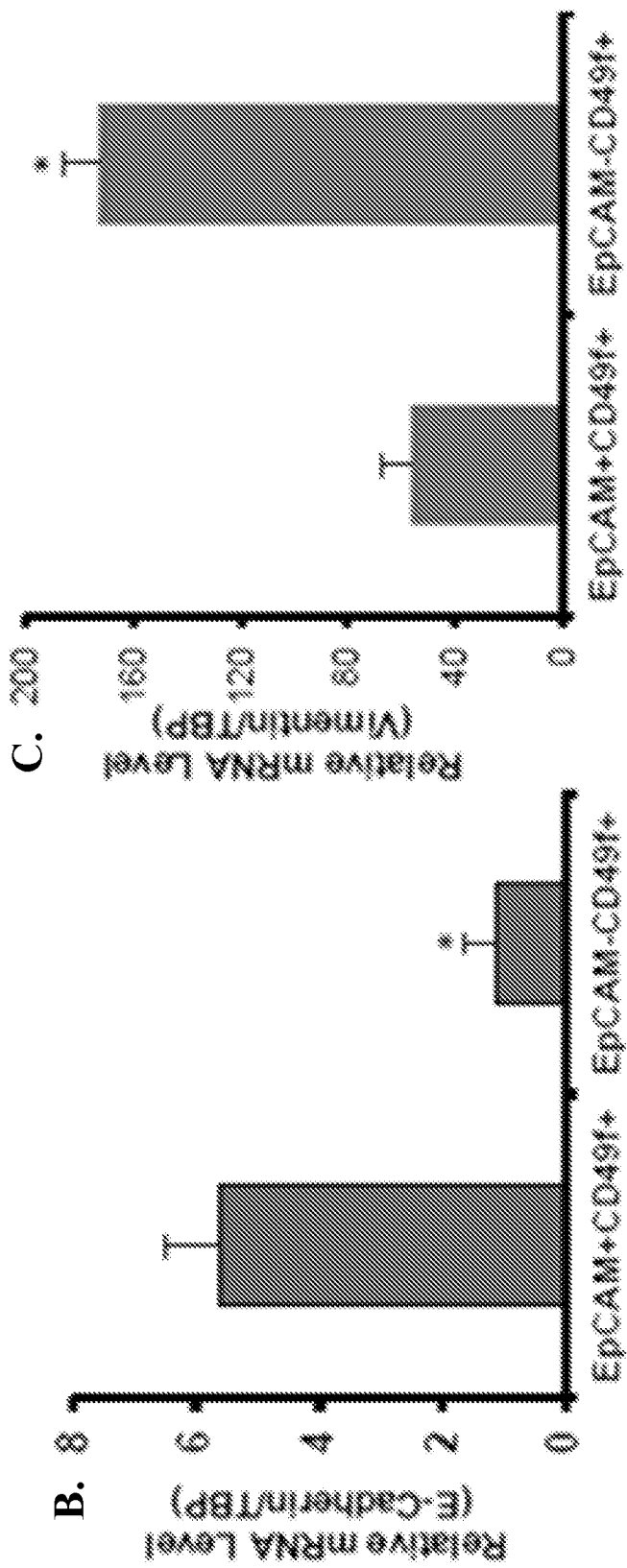
Figure 12D:
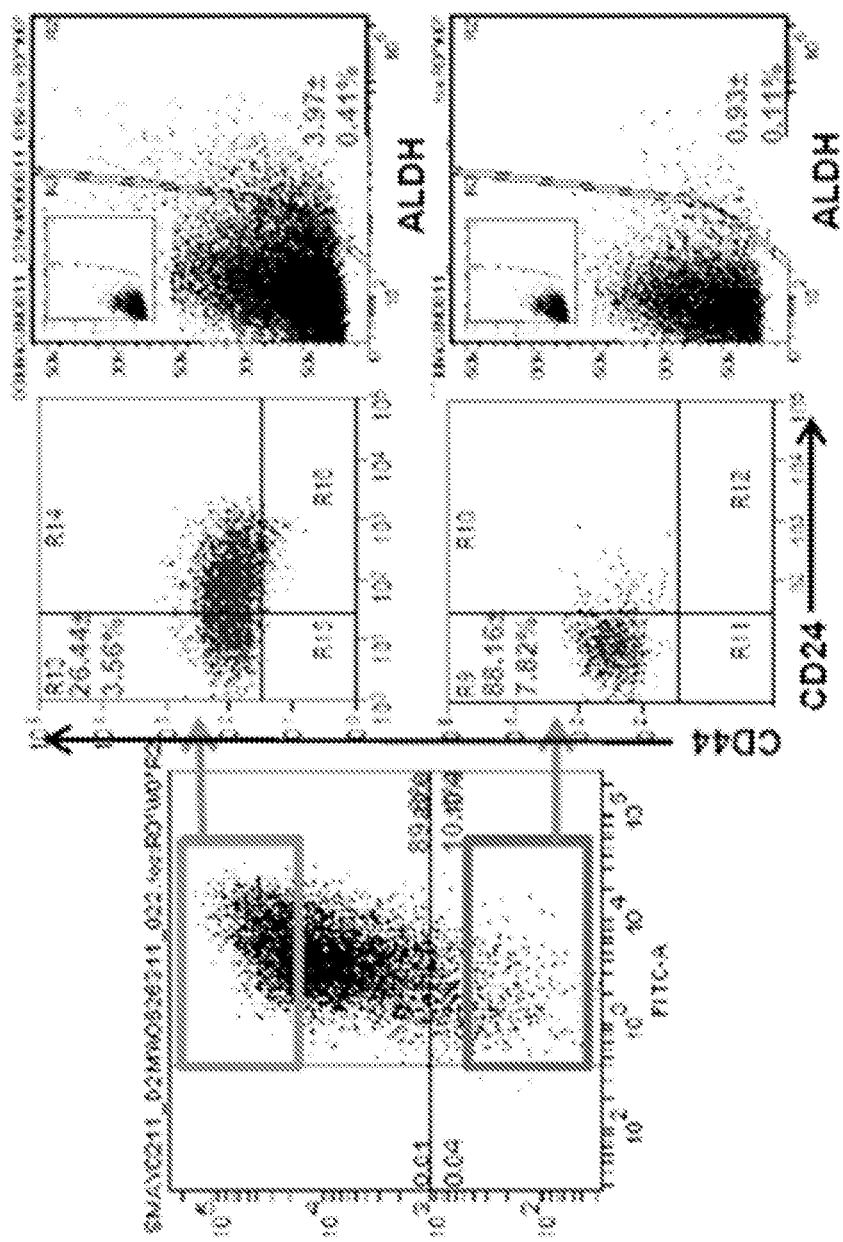
Figure 12:
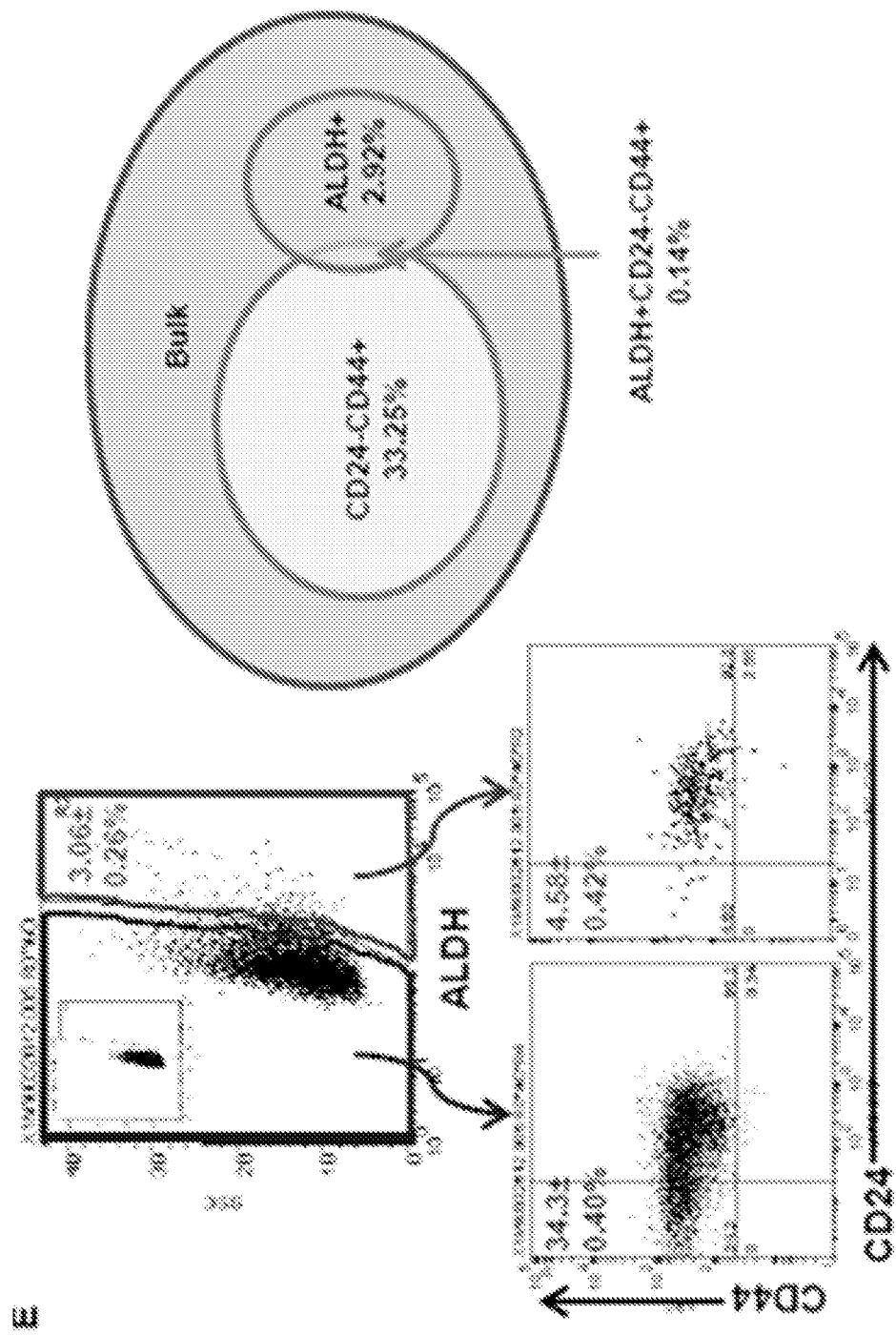
Figure 18:
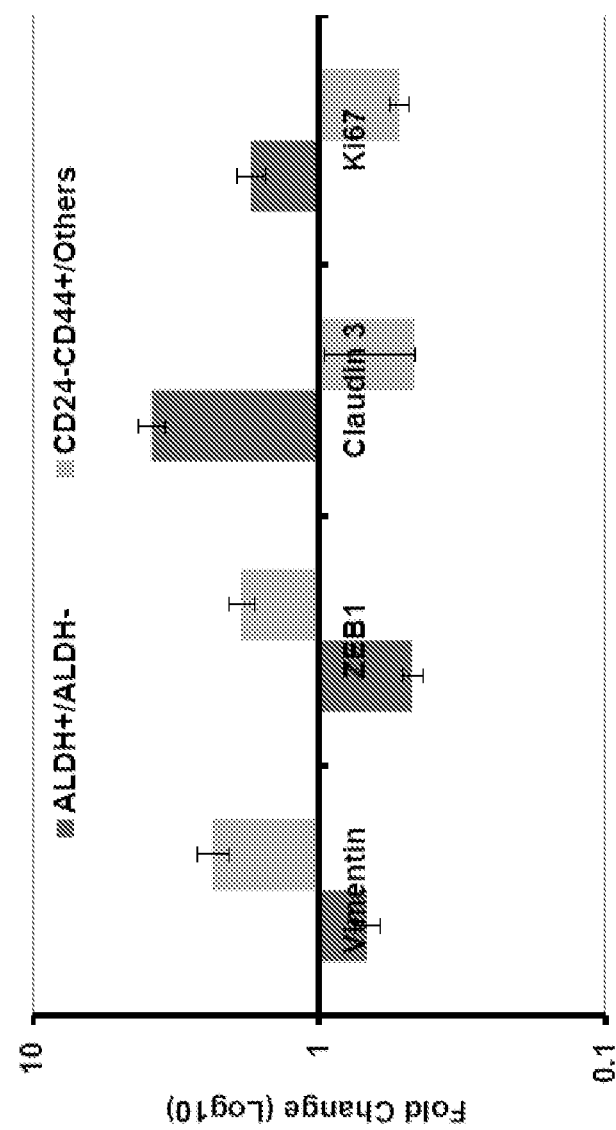
FIG. 18 shows results of validation of gene expression results by qRT-PCR. To confirm gene expression results for EMT/MET markers, mRNA expression level for Vimentin, ZEB1, Claudin 3 and ki67 were measured in MCF10A cells sorted for ALDH+/ALDH−, CD24−CD44+/others by qRT-PCR. Gene expression levels measured by qRT-PCR confirm the results obtained using DNA. Error bars represent mean±STDEV.

The relationship between CSC populations and their counterparts in the normal mammary gland remains controversial. A hierarchy of normal mammary cells has been described based on the expression of markers CD49f (alpha 6 integrin) and EpCAM[13]. These markers identify four populations in the normal mammary gland including EpCAM⁺CD49f epithelial cells, EpCAM⁺CD49f⁺ luminal progenitor cells, EpCAM⁻CD49f⁺ stem cells and EpCAM⁻CD49f⁻ stromal cells[13]. The non-transformed MCF10A human mammary cell line was utilized to determine the relationship between these markers and the CD24⁻CD44⁺ and ALDH⁺ markers used to characterize CSCs. As previously reported[14,15], when placed in tissue culture, EpCAM⁺CD49f⁺ cells displayed an epithelial morphology (FIG. 12A) and expressed E-cadherin (FIG. 12B), while EpCAM⁻CD49f⁺ cells displayed a mesenchymal morphology (FIG. 12A) and expressed the EMT marker vimentin (FIG. 12C). However, these phenotypes were not stable in culture and EpCAM⁺CD49f⁻ cells generated double-positive cells and vice versa (FIG. 12A). To determine the relationship between cell populations identified by expression of the markers and those expressing CSC markers CD24⁻CD44⁺ and ALDH⁺, serial flow cytometry using both sets of markers was performed. EpCAM⁻CD49f⁺ mesenchymal-like cells were enriched for the expression of CD24⁻CD44⁺ (FIG. 12D), whereas the EpCAM⁺CD49f⁺ epithelial-like cells were enriched for ALDH expression (FIG. 12D). Furthermore, these populations were distinct with little overlap (FIG. 12E). Gene expression analysis of sorted CD24⁻CD44⁺ and ALDH⁺ populations demonstrated that these cells expressed genes characteristic of mesenchymal (basal) and epithelial phenotypes respectively (FIG. 12F). Expression of a subset of these genes was verified by qRT-PCR (FIG. 18).

Figure 13:
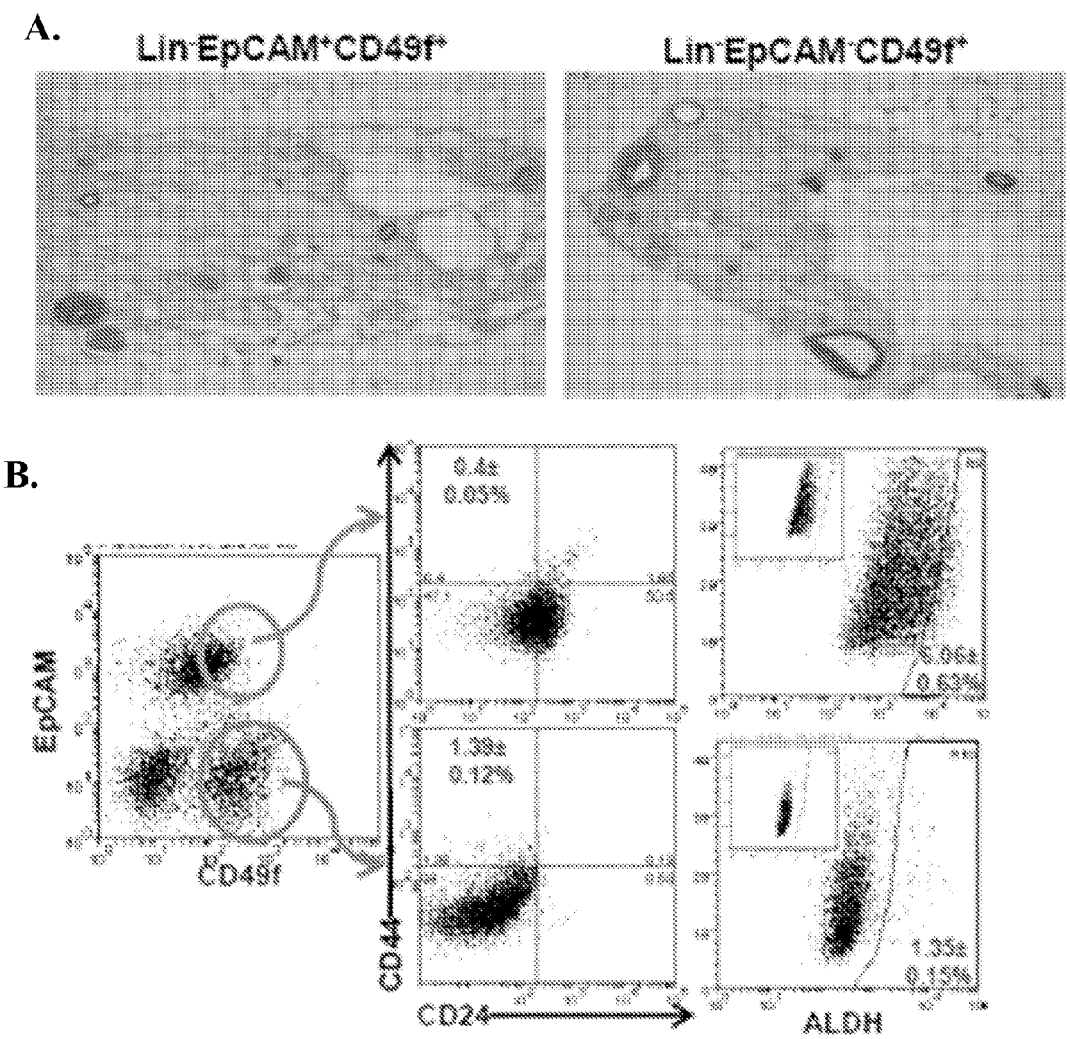
FIG. 13. Normal human breast contained distinct basal and luminal stem cells which express EMT/MET markers respectively. (A) Cells isolated from reduction mammoplasty tissue were immunostained with Lineage markers (Lin$^-$), EpCAM and CD49f antibodies, and were first gated based on viability (DAPI$^-$) and lineage markers. The sorted cells (Lin$^-$EpCAM$^+$CD49f$^+$ cells and Lin$^-$EpCAM$^-$CD49f$^+$ cells) were injected into the $4^{th}$ mammary gland fatpads which were previously humanized with normal human breast fibroblasts. After about 2 months, mice were sacrificed and the outgrowths generated in the fatpads were accessed by Hematoxylin and eosin staining (B) Cells were immunostained with EpCAM and CD49f antibodies, followed by CD24/CD44 or ALDEFLUOR. (C) Cells were immunostained with Lineage markers (Lin$^-$), EpCAM and CD49f antibodies, and subsequently with ALDEFLUOR. The cells were first gated based on viability (DAN) and lineage markers. The sorted cells (Lin$^-$EpCAM$^+$CD49f$^+$ ALDH$^+$ cells and Lin$^-$EpCAM$^+$CD49f$^+$ ALDH$^-$ cells) were grown in differentiating conditions on collage-coated plates for 12 days and the number of colonies generated was accessed. (D) Sorted cells (Lin$^-$EpCAM$^+$CD49f$^+$ ALDH$^+$ cells and Lin$^-$EpCAM$^+$CD49f$^+$ ALDH$^-$ cells) were cultured in 3D Matrigel culture for 3 weeks and the number of branched structures generated were accessed. (E) Localization of CD24 (Magenta), CD44 (Green), ALDH1 (Red), and DAPI (Blue) in normal breast tissue as accessed by immunofluorescence staining. Yellow arrow, CD24$^-$CD44$^+$ cells; Red arrow, ALDH1$^+$ cells. Bar, 100 um.
Figure 13:
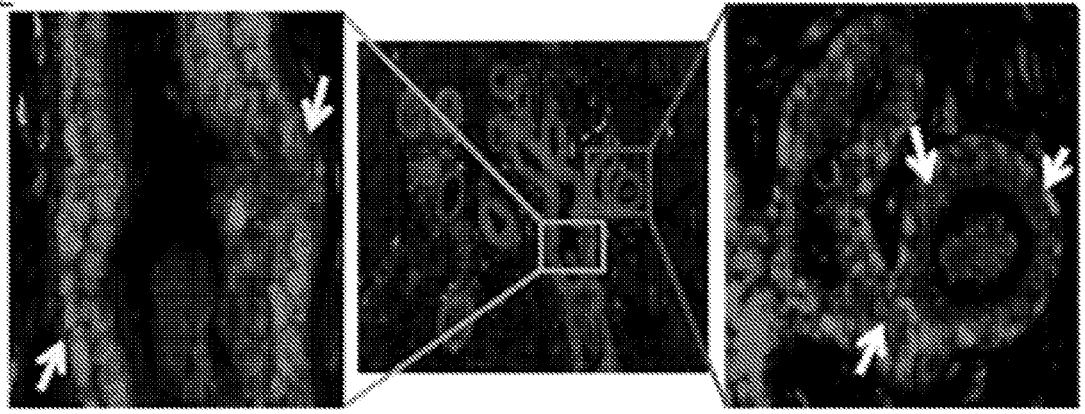

Next, the expression of these markers was examined in normal human mammary cell populations isolated from reduction mammoplasties. As was the case for MCF10A cells, the normal mammary gland contains cell populations that can be identified by virtue of CD49f and EpCAM expression. EpCAM⁻CD49f⁺ cells expressed basal/mesenchymal markers, whereas EpCAM⁺CD49f⁺ cells primarily expressed epithelial markers (data not shown). To determine the differentiation potential of these cells they were transplanted into the cleared fat pads of NOD/SCID mice that had been humanized by addition of human mammary stromal cells[16]. Within the CD49f⁺ population, both EpCAM⁺ and EpCAM⁻ cells were able to generate mammary structures containing both epithelial and myoepithelial cell layers (FIG. 13A). To further characterize these populations, the relationship between expression of CD49f and EpCAM with that of CD24⁻CD44⁺ and ALDH⁺ was determined.

Figure 19:
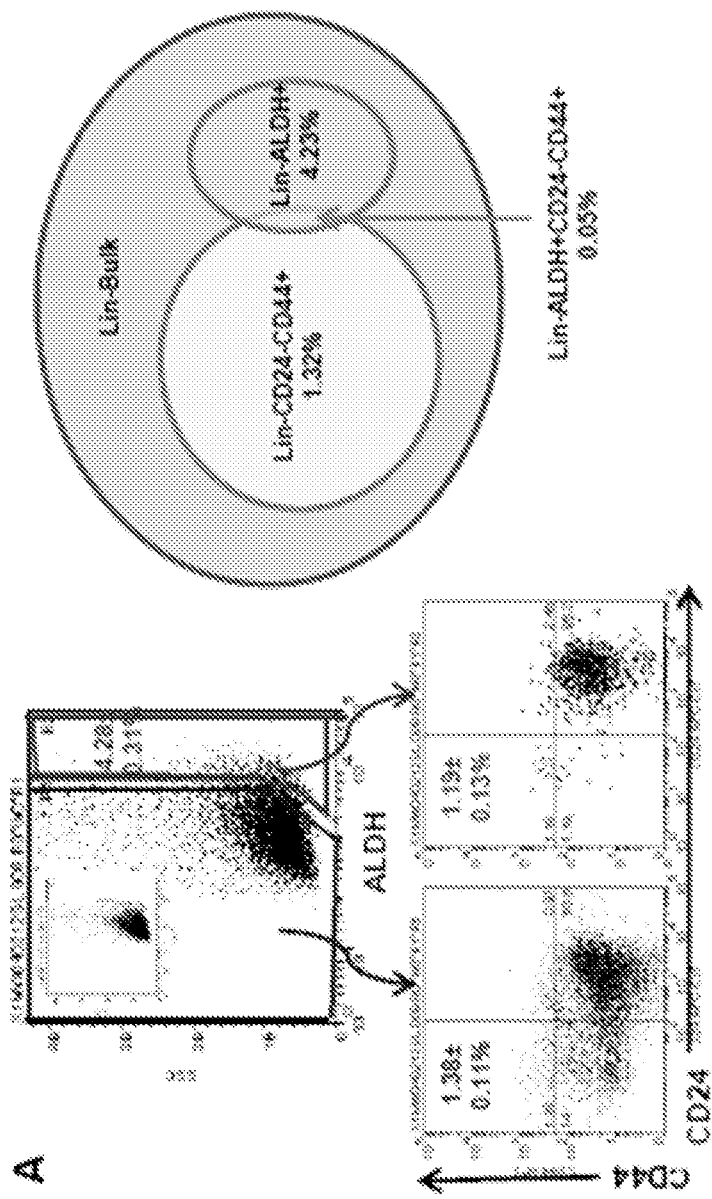
FIG. 19 shows results of characterization of CD24−CD44+ cells and ALDH+ epithelial cells isolated from normal breast tissues. (A) Cells were immunostained with CD24 and CD44 antibodies and were subsequently stained with ALDE-FLUOR. The four cell subpopulations defined by the ALDE-FLUOR and CD24−CD44+ phenotypes were separated by FACS. The percentages in the diagram represent the cell subpopulations as a representative of the total tumor cell population and the overlap between the ALDEFLUOR phenotype and the CD24−CD44+ phenotype. (B) Expression of EMT/MET markers in CD24−CD44+ vs. others and ALDH+ vs. ALDH− of normal breast as accessed by Affymatrix array Hu133 plus2.0. (C) To confirm gene expression results for EMT/MET markers, the mRNA expression level for Vimentin, ZEB1, Claudin 3 and ki67 were measured in a set of breast tumor cells sorted for ALDH+/ALDH−, CD24−CD44+/others by qRT-PCR. Gene expression levels measured by qRT-PCR confirm the results obtained with affymatrix array Hu133 plus2.0. Error bars represent mean±STDEV.
Figure 20:
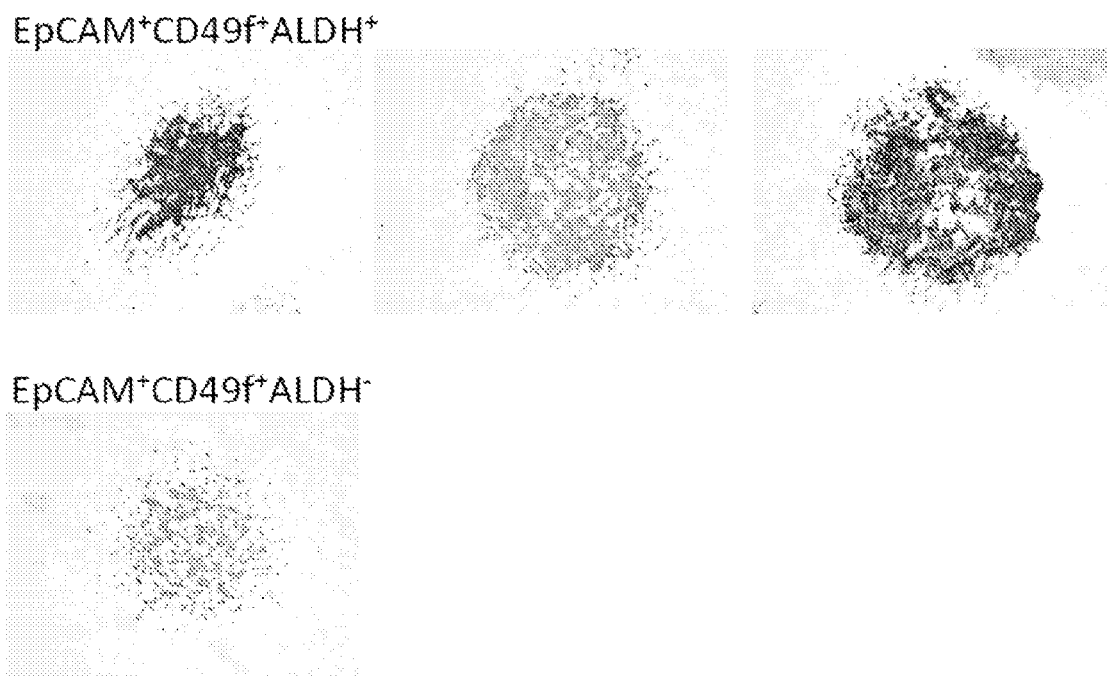
FIG. 20 shows results regarding evaluation of the differentiation potential of Lin−EpCAM+CD49f+ALDH+ cells and Lin−EpCAM+CD49f+ALDH− cells isolated from normal breast tissue. Primary cells isolated from reduction mammoplasties were immunostained with Lineage markers (Lin−), EpCAM and CD49f antibodies, and were subsequently stained with ALDEFLUOR. The cells were first gated based on viability (DAPI−) and lineage markers. The sorted cells (Lin−EpCAM+CD49f+ALDH+ cells and Lin−EpCAM+CD49f+ALDH− cells) were grown in differentiating conditions on collage-coated plates for 12 days and the grown colonies were stained by IHC with lineage-specific markers (ck14-Purple, ck18-Red).

As was the case with MCF10A cells, EpCAM⁻CD49f⁺ cells were enriched for CD24⁻CD44⁺, whereas EpCAM⁺CD49f⁺ cells were enriched for ALDH expression (FIG. 13B) with little overlap between these populations (FIG. 19A). Gene expression analysis of sorted CD24⁻CD44⁺ and ALDH⁺ cells demonstrated that these cell populations expressed genes characteristic of mesenchymal (basal) and epithelial phenotypes respectively (FIG. 19B), findings which were verified by qRT-PCR (FIG. 19C). Despite the observation that ALDH⁺ cells were predominantly contained within the EpCAM⁺CD49f⁺ population, this ALDH⁺ population constituted only 6% of total EpCAM⁺CD49f⁺ cells. Furthermore, within the EpCAM⁺CD49f⁺ population, only Aldefluor-positive cells were able to generate bi-lineage colonies in vitro (FIG. 13C and FIG. 20), and multilineage ductal/alveolar in 3D matrigel cultures (FIG. 13D and FIG. 21), consistent with a recent report[17]. These experiments indicate that in the normal mammary gland, the EpCAM⁺CD49f⁺ cell population is heterogeneous and is composed of an ALDH⁺ subcomponent which has high proliferative capacity as well as multilineage differentiation potential and an ALDH-negative component which is luminal restricted with lower proliferative potential.

To determine the cellular location of these populations in the normal mammary gland, immunofluorescence staining was performed utilizing antibodies against CD44, CD24 and ALDH1A1. CD24⁻CD44⁺ cells were located in the basal cell layer in ductal structures, whereas ALDH⁺ cells were located in a luminal location in the terminal end buds and at ductal branch points (FIG. 13E).

Work conducted during this example suggests that human mammary glands display an organization where basal stem cells are CD24⁻CD44⁺, EpCAM⁻CD49f⁺, and where luminal stem cells are ALDH⁺EpCAM⁺CD49f⁺. The self-renewing proliferative state of the ALDH⁺ luminal stem cells may increase their susceptibility to mutation during carcinogenesis. ALDH⁺ luminal breast stem cells may, therefore, represent a subset of EpCAM⁺CD49f⁺ cells capable of giving rise to breast cancers. Furthermore, the observation that different molecular subtypes of breast cancer contain stem cells with similar molecular characteristics suggests that these subtypes may share a common cell of origin. The mutation profile, therefore, rather than the cell of origin may determine the molecular subtype of breast cancer generated. This model is supported by recent whole genome analysis of breast cancers which reveal distinct mutations associated with different molecular subtypes which intern display distinct biological and clinical behaviors[22]. This Example also indicates that EpCAM⁺CD49f⁺ cells which have been previously characterized as luminal progenitors, in fact represents a heterogenous population that contains an ALDH⁺ subpopulation that is more accurately characterized as a luminal stem cell. The tumor initiating potential of cancer cells with this phenotype and the multilineage differentiation capacity of their normal counterparts supports this classification. This Example further indicates that once tumors develop they are driven by CSC with the cellular plasticity to transition between EMT and MET states. These CSC states transitions may facilitate tumor invasion as well as growth at metastatic sites.

REFERENCES 1. (eds). SEER Cancer Statistics Review, 1975-2007, National Cancer Institute. Bethesda, Md., http://seer.cancer.gov/csr/1975_2007/, based on November 2009 SEER data submission, posted to the SEER web site, 2010.
2. Berry D A, Cronin K A, Plevritis S K, Fryback D G, Clarke L, Zelen M, Mandelblatt J S, Yakovlev A Y, Habbema J D, Feuer E J: Effect of screening and adjuvant therapy on mortality from breast cancer. The New England journal of medicine 2005, 353(17):1784-1792.
3. Al-Hajj M, Wicha M S, Benito-Hernandez A, Morrison S J, Clarke M F: Prospective identification of tumorigenic breast cancer cells. Proc Natl Acad Sci USA 2003, 100(7): 3983-3988.
4. Dontu G, Abdallah W, Foley J, Jackson K, Clarke M, Kawamura M, Wicha M: In vitro propagation and transcriptional profiling of human mammary stem/progenitor cells. Genes & Development 2003, 17(10):1253-1270.
5. Ginestier C, Hur M, Charafe-Jauffret E, Monville F, Dutcher J, Brown M, Jacquemier J, Viens P, Kleer C G, Schott A et al: ALDH1 is a marker of normal and malignant breast stem cells and a predictor of poor clinical outcome. Cell Stem Cell 2007, 1:555-567.
6. Dontu G, Al-Hajj M, Abdallah W M, Clarke M F, Wicha M S: Stem cells in normal breast development and breast cancer. Cell Prolif 2003, 36 Suppl 1:59-72.
7. Ginestier C, Hur M H, Charafe-Jauffret E, Monville F, Dutcher J, Brown M, Jacquemier J, Viens P, Kleer C G, Liu S et al: ALDH1 is a marker of normal and malignant human mammary stem cells and a predictor of poor clinical outcome. Cell Stem Cell 2007, 1(5):555-567.
8. Charafe-Jauffret E, Ginestier C, Iovino F, Wicinski J, Cervera N, Finetti P, Hur M H, Diebel M E, Monville F, Dutcher J et al: Breast cancer cell lines contain functional cancer stem cells with metastatic capacity and a distinct molecular signature. Cancer Res 2009, 69(4):1302-1313.
9. Korkaya H, Paulson A, Charafe-Jauffret E, Ginestier C, Brown M, Dutcher J, Clouthier S G, Wicha M S: Regulation of mammary stem/progenitor cells by PTEN/Akt/beta-catenin signaling. PLoS Biol 2009, 7(6):e1000121.
10. Phillips T M, McBride W H, Pajonk F: The response of CD24(-/low)/CD44+ breast cancer-initiating cells to radiation. J Natl Cancer Inst 2006, 98(24):1777-1785.
11. Shafee N, Smith C R, Wei S, Kim Y, Mills G B, Hortobagyi G N, Stanbridge E J, Lee E Y: Cancer stem cells contribute to cisplatin resistance in Brca1/p53-mediated mouse mammary tumors. Cancer Res 2008, 68(9):3243-3250.
12. Li C, Heidt D G, Dalerba P, Burant C F, Zhang L, Adsay V, Wicha M, Clarke M F, Simeone D M: Identification of pancreatic cancer stem cells. Cancer Res 2007, 67(3): 1030-1037.
13. Tanei T, Morimoto K, Shimazu K, Kim S J, Tanji Y, Taguchi T, Tamaki Y, Noguchi S: Association of breast cancer stem cells identified by aldehyde dehydrogenase 1 expression with resistance to sequential Paclitaxel and epirubicin-based chemotherapy for breast cancers. Clin Cancer Res 2009, 15(12):4234-4241.
14. Lund E, Guttinger S, Calado A, Dahlberg J E, Kutay U: Nuclear export of microRNA precursors. Science 2004, 303(5654):95-98.
15. Lewis B P, Burge C B, Bartel D P: Conserved seed pairing, often flanked by adenosines, indicates that thousands of human genes are microRNA targets. Cell 2005, 120(1):15-20.
16. Kato M, Slack F J: microRNAs: small molecules with big roles—C. elegans to human cancer. Biol Cell 2008, 100 (2):71-81.
17. Lowery A J, Miller N, McNeill R E, Kerin M J: MicroRNAs as prognostic indicators and therapeutic targets: potential effect on breast cancer management. Clin Cancer Res 2008, 14(2):360-365.
18. Wiemer E A: The role of microRNAs in cancer: no small matter. Eur J Cancer 2007, 43(10):1529-1544.
19. Hatfield S, Ruohola-Baker H: microRNA and stem cell function. Cell Tissue Res 2008, 331(1):57-66.
20. Croce C M, Calin G A: miRNAs, cancer, and stem cell division. Cell 2005, 122(1):6-7.
21. Yu F, Yao H, Zhu P, Zhang X, Pan Q, Gong C, Huang Y, Hu X, Su F, Lieberman J et al: let-7 regulates self renewal and tumorigenicity of breast cancer cells. Cell 2007, 131(6): 1109-1123.
22. Yu F, Yao H., Zhu P., Zhang X., Pan Q., Gong C., Huang Y., Hu X., Su F., Lieberman J. and Song E.: let-7 regulates self-renewal and tumorigenicity of breast cancer cells. Cell 2007, 131:1109-1123.
23. Silber J, Lim D A, Petritsch C, Persson A I, Maunakea A K, Yu M, Vandenberg S R, Ginzinger D G, James C D, Costello J F et al: miR-124 and miR-137 inhibit proliferation of glioblastoma multiforme cells and induce differentiation of brain tumor stem cells. BMC Med 2008, 6:14.
24. Ji J, Yamashita T, Budhu A, Forgues M, Jia H L, Li C, Deng C, Wauthier E, Reid L M, Ye Q H et al: Identification of microRNA-181 by genome-wide screening as a critical player in EpCAM-positive hepatic cancer stem cells. Hepatology 2009, 50(2):472-480.
25. Liu C, Kelnar K, Liu B, Chen X, Calhoun-Davis T, Li H, Patrawala L, Yan H, Jeter C, Honorio S et al: The 25. microRNA miR-34a inhibits prostate cancer stem cells and metastasis by directly repressing CD44. Nat Med 2011, 17(2):211-215.
26. Ibarra I, Erlich Y, Muthuswamy S K, Sachidanandam R, Hannon G J: A role for microRNAs in maintenance of mouse mammary epithelial progenitor cells. Genes Dev 2007, 21(24):3238-3243.
27. Greene S B, Gunaratne P H, Hammond S M, Rosen J M: A putative role for microRNA-205 in mammary epithelial cell progenitors. J Cell Sci 2010, 123(Pt 4):606-618.
28. Shimono Y, Zabala M, Cho R W, Lobo N, Dalerba P, Qian D, Diehn M, Liu H, Panula S P, Chiao E et al: Downregulation of miRNA-200c links breast cancer stem cells with normal stem cells. Cell 2009, 138(3):592-603.
29. Yu F, Deng H, Yao H, Liu Q, Su F, Song E: Mir-30 reduction maintains self-renewal and inhibits apoptosis in breast tumor-initiating cells. Oncogene 2010, 29(29): 4194-4204.
30. Thiery J P, Acloque H, Huang R Y, Nieto M A: Epithelial-mesenchymal transitions in development and disease. Cell 2009, 139(5):871-890.
31. Kalluri R: EMT: when epithelial cells decide to become mesenchymal-like cells. J Clin Invest 2009, 119(6):1417-1419.
32. Xu J, Lamouille S, Derynck R: TGF-beta-induced epithelial to mesenchymal transition. Cell Res 2009, 19(2):156-172.
33. Davies J A: Mesenchyme to epithelium transition during development of the mammalian kidney tubule. Acta Anat (Basel) 1996, 156(3):187-201.
34. Thiery J P: Epithelial-mesenchymal transitions in development and pathologies. Curr Opin Cell Biol 2003, 15(6): 740-746.
35. Yang J, Mani S A, Donaher J L, Ramaswamy S, Itzykson R A, Come C, Savagner P, Gitelman I, Richardson A, Weinberg R A: Twist, a master regulator of morphogenesis, plays an essential role in tumor metastasis. Cell 2004, 117(7):927-939.
36. Shin S Y, Rath O, Zebisch A, Choo S M, Kolch W, Cho K H: Functional roles of multiple feedback loops in extracellular signal-regulated kinase and Wnt signaling pathways that regulate epithelial-mesenchymal transition. Cancer Res 2010, 70(17):6715-6724.
37. Wu Y, Deng J, Rychahou P G, Qiu S, Evers B M, Zhou B P: Stabilization of snail by NF-kappaB is required for inflammation-induced cell migration and invasion. Cancer Cell 2009, 15(5):416-428.
38. Yang M H, Wu M Z, Chiou S H, Chen P M, Chang S Y, Liu C J, Teng S C, Wu K J: Direct regulation of TWIST by HIF-1alpha promotes metastasis. Nat Cell Biol 2008, 10(3):295-305.
39. Gjerdrum C, Tiron C, Hoiby T, Stefansson I, Haugen H, Sandal T, Collett K, Li S, McCormack E, Gjertsen B T et al: Axl is an essential epithelial-to-mesenchymal transition-induced regulator of breast cancer metastasis and patient survival. Proc Natl Acad Sci USA 2010, 107(3):1124-1129.
40. Kudo-Saito C, Shirako H, Takeuchi T, Kawakami Y: Cancer metastasis is accelerated through immunosuppression during Snail-induced EMT of cancer cells. Cancer Cell 2009, 15(3):195-206.
41. Thompson E W, Newgreen D F, Tarin D: Carcinoma invasion and metastasis: a role for epithelial-mesenchymal transition? Cancer research 2005, 65(14):5991-5995.
42. Gupta P B, Onder T T, Jiang G, Tao K, Kuperwasser C, Weinberg R A, Lander E S: Identification of selective inhibitors of cancer stem cells by high-throughput screening. Cell 2009, 138(4):645-659.
43. Skvortsova I, Skvortsov S, Raju U, Stasyk T, Riesterer O, Schottdorf E M, Popper B A, Schiestl B, Eichberger P, Debbage P et al: Epithelial-to-mesenchymal transition and c-myc expression are the determinants of cetuximab-induced enhancement of squamous cell carcinoma radioresponse. Radiother Oncol 2010, 96(1):108-115.
44. Bandyopadhyay A, Wang L, Agyin J, Tang Y, Lin S, Yeh I T, De K, Sun L Z: Doxorubicin in combination with a small TGFbeta inhibitor: a potential novel therapy for metastatic breast cancer in mouse models. PLoS ONE 2010, 5(4):e10365.
45. Mani S A, Guo W, Liao M J, Eaton E N, Ayyanan A, Zhou A Y, Brooks M, Reinhard F, Zhang C C, Shipitsin M et al: The epithelial-mesenchymal transition generates cells with properties of stem cells. Cell 2008, 133(4):704-715.
46. Tsuji T, Ibaragi S, Shima K, Hu M G, Katsurano M, Sasaki A, Hu G F: Epithelial-mesenchymal transition induced by growth suppressor p12CDK2-AP1 promotes tumor cell local invasion but suppresses distant colony growth. Cancer Res 2008, 68(24):10377-10386.
47. Lim E, Vaillant F, Wu D, Forrest N C, Pal B, Hart A H, Asselin-Labat M L, Gyorki D E, Ward T, Partanen A et al: Aberrant luminal progenitors as the candidate target population for basal tumor development in BRCA1 mutation carriers. Nat Med 2009, 15(8):907-913.
48. Keller P J, Arendt L M, Skibinski A, Logvinenko T, Klebba I, Dong S, Smith A E, Prat A, Perou C M, Gilmore H et al: Defining the cellular precursors to human breast cancer. Proc Natl Acad Sci USA 2011.
49. Biddle A, Liang X, Gammon L, Fazil B, Harper U, Emich H, Costea D E, Mackenzie I C: Cancer stem cells in squamous cell carcinoma switch between two distinct phenotypes that are preferentially migratory or proliferative. Cancer Res 2011, 71(15):5317-5326.
50. Aktas B, Tewes M, Fehm T, Hauch S, Kimmig R, Kasimir-Bauer S: Stem cell and epithelial-mesenchymal transition markers are frequently overexpressed in circulating tumor cells of metastatic breast cancer patients. Breast Cancer Res 2009, 11(4):R46.
51. Shipitsin M, Campbell L L, Argani P, Weremowicz S, Bloushtain-Qimron N, Yao J, Nikolskaya T, Serebryiskaya T, Beroukhim R, Hu M et al: Molecular definition of breast tumor heterogeneity. Cancer Cell 2007, 11(3):259-273.
52. Chen J, Wang L, Matyunina L V, Hill C G, McDonald J F: Overexpression of miR-429 induces mesenchymal-to-epithelial transition (MET) in metastatic ovarian cancer cells. Gynecol Oncol 2011, 121(1):200-205.
53. Li Z, Yang C S, Nakashima K, Rana T M: Small RNA-mediated regulation of iPS cell generation. EMBO J 2011, 30(5):823-834.
54. Chaffer C L, Brennan J P, Slavin J L, Blick T, Thompson E W, Williams E D: Mesenchymal-to-epithelial transition facilitates bladder cancer metastasis: role of fibroblast growth factor receptor-2. Cancer Res 2006, 66(23):11271-11278.
55. Chao Y L, Shepard C R, Wells A: Breast carcinoma cells re-express E-cadherin during mesenchymal to epithelial reverting transition. Mol Cancer 2010, 9:179.
56. Yates C C, Shepard C R, Stolz D B, Wells A: Co-culturing human prostate carcinoma cells with hepatocytes leads to increased expression of E-cadherin. Br J Cancer 2007, 96(8):1246-1252.
57. Sheridan C, Kishimoto H, Fuchs R K, Mehrotra S, Bhat-Nakshatri P, Turner C H, Goulet R, Jr., Badve S, Nakshatri H: CD44+/CD24− breast cancer cells exhibit enhanced invasive properties: an early step necessary for metastasis. Breast Cancer Res 2006, 8(5):R59.

Additional References (See Example 2)

1. Reya, T., Morrison, S. J., Clarke, M. F. & Weissman, I. L. Stem cells, cancer, and cancer stem cells. Nature. 414 (6859), 105-111 (2001).
2. Al-Hajj, M., Wicha, M. S., Benito-Hernandez, A., Morrison, S. J. & Clarke, M. F. Prospective identification of tumorigenic breast cancer cells. Proc Natl Acad Sci USA 100, 3983-3988 (2003).
3. Ginestier, C., et al. ALDH1 is a marker of normal and malignant human mammary stem cells and a predictor of poor clinical outcome. Cell Stem Cell 1, 555-567 (2007).
4. Mani, S. A., et al. The epithelial-mesenchymal transition generates cells with properties of stem cells. Cell 133, 704-715 (2008).
5. Tsuji, T., et al. Epithelial-mesenchymal transition induced by growth suppressor p12CDK2-AP1 promotes tumor cell local invasion but suppresses distant colony growth. Cancer Res 68, 10377-10386 (2008).
6. Li, X., et al. Intrinsic resistance of tumorigenic breast cancer cells to chemotherapy. J Natl Cancer Inst 100, 672-679 (2008).
7. Creighton, C. J., et al. Residual breast cancers after conventional therapy display mesenchymal as well as tumor-initiating features. Proc Natl Acad Sci USA 106, 13820-13825 (2009).
8. Conley, S. J., et al. Antiangiogenic agents increase breast cancer stem cells via the generation of tumor hypoxia. Proc Natl Acad Sci USA 109, 2784-2789 (2012).
9. Liu, S., et al. Breast cancer stem cells are regulated by mesenchymal stem cells through cytokine networks. Cancer Res 71, 614-624 (2011).
10. Ocana, O. H., et al. Metastatic colonization requires the repression of the epithelial-mesenchymal transition inducer prrxl. Cancer Cell 22, 709-724 (2012).
11. Tsai, J. H., Donaher, J. L., Murphy, D. A., Chau, S. & Yang, J. Spatiotemporal regulation of epithelial-mesenchymal transition is essential for squamous cell carcinoma metastasis. Cancer Cell 22, 725-736 (2012).
12. Britschgi, A., et al. JAK2/STAT5 Inhibition Circumvents Resistance to PI3K/mTOR Blockade: A Rationale for Cotargeting These Pathways in Metastatic Breast Cancer. Cancer Cell 22, 796-811 (2012).
13. Lim, E., et al. Aberrant luminal progenitors as the candidate target population for basal tumor development in BRCA1 mutation carriers. Nat Med 15, 907-913 (2009).
14. Keller, P. J., et al. Defining the cellular precursors to human breast cancer. Proc Natl Acad Sci USA 109, 2772-2777 (2012).
15. Keller, P. J., et al. Mapping the cellular and molecular heterogeneity of normal and malignant breast tissues and cultured cell lines. Breast Cancer Res 12, R87 (2010).
16. Liu, S., et al. Hedgehog signaling and Bmi-1 regulate self-renewal of normal and malignant human mammary stem cells. Cancer Res 66, 6063-6071 (2006).
17. Shehata, M., et al. Phenotypic and functional characterization of the luminal cell hierarchy of the mammary gland. Breast Cancer Res 14, R134 (2012).
18. Vaillant, F., Lindeman, G. J. & Visvader, J. E. Jekyll or Hyde: does Matrigel provide a more or less physiological environment in mammary repopulating assays? Breast Cancer Res 13, 108 (2011).
19. Hudson, D. L. Epithelial stem cells in human prostate growth and disease. Prostate Cancer Prostatic Dis 7, 188-194 (2004).
20. Lawson, D. A., et al. Basal epithelial stem cells are efficient targets for prostate cancer initiation. Proc Natl Acad Sci USA 107, 2610-2615 (2010).
21. Wang, X., et al. A luminal epithelial stem cell that is a cell of origin for prostate cancer. Nature 461, 495-500 (2009).
22. Comprehensive molecular portraits of human breast tumours. Nature 490, 61-70 (2012).
23. Liu, S., et al. BRCA1 regulates human mammary stem/progenitor cell fate. Proc Natl Acad Sci USA 105, 1680-1685 (2008).
24. Neve, R. M., et al. A collection of breast cancer cell lines for the study of functionally distinct cancer subtypes. Cancer Cell 10, 515-527 (2006).
25. Liu, S., et al. MicroRNA93 regulates proliferation and differentiation of normal and malignant breast stem cells. PLoS Genet 8, e1002751 (2012).
26. Irizarry, R. A., et al. Exploration, normalization, and summaries of high density oligonucleotide array probe level data. Biostatistics (Oxford, England) 4, 249-264 (2003).
27. Weaver, V. M. & Bissell, M. J. Functional culture models to study mechanisms governing apoptosis in normal and malignant mammary epithelial cells. Journal of Mammary Gland Biology and Neoplasia 4, 193-201 (1999).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of reducing the number of EMT and MET type breast cancer stem cells in a subject with said EMT and MET type breast cancer stem cells comprising co-administering to said subject an effective amount of:
   a) a first therapeutic agent directed against EMT type cancer stem cells, wherein said first therapeutic agent comprises an IL6R antibody, and
   b) a second therapeutic agent directed against MET type cancer stem cells, wherein said second therapeutic agent comprises an anti-Her2 antibody, and
   wherein the number of both said EMT and said MET type breast cancer stem cells in said subject are reduced.

2. The method of claim 1, wherein said subject comprises bulk breast cancer cells that are not breast cancer stem cells, and wherein the method further comprises co-administering a third therapeutic agent to said subject, wherein said third therapeutic agent is capable of killing or inhibiting said bulk breast cancer cells, and wherein the number of said bulk breast cancer cells is reduced.

3. The method of claim 1, wherein said first therapeutic agent comprises tociluzumab.

4. The method of claim 3, wherein said second therapeutic agent comprises trastuzumab.

* * * * *

SEQUENCE LISTING

```
<160> NUMBER OF SEQ ID NOS: 3

<210> SEQ ID NO 1
<211> LENGTH: 80
<212> TYPE: DNA
<213> ORGANISM: Homo sapiens

<400> SEQUENCE: 1
ctgggggctc caaagtgctg ttcgtgcagg tagtgtgatt acccaaccta ctgctgagct    60
agcacttccc gagccccgg                                                 80
```

```
<210> SEQ ID NO 2
<211> LENGTH: 80
<212> TYPE: DNA
<213> ORGANISM: Homo sapiens

<400> SEQUENCE: 2
cctgttgcca caaacccgta gatccgaact tgtggtatta gtccgcacaa gcttgtatct      60
ataggtatgt gtctgttagg                                                 80

<210> SEQ ID NO 3
<211> LENGTH: 110
<212> TYPE: DNA
<213> ORGANISM: Homo sapiens

<400> SEQUENCE: 3
tgaacatcca ggtctggggc atgaacctgg catacaatgt agatttctgt gttcgttagg      60
caacagctac attgtctgct gggtttcagg ctacctggaa acatgttctc                110
```